United States Patent [19]
Fisher et al.

[11] Patent Number: 5,852,029
[45] Date of Patent: Dec. 22, 1998

[54] AZA SPIRO COMPOUNDS ACTING ON THE CHOLINERGIC SYSTEM WITH MUSCARINIC AGONIST ACTIVITY

[75] Inventors: Abraham Fisher, Holon; Yishal Karton, Ness-Ziona; Daniele Marciano, Ramat-Hasharon; Dov Barak, Rehovot; Haim Meshulam, Bat Yam, all of Israel

[73] Assignee: Israel Institute for Biological Research, Nessziona, Israel

[21] Appl. No.: 627,222

[22] Filed: Jan. 18, 1996

Related U.S. Application Data

[63] Continuation-in-part of Ser. No. 94,855, Jul. 20, 1993, Pat. No. 5,534,520, which is a continuation-in-part of Ser. No. 685,397, Apr. 9, 1991, abandoned, which is a continuation-in-part of Ser. No. 507,708, Apr. 10, 1990, abandoned.

[51] Int. Cl.⁶ ............ C07D 491/10; C07D 491/20; A61K 31/445; A61K 31/46
[52] U.S. Cl. ............ 514/278; 546/16; 546/19; 546/20
[58] Field of Search .............. 546/19, 16, 20; 514/278

[56] References Cited

U.S. PATENT DOCUMENTS 3,161,644  12/1964  Beilstein ............... 546/215

(List continued on next page.)

FOREIGN PATENT DOCUMENTS 0 189 370  7/1986  European Pat. Off. .

(List continued on next page.)

OTHER PUBLICATIONS

*Chemical Abstracts* 119: 16165 m, Oct. 11, 1993.

(List continued on next page.)

*Primary Examiner*—Alan L. Rotman
*Attorney, Agent, or Firm*—Darby & Darby

[57] ABSTRACT

Compounds useful for treating diseases of the central or peripheral nervous system in mammals have formulae I–XII

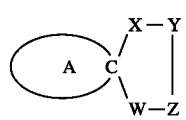

I

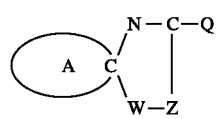

II

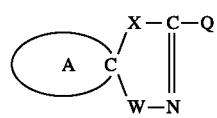

III

-continued

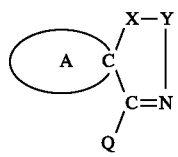

IV

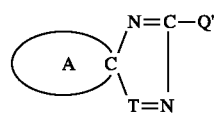

V

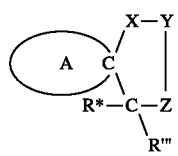

VI

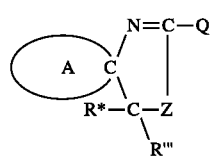

VII

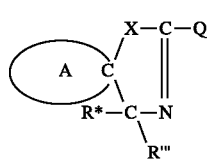

VIII

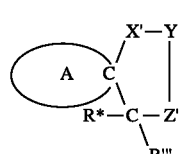

IX

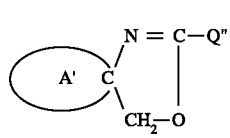

X

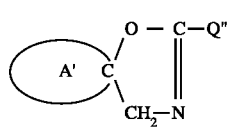

XI

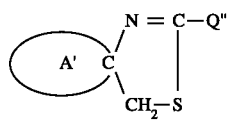

XII

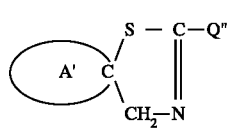

XIII wherein ring A or A' together with the spiro-carbon atom constitutes a bridged or unbridged ring containing one or two ring nitrogen atoms; and the other symbols have specified values, subject to certain conditions.

9 Claims, No Drawings

U.S. PATENT DOCUMENTS

| | | | |
|---|---|---|---|
| 3,629,276 | 12/1971 | Harnden | 548/216 |
| 3,717,634 | 2/1973 | Wu et al. | 544/230 |
| 3,784,551 | 1/1974 | Nakaniski et al. | 546/19 |
| 3,792,053 | 2/1974 | Potoski et al. | 546/137 |
| 3,850,949 | 11/1974 | Ono et al. | 548/240 |
| 4,083,985 | 4/1978 | Cohen et al. | 514/294 |
| 4,104,397 | 8/1978 | Cohen et al. | 514/278 |
| 4,735,944 | 4/1988 | Bollinger | 514/278 |
| 4,746,655 | 5/1988 | Cale, Jr. | 514/211 |
| 4,855,290 | 8/1989 | Fisher et al. | 514/278 |
| 4,900,830 | 2/1990 | Fisher et al. | 546/18 |
| 4,981,858 | 1/1991 | Fisher et al. | 514/278 |
| 5,073,560 | 12/1991 | Wu et al. | 514/278 |
| 5,534,520 | 7/1996 | Fisher et al. | 514/278 |

FOREIGN PATENT DOCUMENTS

| | | |
|---|---|---|
| 0 205 247 | 12/1986 | European Pat. Off. . |
| 273659 A1 | 7/1988 | European Pat. Off. . |
| 0 303 391 | 2/1989 | European Pat. Off. . |
| 0 311 313 | 4/1989 | European Pat. Off. . |
| 0 314 444 | 5/1989 | European Pat. Off. . |
| 412821 A2 | 2/1991 | European Pat. Off. . |
| 2757107 | 7/1908 | Germany . |
| 2252612 | 5/1973 | Germany . |
| 63-208 590 | 8/1988 | Japan . |
| 2-164 882 | 6/1990 | Japan . |
| 2164882 | 6/1990 | Japan . |
| 2-247 183 | 10/1990 | Japan . |
| 201 312 | 3/1993 | Taiwan . |

OTHER PUBLICATIONS

*Chemical Abstracts* 119: 101570f, Aug. 1993.
*Chemical Abstracts* 119: 101573j, Aug. 1993.
*Chemical Abstracts* 119: 140115j, Sep. 27, 1993.
*Chemical Abstracts* 114: 164201q, Apr. 29, 1991.
*Chemical Abstracts* 110: 114821p, Mar. 27, 1989.
*Chemical Abstracts* 110: 140112f, Apr. 17, 1989.
*Chemical Abstracts* 110: 140094y, Apr. 17, 1989.
*Chemical Abstracts* 110: 140152u, Apr. 17, 1989.
*Chemical Abstracts* 110: 101632c: Mar. 20, 1989.
Nordvall, G., Analogues of the Muscarinic Agent 2–Methylspiro [1–azabicyclo [2.2.2.] octane–3,4–[1,3]dioxolane]: Synthesis and pharmacology, *J. Med. Chem.* 1992, 35, 1541–1550.

Abstract of TW 201312 (State of Israel Inst. Biol. Res.) Mar. 1, 1993.
*J.Med.Chem.* vol. 30, 1987, Washington, pp. 969–975, Saunders, J.Et al. "Synthesis and Charactersiation of all four isomers".
*J.Med.Chem.* vol. 31, 1988, Washington, pp. 486–491 Saunders, J.etal. "2–Methyl–1,3–diaazaspiro[4.5decanes as novel Muscarinic Cholinergic Agonsits".
*J.Med.Chem.* vol. 35, 1992, Washington, pp. 1541–1550; Nordvall,G.et al. "Analogues ofthe Muscarinic Agent".
*Chem. Abstracts*, vol. 71(91), 91359–d, Nov. 10, 1969.
*Chem. Abstracts*, vol. 73(19), 98869–V, Nov. 9, 1970.
*Chem. Abstracts*, vol. 97(17), 144165H, Oct. 25, 1982.
*Chem. Abstracts*, vol. 109(3) 16597–e, Jul. 18, 1988.
Trigo et al., *Journal of Heterocyclic Chemistry*, vol. 21, No. 5, pp. 1479–83, Sep.–Oct. 1984.
E. Galvez, et al., Synthesis and Structural Study of cyclopenatne, Indene and Fluorene Spiro–derivatives, *Journal of Heterocyclic Chemistry*, 20, 13, 1983.
P.L. Feldman, et al., A Novel route to the Class of Analgetics *Journal of Organic Chemistry*, 55, 4207–4209, 1990.
Y. Ishihara, et al., Central Cholinergic Agemts. III. Synthesis of 2–Alkoxy–2,8–diazaspiro [4,5]decane–1,3–diones as Muscarinic Agnoists, *Chem. Pharm. Bull.*, 40(5), 1177–1185, 1992.
G.G. Trigo, et al., Synthesis ans Structural Study of Quinuclidine Spiro Derivatives, *Journal of Heterocyclic Chemistry*, 18, 1507–1511 ,1981.
M.V. Garcia, et al., Study of the Reaction Between Cyanohydrin and Chlorosulfonyl Isocyanate. A New, Efficient Method for the One–Pot Synthesis of 2,4–Oxazolidinediones, Synthesis, 1991.
A. Jossang, et al. Horsfiline, an Oxindole Alkaloid from Horsfieldia superba, *Journal of Organic Chemistry*, 56, 6527–6530, 1991.
G.M. Carrera, Jr., et al., Synthesis of Novel Substituted Spirohydantoins, *Jornal of Heterocyclic Chemistry*, 29, 847–85 1992.
G.G. Trigo, et al., PMR and 13C–NMR Spectroscopy of Tropane an N–Substituted Nortopane Spirohydantoins, *Journal of Pharmaceutical Sciences*, 70(1), 87–89, 1981.
L.G. Wade,Jr. Organic Chemistry, p. 349, Prentice–Hall Publishers, 1987.

AZA SPIRO COMPOUNDS ACTING ON THE CHOLINERGIC SYSTEM WITH MUSCARINIC AGONIST ACTIVITY

This is a continuation of International application Ser. No. PCT/GB94/01543, filed which is a continuation-in-part of U.S. application Ser. No. 08/094,855, filed Jul. 20, 1993, U.S. Pat. No. 5,534,520 which in turn is a continuation-in-part of U.S. application Ser. No. 07/685,397, now abandoned, which in turn is a continuation-in-part of Ser. No. 07/507,708 filed Apr. 10, 1990, now abandoned.

FIELD AND BACKGROUND OF THE INVENTION

The present invention relates to Spiro five-membered ring compounds in which the ring which is spiro-connected to the five-membered ring as set forth herein is a saturated bridged or unbridged ring containing one or two nitrogen atoms; to pharmaceutical compositions containing the spiro compounds and to a method for treating diseases of the central and peripheral nervous system using such spiro-compounds or pharmaceutical compositions.

Novel spiro-quinuclidine compounds, in which oxathiolane rings were connected in spiro manner with quinuclidine rings, were described e.g. in European patent application No. 0205247 A2, published Dec. 17, 1986, and in U.S. Pat. Nos. 4,855,290 (issued Aug. 8, 1989). 4,981,858 (issued Jan. 1. 1991), 4,900,830 (issued Feb. 13, 1990) and 4,876, 260 (issued Oct. 24, 1989). Similarly, some spiro-oxazolines have been described in U.S. Pat. No. 5,053,412 (issued Oct. 5.053,412), while some spiro-oxazolines and some spiro-thiazolines have been described in U.S. patent application Ser. No. 07/685,397. It is to be understood that the entire contents of the above-mentioned patents and of U.S. Ser. No. 07/685,397, as well as any other patents and literature articles mentioned in the present patent application are incorporated herein by reference. The novel compounds of the above-mentioned patents possess central nervous system activity. The biological activity of 2-methylspiro(1,3-oxathiolane-5,3')quinuclidine, which exists as geometrical cis- and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of pre-clinical tests that the cis- compound (code no. AF102B) was especially promising for the control of senile dementia of Alzheimer's type (SDAT). It is also of interest that each of the cis- and trans-isomers may be optically resolved, and the biological activity of the optical isomers was also investigated in a number of cases.

It is a principal object of the invention to provide novel spiro-compounds. Further objects of the invention, and especially those which relate to the provision of useful pharmaceutical compositions and methods for the treatment of disease, will be apparent from the description which follows.

DESCRIPTION OF THE INVENTION

The present invention provides, in one aspect, novel compounds of formulae I, II, III, IV, V, VI, VII, VIII and IX

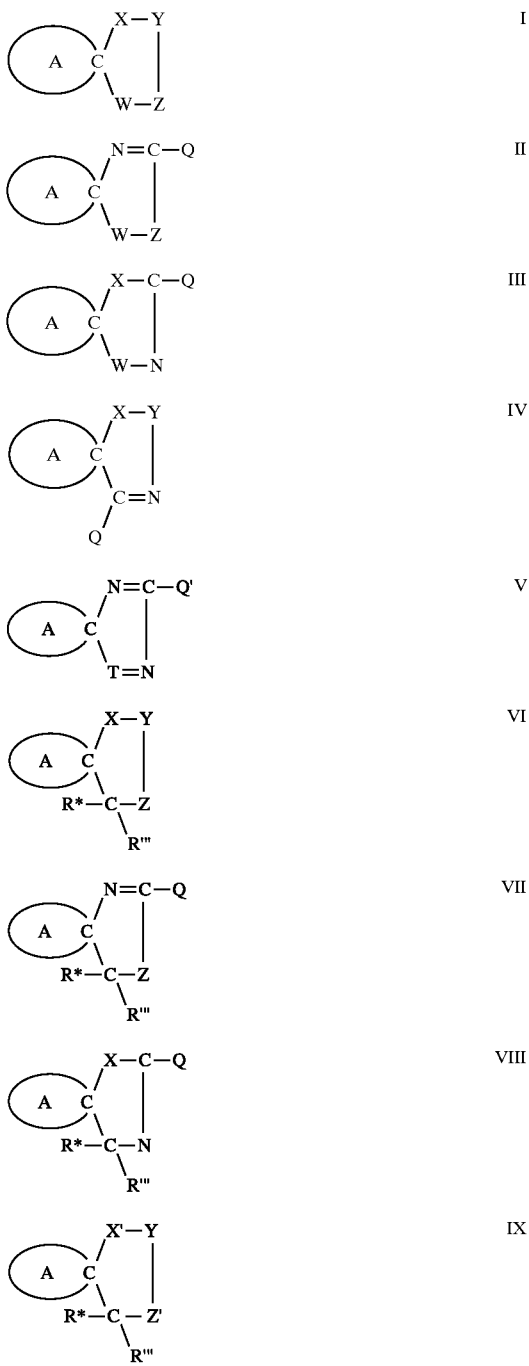

and their pharmaceutically acceptable salts, enantiomers and racemates, wherein ring A together with the spiro-carbon atom constitutes a bridged or unbridged ring containing one or two ring nitrogen atoms; X is >O, >S or >NR; T is —C(Q)= or —N=; Y is >C=O, >C=S, >C=NR° >C=CRR', >CRR', >CHOR", >O, >S or >NR°; Z is >O, >S, >C=O, >C=S, >C=NR° >C=CRR', >CRR', >CHOR" or >NR°; W is >O, >S, >C=O, >C=S, >C=NR° >C=CRR', >CHOR" or >NR°; Q and Q' are each independently selected from OR, SR, NRR' and R; X' and Z' are each independently selected from >C=O, >C=S and >C=CRR'; and R, R', R", R°, R* and R''' are each independently selected from H, $C_{1-6}$ alkyl, $C_{1-6}$ alkoxy, $C_{2-6}$ hydroxyalkyl, $C_{2-6}$ alkenyl. $C_{2-6}$ alkynyl, phenyl and $C_{1-6}$ alkyl substituted by one, two or three phenyls, while R" and R° may also be independently selected from C$_{1-6}$ alkanoyl; provided that the depicted five-membered ring contains at least one ring carbon atom in addition to the spiro-carbon atom, that no two adjacent ring atoms are simultaneously oxygen atoms, and that: (ia) in formula I, —W—Z—Y—X— is not —C(=O)—NH—C(=O)—N(alkyl)—, —C(=O)—NH—C(=O)—NH—, —O—C(=O)—CRR'—O—, —O—C(=O)—CRR'—S—, —S—, (Ib) in formula I when ring A is a piperidine ring which may be N-substituted, then —W—Z—Y—X— is not —NR°—CRR'—O—, —NR°—C(=O)—CRR'—O—, —NR°—CRR'—CRR'—S—, or —NR°—C(=O)—CRR'—S—, (Ic) in formula I when —W—Z—Y—X— is —C(=O)—NH—C(=O)—O—, then ring A is not a quinuclidine ring, (ii) in formula I, when —W—Z—Y—X— is —NH—C(=O)—N(Ph)—NH—, —NH—N(Ph)—C(=O)—NH—, —NR°—NR°C(=O)—NR°—, or —NR°—NR°—C(=S)—NR°—, then ring A is not an N-methylpiperidine ring, and when —W—Z—Y—X— is —NR°—NR°—C(=S)—NR°—, then ring A is also not an unsubstituted piperidine ring. (iiia) in formula III. ring A may not be substituted by two phenyl radicals, (iiib) in formula III, when Q is NRR' and W is C=O, then X is not O, (iv) in formula VI when Y is CRR' and either X =Z=O or S, or one of X and Z is O and the other is S, then at least one of R* and R'"≠H, (v) in formula VI when Y is CRR', X is O or S and ring A is a piperidine ring which may be N-substituted, then Z is NR° except N—CHO, (vi) in formula VI when X is O, Y is NR° End Z is C=O or C=S, then either ring A is a bridged ring or at least one of R* and R'" is not H, (vii) in formula VI when —X—Y—Z— is —O—C(=O)—NH—, —O—C(=S)—NH—, —O—NR°—C(=O)— or —O—NR°—C(=S)—, and R° is H or alkyl, then ring A is not a piperidine ring, (viii) in formula VII when Z is O, then either Q is SR or NRR', or at least one of R* and R'" is not H, (ix) in formula VIII when X is O or S, then either Q is SR, or at least one of R* and R'" is not H, and (x) in formula IX when —X'—Y—Z'— is —C(=O)—NR°—C(=O)—, and R° is H or alkyl, then ring A is not a piperidine ring.

In a particular embodiment, ring A may be selected from among the group of structures K, L, M, N, P and S, namely:

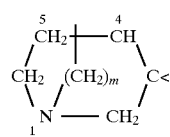

(K)

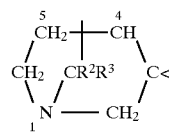

(L)

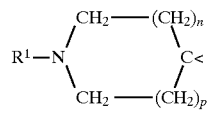

(M)

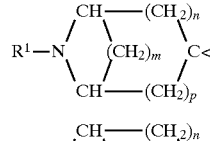

(N)

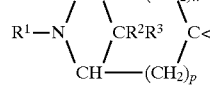

(P)

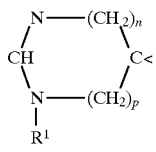

(S)

wherein each such structure is unsubstituted or is substituted by 1–3 substituents selected from C$_{1-6}$ alkyl and hydroxyl, in structures K and L the bridge is attached at one end to position 1 and at the other end to position 4 or 5 (i.e. the moiety

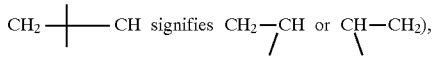

m is 1, 2 or 3, and n end p are each independently 0, 1, 2 or 3, provided that n+p =1–3; R$^1$ is selected from hydrogen, C$_{1-6}$-alkyl, C$_{2-6}$-alkenyl, C$_{2-6}$-alkynyl, C$_{3-7}$-cycloalkyl, C$_{1-6}$-alkyl substituted by 1–6 halogen atoms, hydroxy- C$_{1-6}$-alkyl, C$_{1-6}$-alkoxy, C$_{1-6}$-alkylthio, C$_{1-6}$-alkoxy-C$_{1-6}$-alkyl, carboxy-C$_{1-6}$-alkyl, (C$_{1-6}$-alkoxy)carbonyl —C$_{1-6}$-alkyl, amino-C$_{1-6}$-alkyl, mono-(C$_{1-6}$-alkyl)amino C$_{1-6}$-alkyl, di-(C$_{1-6}$-alkyl)amino-C$_{1-6}$-alkyl, 2-oxo-pyrrolidin-1-yl-methyl, aryl, diarylmethylol, C$_{1-6}$-alkyl substituted by one or two aryl groups, C$_{1-6}$-alkanoyl and arylcarbonyl; and aryl denotes unsubstituted phenyl or phenyl substituted by 1–3 substituents selected from halogen, C$_{1-6}$-alkyl, C$_{1-6}$-alkoxy and CF$_3$; and R$^2$ and R$_3$ are independently selected from C$_{1-4}$ alkyl, The invention moreover provides compounds of formulae I–IX, End salts, quaternary compounds, enantiomers and racemates thereof as defined above, wherein additionally or alternatively: in any moiety CRR', R and R' together with the carbon atom to which they are attached may form a saturated carbocyclic ring having 3–6 ring members; and in structures (K), (L), (M), (N), (P) and (S), any H atom attached to a ring carbon atom may be replaced by R$^1$ which (except for H) is as defined above.

Exemplary compounds of the invention are: 1-methylpiperidine-4-spiro-5'-(3'-ethylhydantoin); 1-methylpiperidine-4-spiro-5'-(1'-acetylhydantoin); piperidine-4-spiro-5'-(3'-ethylhydantoin); 1-methylpiperidine-4-spiro-5'-(3'-methylhydantoin); piperidine-4-spiro-5'-(3'-methylhydantoin); 1-methylpiperidine-4-spiro-5'-(3'-propargylhydantoin); 1-methylpiperidine-4-spiro-4'-(2',5'-bis(methylthio)-4'H-imidazole); 1-methylpiperidine-4-spiro-5'-(3'ethyl-4'-thiohydantoin); 1-methylpiperidine-4-spiro-5'-(4'-methylthio-3'-imidazoline-2'-thione); 1-methylpiperidine-4-spiro-5'-(2',4'-dithiohydantoin); 1-methylpiperidine-4-spiro-5'-(3'-ethyl-2',4'-dithiohydantoin); 1-methylpiperidine-4-spiro-5'-(4'-ethylthio-3'-imidazoline-2'-thione); 1-methylpiperidine-4-spiro-4'-(1-ethyl-2'-ethylthio-2'-imidazoline-5'-thione); 1-methylpiperidine-4-spiro-5'-(2'-thiohydantoin); 1-methylpiperidine-4-spiro-5'-(2'-thio-4'-β-hydroxyethyliminohydantoin); 1-methylpiperidine-4-spiro-5'-(oxazolidine-2'-thione); N-methylnortropane- 3-spiro-5'-(3'-methylhydantoin); N-methylnortropane-3-spiro-5'-(3'-ethylhydantoin); 1-methyl-piperidine-4-spiro-5'-(3'-ethyloxazolidine-2'-one); 1-methyl-piperidine-4-spiro-4'-(3'-ethyloxazolidine-2'-one); 2-N-methyl-spiro-(1,3-succinimide 4,3')quinuclidine; 2-N-ethylspiro-(1,3-succinimide 4,3')quinuclidine; 1-methylpiperidine-4-spiro-5'-(oxazolidine-2',4'-dione); 1-methyl-piperidine-4-spiro-5'-(3'-ethyloxazolidine-2',4'-dione); 1-methylpiperidine-4- spiro-4'-(2'-methyl-240-thiazoline); N-methylnortropane-3-spiro-5'-hydantoin; 1-methyl-piperidine-4-spiro-4'(5')-(2'-methyl-2'-imidazoline); 1-methylpiperidine-4-spiro-5-(2'-methyl-2'-oxazoline-4'-one); 1-methylpiperidine-4-spiro-4'(5')-[2'-methyl-4'H(5'H)-imidazol-5'(4')-one]; 1-methylpiperidine-4-spiro-4'-(2'-methylthio-5'-methoxy-4'H-imidazole); 1-methyl-piperidine-4-spiro-4'-(2'-methylthio-5'-amino-4'H-imidazole); 1-methylpiperidine-4-spiro-4'-(2-methylthio-5'-aminomethyl-4'H-imidazole); 1-methylpiperidine-4-spiro-4'-[2',5'-bis(aminomethyl)-4'H-imidazole]; & 1-methylpiperidine-4-spiro-5'-(2'-thione-3'-ethyl hydantoin); 1-methylpiperidine-4-spiro-5'-(2'-thione-3'-t-butylhydantoin); 1-propargylpiperidine-4-spiro-5'-(3'-ethylhydantoin); 1-methyl-piperidine-4-spiro-5'-[3'-(4-pyrrolidino-2-butynyl)hydantoin]; 1-methylpiperidine-4-spiro-5'-[3'-(2-butynyl)-hydantoin]; piperidine-4-spiro-5'-(3'-propargylhydantoin); 2-methyl-1,4-thiazolidine-3-one-spiro[5,3']-quinuclidine; 1-methylpiperidine-4-spiro-4'(5')-(2'-methylthio-2'-imidazoline-5'(4')-one); 1-methylpiperidine-4-spiro-4'-(1'-ethyl-2'-ethylthio-2'-imidazoline-5'-one); 1-methyl-piperidine-4-spiro-4'-(1'-ethyl-2'-imidazoline-5'-one).

The present invention moreover provides a pharmaceutical composition for use in treating diseases of the central and peripheral nervous system in mammals, which comprises an amount effective for use in treating said diseases, of at least one compound having one of the formulae I, II, III, IV, V, VI, VII, VIII and IX as defined above, including their pharmaceutically acceptable salts, enantiomers and racemates, together with at least one pharmaceutically acceptable diluent, carrier or adjuvant. Such composition is preferably in a form suitable for oral, rectal, parenteral or transdermal administration (in this case the composition may comprise additionally a low molecular weight fatty acid), or for administration by insufflation or nasal spray, and may be in unit dosage form. The at least one compound of the invention as defined above, may be present in the unit dosage in an amount in the range of, e.g. about 0.5 to about 100 mg, preferably about 5 to about 100 mg, more preferably about 10 to about 50 mg.

According to a particular embodiment of the invention, the pharmaceutical composition as described in the preceding paragraph may comprise additionally at least one further pharmacologically active compound selected from physostigmine, tetrahydroaminoacridine, choline, lecithin, piracetam. aniracetam, pramiracetam, oxtracetam, 4-aminopyridine, 3,4-diaminopyridine, somatostatin, pirenzepine, N-methylatropine, N-butylscopolamine, scopolamine, clonidine, quanfamicine, propantheline, methantheline, glycopyrrolate, tropenzilium, nortriptyline, amitriptyline, imipranine, minaprine, secoverine, AFDX-116, nicotine, alaproclate, zimelidine, deprenyl and Nerve Growth Factor.

Diseases of the central or peripheral nervous system in mammals may be treated by a method which comprises administering thereto an amount effective for use in treating said diseases, of at least one compound having one of the formulae I, II, III, IV, V, VI, VII, VIII and IX as defined above, including their pharmaceutically acceptable salts, enantiomers, tautomers and racemates. Such compounds may of course be utilized for this purpose in the form of a pharmaceutical composition according to the invention, as defined above.

The invention also provides, in a particular embodiment, compounds of any of the formulae I as defined herein, having the molecular dimensions indicated below, where: r is a reference point defined by the position of an anion corresponding to the cationic form of a non-doubly-bonded nitrogen atom, defined as $N^*$, of ring A (or A') in such compound in its most stable conformation, $X^*$ defines a ring hetero atom in the depicted 5-membered ring having any of the formulae I through IX, or X through XIII, such ring hetero atom being in a position adjacent to the Spiro carbon atom, $Z^*$ defines the next but one ring atom from $X^*$ in the depicted 5-membered ring, and $Q^*$ defines the terminal C or N atom of a side-chain attached to the ring atom between atoms $X^*$ and $Z^*$ in the 5-membered ring depicted infra, side-chain hydrogen atoms being ignored for this purpose; such molecular dimensions having substantially the following values, namely: a dihedral angle r-$X^*$-$Q^*$-$Z^*$=from $-54°$ to $-170°$; and molecular distances r-$N^*$=3.0 angstroms (the reference distance), r-$X^*$=from 5.7 to 6.75 angstroms, r-$Q^*$=from 7.9 to 8.90 angstroms, x-$Q^*$=from 2.4 to 2.8 angstroms; such compounds having the thus-defined molecular dimensions being characterized by having muscarinic agonist activity. This definition based on molecular dimensions is supported by biological tests, see especially Table 1, below.

In another embodiment, the invention provides a pharmaceutical composition which comprises at least one compound of any of the formulae I through IX as defined herein, and additionally Nerve Growth Factor (NGF), the compound(s) of the invention being present in an amount which promotes the nerve growth activity of the NGF. Most of the present compounds, unlike certain known compounds possessing central or peripheral nervous system activity, do not per se promote nerve growth activity in absence of NGF, thus allowing better control, when nerve growth promotion is desired in therapy. However, some of the most active of the present compounds promote nerve growth activity independently of NGF. Moreover, compounds of the invention which usually have activity selected from muscarinic agonist activity, amyloid precursor protein (APP) secreting activity and β-amyloids decreasing activity, and activity increasing the proportion of dephosphorylated τ proteins. Tests carried out to ascertain the biological activity of the present compounds are detailed infra.

The invention moreover provides compounds of formula (I) as depicted above, including pharmaceutically acceptable salts, quaternary compounds which are structurally derived from said compounds having a tertiary nitrogen atom, enantiomers and racemates thereof, for use in the manufacture of a medicament having biological activity selected from (a) muscarinic agonist activity, (b) neurotrophic-like or synergistic activity with NGF. (c) amyloid precursor protein (APP) secreting activity and β-amyloids decreasing activity, (d) activity increasing the proportion of dephosphorylated τ proteins, and (e) NGF-like activity, wherein —W—Z—Y—X— is —NR° CRR'—CRR'—O—, —O—C(=O)—CRR'—O—, —O—C(=O)—CRR'—S—, —NR°—C(=O)—CRR'—O—, —NR°—CRR'—CRR'—S(=O)$_q$—, or —NR°—C(=O) —CRR'—S(=O)$_q$—, q is O, 1 or 2, and R, R' and R° have the above meanings. Exemplary such compounds are: 1-methylpiperidine-4-spiro-5'-(2'-methyl-1',4'-oxazolidine-3'-one); 1-methylpiperidine-4-spiro-5'-(2'-methyl-1',4'-thiazolidine-3'-one); 1-methylpiperidine-4-spiro-5'-(2',4'-di-methyl-1',4'-thiazolidine-3'-one); 1-methylpiperidine-4-spiro-5'-(2'-ethyl-1',4'-thiazolidine-3'-one); 1-methylpiperidine-4-spiro-5'-(2'-ethyl-4-methyl-1',4'-thiazolidine-3'-one); piperidine-4-spiro-5'-(3'-methyl-1',4'-oxathiolane-2'-one); piperidine-4-spiro-5'-(2'-methyl-1',4'-thiazolidine-3'-one); 1-methylpiperidine-4-spiro-5'-(2'-methyl-3'-oxo-1',4'-thiazolidine-1'-oxide); 1-methylpiperidine-4-spiro-5'-(3'-methyl-1',4'-oxathiolane- 2'-one); 1-methylpiperidine-4-spiro-2'-(5'-methyl-1',3'-oxazolidine); 1-methylpiperidine-4-spiro-2'-(4'-ethyl-1',3'-oxazolidine); 1-methylpiperidine-4-spiro-5'-(3'-ethyl-1',4'-oxathiolane-2'-one); 1-methylpiperidine-4-spiro-5'-(2'-methyl-1',4'-thiazolidine-3'-one); 1-methylpiperidine-4-spiro-5'-(2'-ethyl-1',4'-thiazolidine-3'-one; 1-methylpiperidine-4-spiro-2'-(5'-methyl-1',3'-dioxolan-4'-one); 1-methylpiperidine-4-spiro-5'-(2'-methyl-1',4'-thiazolidine-3'-thione); and the enantiomers d- and l-1-methylpiperidine-4-spiro-5'-(2'-methyl-1',4'-thiazolidine-3'-one) and d- and l-1-methylpiperidine-4-spiro-5'-(2'-ethyl-1', 4'-thiazolidine-3'-one).

Such compounds of the invention may thus be used for treating diseases in mammals, diagnosed as being amenable to treatment with an effective amount (in the context of the above activities a-e) of the compound(s), and may be utilized in the form of pharmaceutical compositions comprising an effective amount of such compounds), but are otherwise as described above.

The methods used for preparing the present compounds are essentially those known to organic chemists for the formation of the five-membered rings, ring-substitution, changing the degree of ring saturation/unsaturation, interconversion of salts and bases, quaternary salt formation. etc. Thus, while exemplary methods of preparing certain compounds of the invention will be described, other methods can also be applied to their preparation, as will be evident to the skilled person.

When the desired five-membered ring is a hydantoin, for example, this ring may be formed by reacting the corresponding saturated N-heterocyclic ketone (e.g. 1-methylpiperidine-4-one) with $(NH_4)_2CO_3+CN^-$, and the 3'-N atom may then be substituted in known manner. These reactions may be illustrated thus:

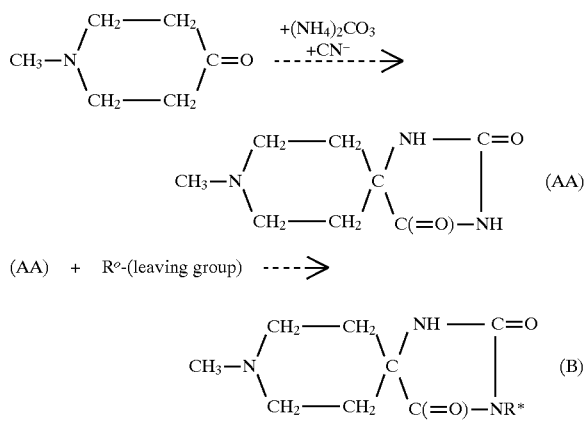

(AA) + R°-(leaving group) ----> e.g., AF160, $R^\circ$=Et; AF178, $R^\circ$=Me; AF185, $R^\circ$=propargyl; AF167, $R^\circ$=Me, analog*; and AF168, $R^\circ$=Et, analog* (*in which the N-methylpiperidine moiety contains a 2,6-ethylene bridge, i.e. the N-methylnortropane analog).

The leaving group in "R°-(leaving group)" may be e.g. bromide, chloride or p-toluenesulfonate and R° is as defined herein, excepting H, alkoxy and alkanoyl. This substitution reaction may be conducted under essentially known conditions. e.g. by reacting the 3'-unsubstituted hydantoin in presence of an alkali such as KOH and using a solvent such as ethanol. The corresponding 1',3'-disubstituted compound may be obtained in the above reaction by using excess of the "R°-(leaving group)" reagent, or by reacting compound (B) with "R°-(leaving group)".

The 1-methyl group in structure (B) may be removed by reaction with a demethylating agent such as $CH_3CH(Cl)OCOCl$:

(B) + demethylating agent ---->

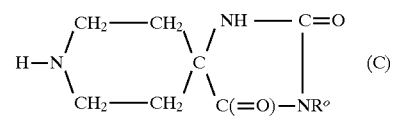

e.g. AF160(Des), R° = Et; AF179, R* = Me.

Structure (B) and may also be made e.g. as follows:

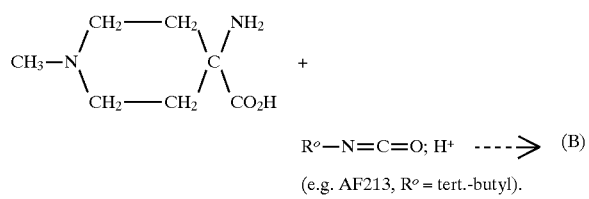

$R^\circ$—N=C=O; H⁺ ----> (B)

(e.g. AF213, R° = tert.-butyl).

Substituting $R^\circ$—N=C=S in the analogous reaction gives the (B)-3-thione, e.g. AF181 (R=Et), AF184 (R=tert.-butyl).

Reaction of compound (AA) with an alkanoyl halide or an alkanoic anhydride under standard alkanoylating conditions effects substitution in the 1'-position, thus:

(AA) + alkanoylating agent ---->

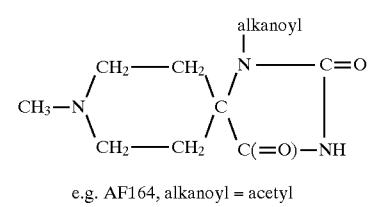

e.g. AF164, alkanoyl = acetyl

When the desired five-membered ring is a dithiohydantoin, such compounds may be prepared, e.g., by forming this ring by reacting the corresponding saturated N-heterocyclic ketone with $CN^-$, $NH_4Cl$ and $CS_2$. Where hydantoins substitute (e.g. by alkylation) on the N atoms, the thiohydantoins give N-and/or S-substituted products. The Examples (infra) illustrate the reaction conditions which give the different products, or mixtures of products which may be separated. These reactions may be illustrated as follows, where the N-heterocyclic ketone is exemplarily 1-methylpiperidine-4-one:

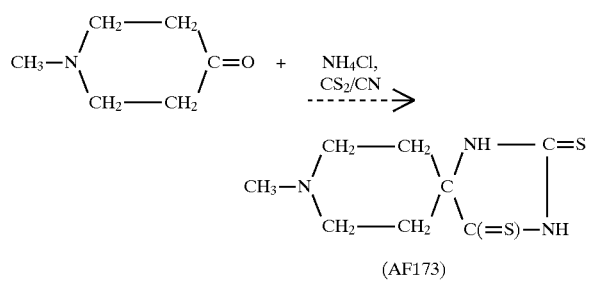

(AF173)

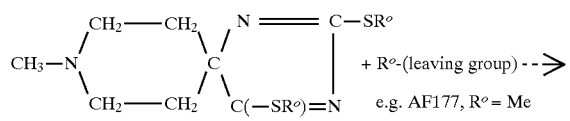

+ R°-(leaving group) --> e.g. AF177, R° = Me

-continued

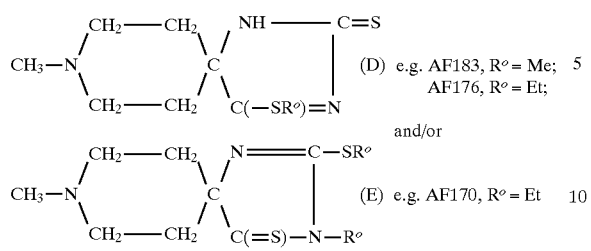

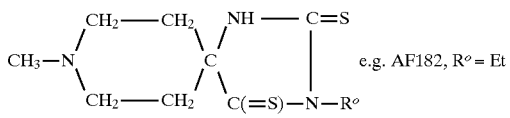

Similar reaction of compound (D) with 20% HCl gives a compound having the following structure (see e.g. Example 12):

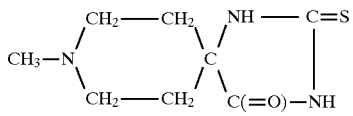

The leaving group and the value of $R^o$ in "$R^o$-(leaving group)" may be as described above for hydantoins. Substitution reactions may be conducted under essentially known conditions.

Dithiohydantoins may in general also be obtained by reacting corresponding hydantoins with $P_2S_5$. e.g., thus:

This compound is also formed by hydrolyzing the analog containing $=NR^o$ instead of $O=$; the $=NR^o$ analog may be prepared by reacting compound AF173 with $R^oNH_2$ (see e.g. Example 13, where $R^o=\beta$-hydroxyethyl).

Compounds of the invention which are oxo- or thiono-substituted oxazolidines may be prepared, e.g., as follows:

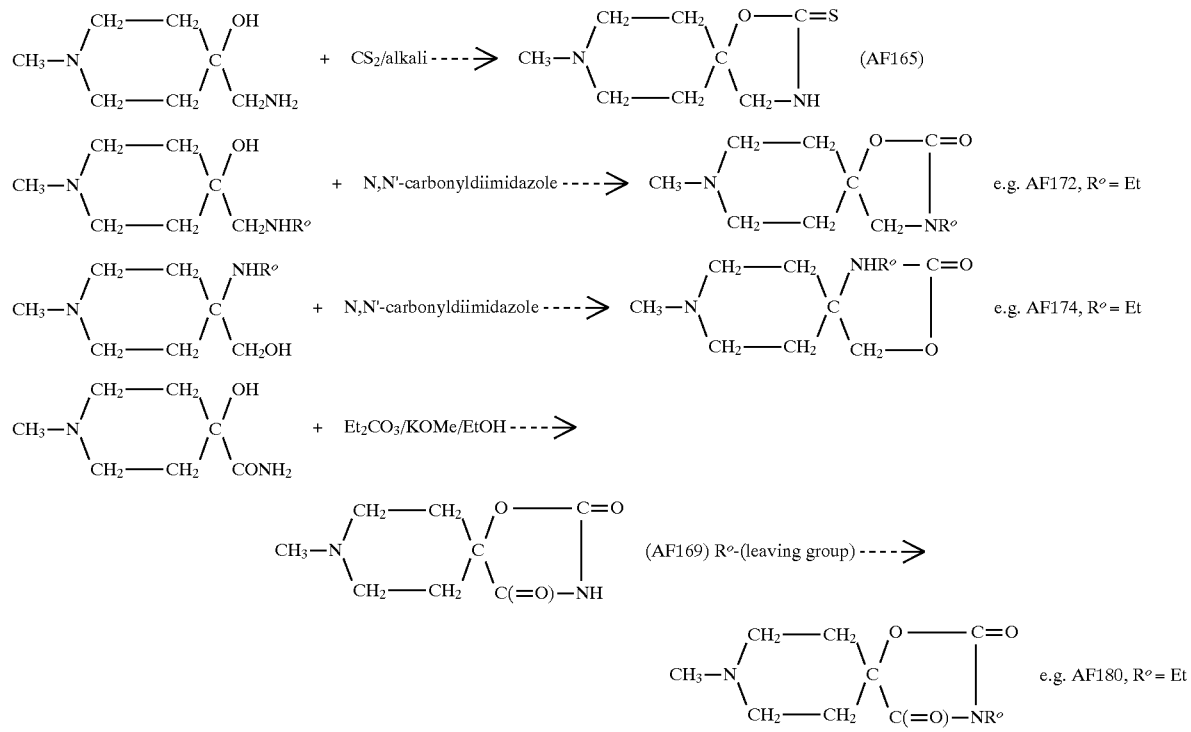

The leaving group in "$R^o$ -(leaving group)" may be as described above for the hydantoins, as is the value or $R^o$. The substitution reaction may be conducted under essentially known conditions.

Compounds of the invention in which the five-membered ring is a succinimide, may be prepared, for example, as follows:

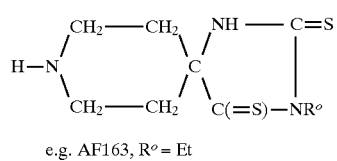

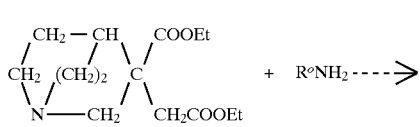

3-carboethoxy-3-carboethoxymethylquinuclidine

When compound (E) is reacted with 20% HCl, the S—$R^o$ is hydrolyzed to give the following compound:

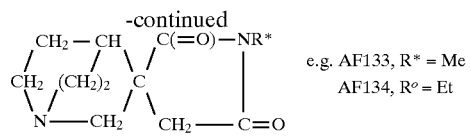

Thiazolines of the invention may be made e.g., thus:

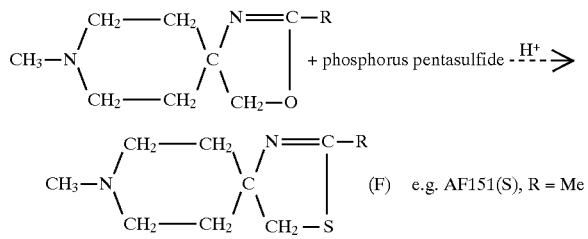

It may be mentioned in passing that the compound:

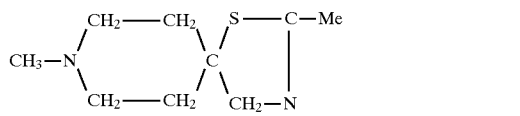

designated AF150(S), has been described in our U.S. Ser. No. 07/685,397, whereas the compounds of formula (F) were not specifically exemplified in that U.S. Patent Application. However, it has now surprisingly been found that compounds of formula (F) as exemplified by compound AF151(S), are surprisingly much more promising from a pharmacological activity point of view, than the class of compounds exemplified by AP150(S).

Imidazolines according to the present invention may be prepared, for example, according to the following scheme:

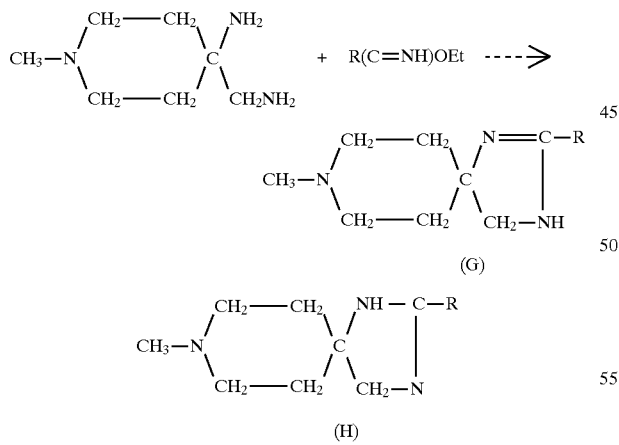

In this case the product, e.g. AF190, R=Me, may exist as a tautomeric mixture of structures (C) and (H).

Oxazolidines and thiazolidines of the invention such as structures (J) (such as AF264, R=Me, R'=H; AF268, R=H, R'=Et) and (K) (such as AF261, R=Me. R°=H; AF267, R=Et, R°=H; AF266, R=R°=Me) may be made, e.g., as described below.

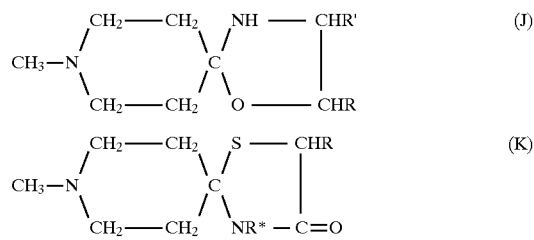

Illustratively, compounds (J) and (K) are prepared when N-methylpiperidone is reacted with HOCHRCHR'NH$_2$, or with (HSCHRCO$_2$H+R°NH$_2$, respectively.

The following compounds in which R and R° are as defined herein, but are each preferably, e.g., Me or Et, also constitute preferred compounds of the present invention.

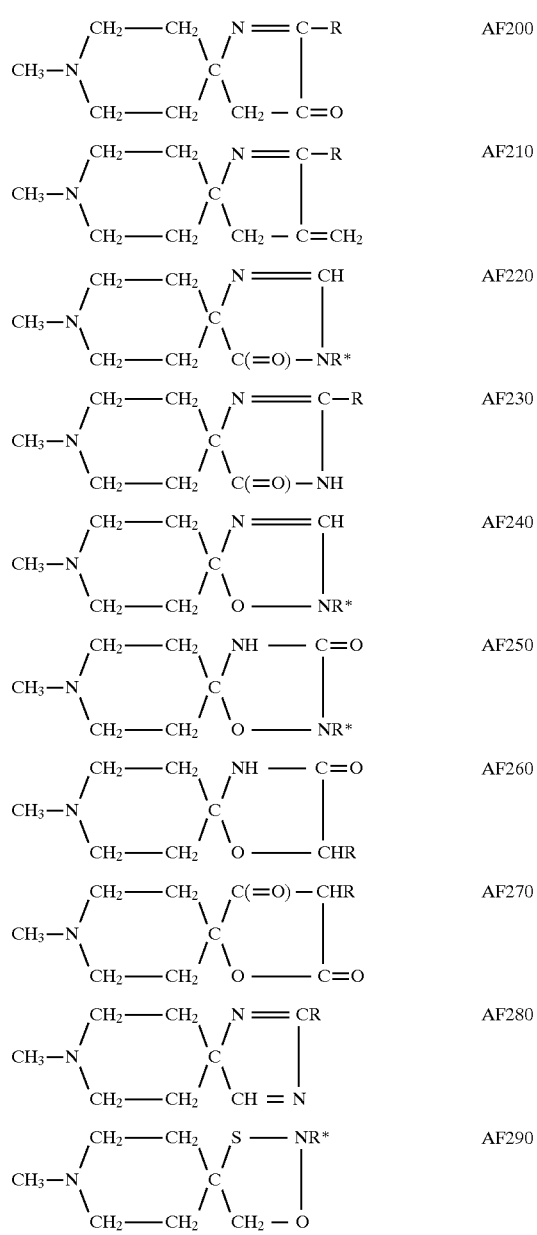

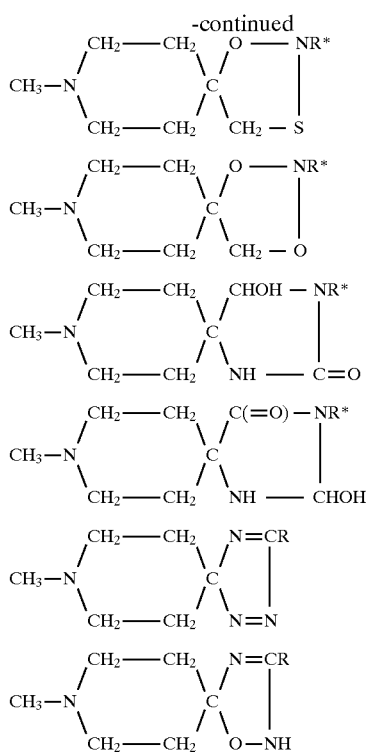

It is to be understood that whereas in the foregoing description, the illustrative compounds of the invention have shown piperidine, nortropine and quinuclidine rings, any nitrogen heterocyclic ring as defined herein as suitable for spiro-configuration with the depicted spiro five-membered ring may be substituted therefore. A similar remark applies to the practical examples, which are merely illustrative and not limitative.

The spiro-compounds of the invention are in general potentially useful for the treatment of presenile and senile dementia, senile dementia of Alzheimer's type (SDAT), atypical Alzheimer'є disease (Perry et al, Advances in Neurology, eds. R. J. Wurtman et al., 51:41, 1990), combined multiinfract dementia and Alzheimer's disease, age-associated memory impairments (AAMI), acute confusion disorders, emotional and attention disorders, mania, tardive-dyskinesia, hyperkinesia, mixed Alzheimer's and Parkinson's disease, aphasia, hallucinatory-paranoid states, post encephalitic amnesic syndrome, alcohol withdrawal symptoms, Huntington's chorea, Pick's disease, Friedrick's ataxia, Gilles de- la Tourette disease and Down syndrome, because all of these disease states are disturbances in which a central cholinergic hypofunction has been implicated at least to a certain extent. The present compounds are moreover potentially useful for the treatment of progressive supranuclear palsy; they are also potentially analgesic agents and thus may be useful in the treatment of severe painful conditions such as rheumatism, arthritis and terminal illness.

As indicated briefly above, the spiro-compounds of the present invention may be used in combination with at least one additional pharmacologically active compound, for example, acetylcholinesterase inhibitors such as physostigmine or tetrahydroaminoacridine; in combination with acetylcholine precursors such as choline or lecithin; in addition to "nootropic" drugs such as piracetam, aniracetam, oxiracetam, or pramiracetam; in addition to compounds that interact with $Ca_{2+}$ channels such as 4-aminopyridine or 3,4-diaminopyridine; or in addition to peptides that can have modulatory effects on acetylcholine release, such as somatostatin; in combination with a peripheral antimuscarinic agent (such as pirenzepine, N-methylatropine, N-butylscopolamine, propantheline, methantheline, glycopyrrolate, or tropenzilium) to counteract peripheral adverse effects that might be expected at high doses, such as salivation, diarrhea, gastric secretion or vomiting, or in combination with transdermal scopolamine such as Scopoderm$_{(R)}$ to counteract nausea and/or vomiting; in combination with antidepressants such as nortriptyline, amitriptyline, imipramine, minaprine in order to alleviate both the cognitive impairments an& depressive symptoms associated sometimes with SDAT, AAMI, mixed SDAT/ Parkinson's disease (PD); in combination with M2-antimuscarinic drugs such as secoverine, AFDX-116 (c.f. Hammer et al, 1986 Life Sci. 38:1653) in order to counteract peripheral adverse side effects that might be expected at high doses of the compounds, to counteract inhibitory effects of such agonists at central inhibitory presynaptic and postsynaptic receptors of M2 type and to potentiate the release of acetylcholine via inhibition of inhibitory autoreceptors of M2 type at intact terminals; in combination with nicotinic agonists such as nicotine in order to stimulate both the nicotinic and muscarinic receptors in the brain; in combination with an adrenergic agonist (clonidine or quanfamicine) in order to alleviate both the cognitive and other impairments associated with a mixed cholinergic-noradrenergic deficiency in SDAT; in combination with inhibitors of neuronal serotonin reuptake such as alaproclate, zimelidine in order to alleviate both the cognitive and other emotional functions in SDAT; in combination with monoamine oxidase-B inhibitors like deprenyl in order to alleviate both cognitive and other motor impairments associated with mixed states such as SDAT/PD; in combination with Nerve Growth Factor (NGF, which is administered either by a nasal spray or intracerebroventricularly).

The spiro-compounds of the present invention, with or without the aforementioned additional active substances, can be to administered for example, by way of injection in a suitable diluent or carrier, per os, rectally in the form of suppositories, by way of insufflation or nasal spray, by infusion or transdermally in a suitable vehicle with or without physostigmine or tetrahydroaminoacridine.

The present spiro-compounds may also be of potential use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyryl-cholinesterase, and may also be used for the treatment of peripheral cholinergic disorders such as myasthenia gravis, urinary bladder dysfunctions, Adi's disease and Eaton-Lambert disease. These compounds might also be used in disturbances where cholinergic underactivity is induced by drugs.

Where the present spiro-compounds are anticholinergic agents (which may readily determined by the skilled person) they may potentially be used for treatment of disorders due to a cholinergic hyperfunction, whether this be spontaneous or drug-induced. Moreover, the present compounds are of potential use in the treatment of various diseases such as PD, pseudo-PD, mixed An/PD, primary dystonias, spasmodic torticollis, cranial dystonia, depression, motion sickness, akathisia (after neuroleptic withdrawal), central hypertension, human head injury, mixed tardive dyskinesia and PD, manic-depression, as adjuncts in surgery instead of atropine, scopolamine, etc., in intoxication due to an excess of acetylcholine like inhibition of acetylcholinesterase. These may also be used in ophthalmology when either prolonged or short-term mydriasis is required.

The present spiro-compounds may also potentially be used in the treatment of disease characterized by excess peripheral-like activity such as asthma, chronic obstructive pulmonary disease, peptic ulcer disease. For these peripheral disorders it is particularly recommended to use quaternary salts of the present compounds.

Quaternary ammonium salts are widely used in therapy at the present time. Thus, examples of such cholinergic agonists are acetylcholine chloride, bethanechol chloride and carbachol (see e.g. Goodman & Gilman's "The Pharmacological Basis of Therapeutics", Seventh Edition, Macmillan Publishing Co., 1985, at page 104). Quaternary anticholinesterase agents are, e.g., neostigmine bromide, ambenonium chloride, pyridostigmine bromide, edrophonium chloride, demecarium bromide, and echothiphate iodide; pralidoxime chloride is used as a cholinesterase reactivator (see Goodman & Gilman, loc cit, at pages 122–123).

Quaternary derivatives of belladonna alkaloids, e.g. methscopolamine bromide and homatropine methylbromide, and synthetic quaternary compounds. e.g. methantheline bromide, and propantheline bromide, are used in treating gastrointestinal disorders (see Goodman & Gilman. loc cit. at pages 139–140).

In "Medicinal Chemistry" by Alfred Burger, Second Edition, Interscience Publishers, 1960, at page 497, there is mentioned a prediction that quaternary ammonium ions, regardless of their chemical structure, produce curareform paralysis and the later corroboration of this prediction. This property of quaternary compounds is utilized in anesthesia, e.g. as an adjuvant in surgical anesthesia to obtain relaxation of skeletal muscle (see Goodman & Gilan, loc cit, in Chapter 11 under the title of "Neuromuscular Blocking Agents". at pages 222–235).

This neuromuscular blocking activity of quaternary compounds, as discussed above, has not prevented development and the clinical application of quaternary compounds in therapeutics in the ensuing years. The skilled person would be aware that many factors influence the selection of any compound (including a quaternary compound) for application in clinical therapy, e.g., effectiveness for the intended purpose, safety, possible side-effects and therapeutic index. The skilled addressee would thus well understand how to interpret the expression "pharmaceutically acceptable quaternary compounds". which are structurally derived from the inventive compounds having a tertiary nitrogen atom, as this expression is used in the present specification and claims. In the light of the relevant knowledge available in the art.

The invention will now be illustrated by the following non-limiting Examples.

EXAMPLE 1

1-Methylpiperidine-4-spiro-5'-(3'-ethylhydantoin)
AF160 a) 1-Methylpiperidine-4-spiro-5'-hydantoin

A mixture of solutions of 1-methylpiperidine-4-one (36.44 g, 0.322 mole) in ethanol (150 ml), ammonium carbonate (93.0 g. 0.968 mole) in water (400 ml) and potassium cyanide (25.8 g, 0.396 mole) in water (82 ml) was heated at 60° C. for 2.5 hr., and then left at room temperature overnight. The precipitated 1-methylpiperidine-4-spiro-5'-hydantoin was filtered off and washed with small amounts of cold water, ethanol and ether to give a crystalline powder (27.0 g); Concentration of the filtrate and washings gave a second crop (20.0 g). The product was crystallized from methanol mp. 265–276 (dec.).

IR (KBr) 3170 (NE); 1700 (C=O) cm$^{-1}$.

Mass Spectrum m/e 183(M$^+$, 38%); 71 (100%).

$^1$H-NMR (D$_2$O) 1.8 (2H); 2.06 (sextet, 2H); 2.49(s, —CH$_3$); 2.58 (t, 2H); 3.14 (t, 1H); 3.20 (t, 1 H) ppm.

b) 4-Amino-1-methylpiperidine-4-carboxylic acid

1-Methylpiperidine-4-spiro-5'-hydantoin (9.75 g. 0.0533 mole) and barium hydroxide octahydrate (28.8 g, 0.9913 mole) in water (150 ml) were heated at 160° C. in a bomb for 3 hr. The content of four such batches were combined and the precipitated barium carbonate was filtered off. The filtrate was neutralized with solid CO$_2$ and the precipitate removed by filtration. Concentration of the filtrate gave 4-amino-1-methyl-piperidine-4-carboxylic acid (32.0 g, 95%) mp. 275°–280° C. (dec.).

IR (KBr) 3300, 1655, 1580 cm$^{-1}$

Mass Spectrum m/e 158 (M$^+$, 90%); 141 (98%, M—OH); 113 (12% M-CO$_2$H); 96 (100%); 71 (52%).

$^1$H-NMR (C$_5$D$_5$N+D$_2$O) 1.2 (m, 2H); 1.48 (s, CH$_3$N—); 1.7 (m, 2H); 1.9 (m, 2H); 2.0 (m. 2H) ppm.

c) 1-Methylpiperidine-4-spiro-5'-(3'-ethylhydantoin), AF160

To a mixture of 1-methylpiperidine-4-spiro-5'-hydantoin (5 g, 27 mmole) and potassium hydroxide (2.08 g, 37 mmole) in 100 ml absolute ethanol ethyl bromide (15 g, 137 mmole) was added. The mixture was heated at 80° C. and samples were taken in 0.5 hr intervals and checked by GLC relative to internal standard (diphenylmethane). The basicity was monitored by titration (HCl 1N) followed by addition of potassium hydroxide (total of 2.1 g). After obtaining the maximum yield (2.5 hrs), the solution was evaporated, water (50 ml) was added and the aqueous solution was extracted with chloroform and chromatographed on silica gel column using chloroform/methanol/aqueous ammonia (80:20:1) as an eluting system. The product was dissolved in ether and precipitated as a hydrochloric acid salt by addition of HCl in isopropanol m.p. 278°–280° C.

Mass spectrum m/e 211(M$^+$, 45%); 71 (100%).

$^1$H-NMR (free base, CDCl$_3$). 1.2(t,J=6Hz, 3H); 1.6–1.7 (m,2H); 1.9–1.95(m,2H; 2.1–2.2(m,2H); 2.34(S,3H); 2.85–2.95(m,2H); 3.5(q, J=6 Hz,2H);.

$^1$H-NMR (HCl salt, D$_2$O) 1.1(t,J=6 Hz,3H); 1.95–2.05 (m,2H); 2.2–2.3(m,2H); 2.85(S,3H); 3.0–3.2(m,2H); 3.4–3.5(m,2H); 3.5(q. J=6 Hz, 2H) ppm. $^{13}$C-NMR (free base, CDCl$_3$) 14.0; 33.0; 33.1; 46.0; 52.8; 59.9; 157.0; 177.0 ppm.

UV (free base. H$_2$O) lambda$_{max}$ 208 nm ($\epsilon$3500).

EXAMPLE 2

1-methylpiperidine-4-spiro-5'-(1'-acetylhydantoin)
AP164 a) AF164A. A mixture of 1-methylpiperidine-4-spiro-5'-hydantoin (3.25 g) in acetic anhydride (50 ml) was heated under reflux for 3 hr. The excess reagent was removed at reduced pressure to leave a solid which was dispersed in ether and filtered to give a white solid (3.75 g) crystallized from methanol-dichloromethane m.p. 250°–254° C. (dec.) AF164A.

$^1$H-NMR (D$_2$O) 1.89(m,2H); 2.44(s,CH$_3$CO—); 2.86(s, CH$_3$N—). 2.98(m,2H); 3.41 (m,2H); 3.67(m,2H) ppm.

$^{13}$C-NMR (D$_2$O, dioxane as internal standard) 26.6 (C$_3$ & C$_5$); 26.9 (CH$_3$CO—); 43.8(CH$_3$N—); 51.4(C$_2$ & C$_6$); $_{62.0}$ (C$_4$); 67.3 (dioxane); 166.0 (C$_2$'); 173.8 (CH$_3$CO—); 189.2 (C$_4$') ppm.

MS m/e 225 (M$^+$); 210; 166; 155; 123; 95; 71 (100%); 70.

b) AF164B. Part of AF164A (1.10 g) was made basic with saturated aqueous Na$_2$CO$_3$ solution and extracted with a mixture of methanol-dichloromethane, the extract was evaporated and the residue extracted again with the same solvent mixture, the extract was filtered and the filtrate evaporated, and the residue (1.0 g) was triturated with acetone giving a white solid AF164B, m.p. 225°–230° C. (dec.) (crystallized from $CH_2Cl_2$—$CH_3OH$—$CH_3CN$).

$^1$H-NMR ($D_2O$) 1.53(m,2H); 2.21(s,$CH_3CO$—); 2.39(s, $CH_3N$—); 2.65–2.80(m, 6H) ppm.

$^{13}$C-NMR ($D_2O$, with dioxane as internal standard) 26.9 ($\underline{C}H_3CO$—); 28.3 ($C_3$ & $C_5$); 45.0 ($CH_3N$—); 50.9 ($C_2$ & $C_6$); 64.9 ($C_4$); 67.3 (dioxane); 168.8 ($C_2$·); 173.6 ($CH_3$ $\underline{C}O$—); 193.9 ($C_4$·) ppm.

MS m/e 225 ($M^+$); 183 ($M^+$—$CH_2$=C=O); 166; 154; 123; 95; 71 (100%)

c) AF164 (HCl salt). An HCl salt of AF164 was prepared by treating a solution of AP164A or AF164B in methanol with HCl dissolved in isopropanol till the pH was acidic (pH 1–2). The salt, AF164 (HCl salt), precipitated after a short time as a white solid m.p. 301°–2° C. (dec.).

$^1$H-NMR ($D_2O$) 2.17 (m, 2H); 2.50 (s, $CH_3CO$—); 2.93 (s, $CH_3N$—); 3.10 (m, 2H); 3.48–3.71 (m, 4H) ppm.

$^{13}$C-NMR ($D_2O$, dioxane as internal standard) 26.7 ($C_3$ & $C_5$); 26.9 ($\underline{C}H_3CO$—); 43.9 ($CH_3N$—); 51.1 ($C_2$ & $C_6$); 61.8 ($C_4$); 67.3 (dioxane); 154.8 ($C_2$·); 173.4 ($CH_3\underline{C}O$—); 176.0 ($C_4$·) ppm. Hydrolysis of AF164

AF164A and AF164B were hydrolyzed by reflux in 0.2N aqueous NaOH (1–2 hr.) to give 1-methylpiperidine-4-spiro-5'-hydantoin, identified by comparison of its TLC and $^1$H-NMR to an authentic sample.

EXAMPLE 3

Piperidine-4-spiro-5'-(3'-ethylhydantoin) AF160 (Des)

To a solution of dried AF160 (2.0 g, 9.5 mmole) in dichloroethane (25 ml., dried over molecular sieves) α-chloroethyl chloroformate (1.0 ml., 9.3 mmole) was added at room temperature and the mixture was heated to 60° C. for 1 h. Dichloroethane was removed in vacuo, the solid obtained was dissolved in 20 ml methanol and the solution was heated for another 30 minutes at 60° C. Then methanol was removed in vacuo and the oily solid obtained was dissolved in aqueous sodium carbonate and washed with ether. The aqueous layer was extracted with chloroform and the extract evaporated to yield a crude oil which was further purified by column chromatography on a silica gel column. Elution with chloroform: methanol: aqueous ammonia (4:1:0.1) gave AF160(Des) (1.12 g., 60% yield) as a white powder mp. 225°–227° C.

MS m/e 197 ($M^+$base peak); 57

$^1$H-NMR ($CDCl_3$) 1.17 (t, J=6 Hz, 3H); 1.65–1.7 (m,2H); 1.85–2.0(m,2H); 2.75–2.85(m,2H); 3.05–3.15(m,2H); 3.5 (q.J=6 Hz, 2H) ppm.

EXAMPLE 4

1-Methylpiperidine-4-spiro-5'-(3'-methylhydantoin) AF178

To a mixture of 1-methylpiperidine-4-spiro-5'-hydantoin (5.0 g., 27.3 mmole) and sodium hydroxide (2.0 g., 50 mmole) in 120 ml methanol, methyl tosylate (11.2 g., 60 mmole) was added. The reaction mixture was stirred overnight at room temperature. methanol was removed by evaporation and the oily residue was dissolved in aqueous potassium carbonate and extracted with chloroform. The organic extract was evaporated and the crude product obtained was further purified by column chromatography on silica and eluting with chloroform/methanol/aq. ammonia (9:1:0.1) to yield 1.2 g. (22%) of a white solid m.p. 229°–231° C.

MS m/e 197 ($M^+$, 30%); 71 (100%).

$^1$H-NMR (free base, $CDCl_3$) 1.6–1.7(m,2H) 2.1–2.3(m, 4H); 2.34(s,3H); 2.85–2.95(m,2H); 3.02(s,3H) ppm.

EXAMPLE 5

Piperidine-4-spiro-5'-(3-methylhydantoin) AF179

The white powdery product which was obtained in the same manner as in Example 3, was dissolved in isopropanol and acidified using hydrochloric acid to yield a white precipitate. m.p. above 320° C. (dec.).

MS m/e 183($M^+$, base peak); 57.

$^1$H-NMR(HCl salt, $D_2O$); 2.0(m,2H); 2.2(m,2H); 2.96(s, 3H); 3.3 (m,2H); 3.6 (m,2H).

EXAMPLE 6

Synthesis of 1-Methylpiperidine-4-spiro-5'-(3'-propargylhydantoin) (AF185)

A suspension of KH (11 g, 0.1 mole; 35% w/w dispersion in mineral oil.) and 1-methylpiperidine-4-spiro-5'-hydantoin (dried over $P_2O_5$, 25 g, 0.13 mole) was stirred at room temperature in dried DMF (500 ml). Propargyl chloride (15 g, 0.2 mole) was added and the reaction mixture was heated to 50° C. for twenty minutes. The mixture was cooled and acidified to pH-3 (with aqueous hydrochloric acid) and the DMF was removed by extraction with a mixture of petroleum ether-ether 1:1 and then with ether. The aqueous phase was basified by sodium carbonate to pH-10 and extracted 2×with chloroform. The chloroform extracts were combined, dried, and evaporated to yield a crude oil (27 g) which was chromatographed on a silicagel column. Elution with chloroform/methanol/ammonia (80:19:1) gave 3.0 g of pure AF185 and several fractions (total 10 g) containing minor impurities. The free base was precipitated as HCl salt; 3.2 g of white non hygroscopic salt was obtained by crystallization from methanol.

$^1$H-NMR ($D_2O$, HCl salt) δ2.0–2.35(m,4H); 2.64(t,1H.J= 3.5 Hz); 2.91(s.$CH_3N$—); 3.1–3.2(m,2H); 3.5–3.7(m,2H); 4.27(bs,2H)ppm.

$^1$H-NMR ($D_2O$ Excess Sodium carbonate) δ1.65–1.75(m, 2H); 1.9–2.05(,2H); 2.25(s,$CH_3N$—); 2.2–2.3(m,4H); 2.8–2.9(m,4H); 4.25(s,2H)ppm. $^1$H-NMR ($CDCl_3$, free base) δ1.85–1.95 (m,4H); 2.2(m,2H); 2.23(t,1H, J=3.5 Hz); 2.4(s,$CH_3N$—); 2.9–2.95(m,2H); 4.3(d.2H, J=3.5 Hz); 6.4 (bs,1H)ppm.

MS m/e 221($M^+$, base peak); 206(M-15); 149.

EXAMPLE 7

1-Methylpiperidine-4-spiro-4'-(2',5'-bis(methylthio)-4'H-imidazole) AF177

To a solution of 1-methylpiperidine-4-spiro-5'-(2',4'-dithiohydantoin) (1.00 g., 4.65 mmole; see Example 11) in methanol (15 ml), NaOH (0.30 g., 7.50 mmole) and then gradually a methyl iodide (1.00 g., 7.04 mole) solution in methanol (3.0 ml.) were added, and the mixture was stirred at room temperature for 1.5 h. NaBr precipitated and was filtered and washed with methanol. The filtrate and washings were combined and the solvent removed; the residue was basified with aqueous $K_2CO_3$ and extracted with ether. The organic extract was dried ($Na_2SO_4$) and the solvent removed to leave a residue which was chromatographed on a column of silica gel. Elution with a 78:18:3:1 solvent mixture of ether/chloroform/methanol\ammonia (aq.) gave AF177. mp 101°–102° C. (465 mg), after crystallization from hexane.

$^1$H-NMR (CDCl$_3$) 1.33 (m, 2H); 1.98 (m, 2H); 2.39 (s, CH$_3$N—); 2.56 (s, CH$_3$S—); 2.59 (s, CH$_3$S—); 2.48–2.64 (m, 2H); 2.82 (m, 2H) ppm.

$^{13}$C-NMR (CDCl$_3$) 14.1 (CH$_3$ S—); 14.2 (CH$_3$ S—); 34.9 (C$_3$ & C$_5$); 46.1 (CH$_3$ N—); 52.2 (C$_2$ & C$_6$); 83.0 (C$_4$); 171.6 (C$_2'$); 203.5 (C$_5'$)ppm.

MS m/e 244 (M$^+$+1); 185; 149; 93; 75

IR (KBr) 2920; 2797; 1535; 1477; 1465; 1452; 1378; 1316; 1286; 1210; 1108; 1054; 1000; 965; 942; 900; 776; 696 cm$^{-1}$.

UV (EtOH) lambda$_{max.}$ 257 nm ($\epsilon$16100).

EXAMPLE 8

1-Methylpiperidine-4-spiro-5'-(3'-ethyl-4'-thiohydantoin) AF182

A sample of 1-methylpiperidine-4-spiro-4'-(1'-ethyl-2'-ethylthio-2'-imidazoline-5'-thione) AF170 (100 mg; see Example 12) was dissolved in 20% HCl (1 ml.) and the solution refluxed for 1.5 h. The reaction mixture war made basic with conc. solution of NaOH to pH14 and then extracted with dichloromethane. The organic extract was dried (Na$_2$SO$_4$) and the solvent evaporated to give 1-methylpiperidine-4-spiro-5'-(3'-ethyl-4'-thiohydantoin) as a white solid (74 mg) crystallized from petroleum ether-dichloromethane m.p. 176°–178° C.

$^1$H-NMR (CDCl$_3$) 1.25 (t, J=7.2 Hz, CH$_3$CH$_2$—); 1.54 (m, 2H); 2.10 (m, 2H); 2.36 (s, CH$_3$ N—); 2.41 (m, 2H); 2.96 (m, 2H); 3.94 (q, J=7.2 Hz, —CH$_2$CH$_3$); 7.23 (NH) ppm.

$^{13}$C-NMR (CDCl$_3$) 11.8 (CH$_3$CH$_2$—); 36.9 (C$_3$ & C$_5$); 37.4 (—CH$_2$CH$_3$); 46.1 (CH$_3$N—); 51.2 (C$_2$ & C$_6$); 68.1 (C$_4$); 157.1 (C$_2'$); 208.1 (C$_4'$) ppm.

MS m/e 227 (M$^+$); 211 (M$^+$—O); 194 (M$^+$—SH); 170 (M$^+$—C$_3$H$_7$N); 71; 70 (100%).

UV (EtOH) lambda$_{max.}$ 280 nm ($\epsilon$13600). 229 nm ($\epsilon$4400).

EXAMPLE 9

1-Methylpiperidine-4-spiro-5'-(4'-methylthio-3'-imidazoline-2'-thione) AF183

When repeating Example 7, but using equivalent amounts of methyl iodide, sodium hydroxide and dithiohydantoin, there was obtained in addition to the bis-(methylthio) derivative AF177, 1-methylpiperidine-4-spiro-5'-(4'-methylthio-3'-imidazoline-2'-thione) AF183, m.p. 218°–220° C. (dec.) (from CH$_2$Cl$_2$-acetone).

$^1$H-NMR (CDCl$_3$) 1.74 (m, 2H); 2.07 (m, 2H); 2.37 (m, 2H); 2.39 (s, CH$_3$N—); 2.69 (s, CH$_3$S—); 2.95 (m, 2H); 10.3 (brs. —NH—) ppm.

MS m/e 229 (M$^+$); 182 (M$^+$—CH$_3$S); 123; 122; 70.

UV (EtOH) lambda$_{max.}$ 312 nm ($\epsilon$12000), 280 nm ($\epsilon$15300).

EXAMPLE 10

1-Methylpiperidine-4-spiro-5'-(3'-ethyl-2',4'-dithiobydantoin) AF163

Powders of 1-methylpiperidine-4-spiro-5'-(3'-ethylhydantoin) (0.570 g) and phosphorus pentasulfide (0.570 g), were intimately mixed and refluxed in tetraline (15 ml) for 2 hr. After allowing the reaction mixture to cool to room temperature, a brown hard precipitate had formed; the tetraline was removed under reduced pressure and the precipitate was disintegrated and washed with petroleum ether. It was made basic with a concentrated aqueous NaOH solution and extracted with dichloromethane. The extract was dried (Na$_2$SO$_4$) and evaporated to give a residue (0.250 g.) which was chromatographed on a column of silica gel (Merck) (60.15 g.). Elution with a 77:18:4:1 mixture of chloroform/ether/methanol/ammonia(aq.) gave pure AF163 (50 mg), crystallized from CH$_2$Cl$_2$-ether m.p. 223°–225° C (dec.).

$^1$H-NMR (CDCl$_3$) 1.27 (t,J=7.2 Hz;CH$_3$CH$_2$—); 1.55–1.67(m; 2H); 2.03–2.19(m,2H); 2.26–2.46(m,2H); 2.36(s,CH$_3$N—); 2.89–3.04(m,2H); 4.27(q,J=7.2 Hz; —CH$_2$CH$_3$); 8.25(brs, —NH—) ppm.

$^{13}$C-NMR (DMSO-d$_6$) 11.6 (CH$_3$CH$_2$—); 36.9(C$_3$&C$_5$); 39.9(—CH$_2$CH$_3$); 45.9(CH$_3$N);49.9(C$_2$&C$_6$);72.9(C$_4$) ;179.8(C$_2'$);207.8(C$_4'$) ppm.

MS m/e 243(M$^+$); 186(M$^+$—C$_3$H$_7$N); 149; 71; 70(100%); 57.

IR (KBr) 3177(NH); 2930; 2778; 1513; 1434;1357; 1231; 1116; 1690; 1070; 1040; 961; 801; 780; 626; 546; 457 cm$^{-1}$.

UV (EtOH) lambda$_{max.}$ 302 nm. ($\epsilon$34200), 226 nm. ($\epsilon$7700). Synthesis of the tartrate salt of AF163

To a solution of AF163 free base (0.735 g., 3.025 mmole) in methylene chloride (15 ml)- methanol (5 ml.) a solution of L(+) tartaric acid (0.214 g., 1.427 mmole) in methanol (2.0 ml.) was added. The mixture was stirred at room temperature for 0.5 hr., then the solvents were evaporated and the residue was suspended in ether-methylene chloride, filtered and washed with the same solvent mixture to give a yellow solid AF163(tartrate) m.p. 221°–225° C. (dec.; 0.923 g., 96% yield).

$^1$H-NMR (D$_2$O) 1.27 (t,J=7.2 Hz, CH$_3$CH$_2$—); 2.08 (m,2H); 2.49(m,2H); 3.01 (s,CH$_3$N—); 3.31 (m,2H); 3.76 (m,2H); 4.26 (q,J=7.2 Hz,—CH$_2$CH$_3$); 4.37 (s,—CHOH) ppm.

EXAMPLE 11

1-methylpiperidine-4-spiro-5'-(2',4'-dithiohydantoin) AF173

A solution of 1-methyl-4-piperidone (29.35 g., 0.260 mole), KCN (26.57 g., 0.408 mole), NH$_4$Cl (21.00 g., 0.393 mole) and CS$_2$ (26 ml.) in ethanol (200 ml.)-water (50 ml.) was heated under reflux 50°–55° C.) for 8 hr. The reaction mixture was left at room temperature overnight and the precipitate obtained was filtered and washed with water and then with ethanol to give a yellow solid (26.3 g.;47.0% yield) m.p.250°–253° C. (dec.), crystallized from methanol m.p.252°–254° C. (dec.).

$^1$H-NMR (DMSO-d$_6$) 1.43–1.56(m,2H); 1.89–2.05(m, 2H); 2.21(s,CH$_3$N—); 2.26–2.40(m,2H); 2.64–2.79(m,2H); 11.14(br.s.,—NH—) ppm.

$^{13}$C-NMR (DMSO-d$_6$) 36.2(C$_3$&C$_5$); 45.5(CH$_3$N—); 49.9(C$_2$&C$_6$); 74.8(C$_4$); 181.5(C$_2'$); 212.0(C$_4'$) ppm. MS m/e 215(M$^+$); 183(M$^+$—S); 182(M$^+$—SH); 181; 158(M$^+$—C$_3$H$_7$N); 123; 102; 77; 71; 70(100%).

IR (KBr) 3130 (NH); 1484; 1449; 1350; 1295; 1231; 1198; 1176; 1145; 1083; 1062; 957; 721; 545; 504 cm$^{-1}$.

UV (0.01N HCl) lambda$_{max.}$ 298 nm. ($\epsilon$32000), 220 nm. ($\epsilon$8000).

EXAMPLE 12

1-methylpiperidine-4-spiro-5'-(3'-ethyl-2',4'-dithiohydantoin) AF163; 1-methylpiperidine-4-spiro-5'-(4'-ethylthio-3'-imidazoline-2'-thione) AF176; 1-methylpiperidine-4-spiro-4'-(1'-ethyl-2'-ethylthio-2'-imidazoline-5'-thione) AF170

To a suspension of 1-methylpiperidine-4-spiro-5'-(2',4'-dithiohydantoin) AF173 (3.30 g.; 15.3 mmole) in dry DMF (30 ml.) NaH (0.760 g. 60% in mineral oil; 19.0 mmole) was added and the mixture stirred at 50° C. for 1.5 hr. A solution of EtBr (1.85 g.; 17.0 mmole) in DMF (6 ml.) was gradually added to the above mixture and it was stirred at 75°–80° for 4 hr. After standing at room temperature overnight, the precipitate formed (NaBr) was filtered and washed with ether. The filtrate and washings were combined and evaporated to give an oil from which a dichloromethane insoluble solid (1.5 g.) was separated, which was found to be starting material (identical NMR and TLC). The residue was chromatographed on a column of silica gel. Elution with a solvent mixture of: ether/chloroform/methanol/ammonia (aq.) 68:27:4:1 gave first 1-methylpiperidine-4-spiro-5'-(3'-ethyl-2',4'-dithiohydantoin) AF163 (0.95 g.), identical to the product obtained before from the reaction of AF160 with $P_2S_5$. The elution was continued to give 1-methylpiperidine-4-spiro-5'-(4'-ethylthio-3'-imidazoline-2'-thione) AF176 (0.15 g.). Crystallized from hexane-$CH_2Cl_2$ m.p. 212°–215° C. (dec.).

$^1$H-NMR ($CDCl_3$) 1.42 (t, J=7.2 Hz, C$\underline{H}_3CH_2$—); 1.73 (m,2H); 2.06 (m,2H); 2.31 (m,2H); 2.38 (s, $CH_3N$—); 2.95 (m 2H); 3.33 (q, J=7.2 Hz, —C$\underline{H}_2$ $CH_3$); 10.0 (br, —NH—) ppm.

$^{13}$C-NMR (DMSO-$d_6$) 14.2 ($\underline{C}H_3CH_2$—); 25.6 (—$\underline{C}H_2CH_3$); 35.0 ($C_3$&$C_5$); 45.8 ($CH_3N$—); 50.5 ($C_2$&$C_6$); 74.3 ($C_4$); 192.1 ($C_{2'}$) 198.1 ($C_{4'}$) ppm.

MS m/e 243 (M$^+$); 182 (M$^+$-EtS,100%); 156(M$^+$-EtSCN); 123; 124; 96; 71; 70; 57.

IR (KBr) 3135 (NH); 2930; 2788; 1476;1463; 1446; 1281; 1257; 1232; 1158; 1141; 1121; 1096; 958; 711; 674; 535 cm$^{-1}$.

UV (EtOH) lambda$_{max.}$ 314 nm. ($\epsilon$5400) inf., 282 nm. ($\epsilon$6700).

Repeating the above reaction with 1.5 molar excess of EtBr over AF173 gave in addition to the above-stated monoethyl derivatives, the diethyl derivative 1-methylpiperidine-4-spiro-4'-(1'-ethyl-2'-ethylthio-2'-imidazoline-5'-thione) AF170 m.p.66°–67° C. (crystallized from hexane).

$^1$H-NMR ($CDCl_3$) 1.24 (t, J=7.2 Hz, C$\underline{H}_3CH_2$—); 1.24 (m,2H); 1.44 (t, J=7.2 Hz, C$\underline{H}_3CH_2$—); 2.27 (m,2H); 2.39 (s, $CH_3N$—); 2.52 (m,2H); 2.81 (m,2H); 3.24 (q, J=7.2 Hz. —C$\underline{H}_2CH_3$); 3.93 (q, J=7.2 Hz, —C$\underline{H}_2CH_3$) ppm.

$^{13}$C-NMR($CDCl_3$) 12.2 ($\underline{C}H_3CH_2$—); 13.9 ($\underline{C}H_3CH_2$—); 25.7 ($\underline{C}H_2CH_3$); 36.8 ($C_3$&$C_5$); 39.0 (—$\underline{C}H_2CH_3$); 46.1 ($CH_3N$—); 51.5 ($C_2$& $C_6$); 82.2 ($C_4$); 158.5 ($C_{2'}$); 216.7 ($C_{5'}$) ppm.

MS m/e 271(M$^+$); 242(M$^+$-Et); 214(M$^+$—$C_3H_7N$); 185; 162; 75; 71; 70(100%); 57.

IR (KBr) 1574 (C=N); 1446; 1372; 1354; 1212; 1071; 1060; 936 cm$^{-1}$.

UV (EtOH) $_{max.}$($\epsilon$) 296(22000); 252(17700) nm. Acid hydrolysis of AF176.

To AF176 (48 mg.), aq. HCl (1 ml.,20%) was added. An immediate odor of a mercaptan was noticed. The solution obtained was stirred at room temp. for 1 hr. then evaporated at 50° C. under reduced pressure, giving as a white solid 1-methylpiperidine-4-spiro-5'-(2'-thiohydantoin) HCl salt (X).

$^1$H-NMR ($D_2O$) 2.10–2.43 (m,4H); 2.94 (s,$CH_3N$—); 3.20 (m,1H); 3.47–3.78 (M,3H) ppm.

MS m/e 199 (M$^+$); 181; 171 (M$^+$—CO); 156 (M$^+$—HNCO); 142 (M$^+$—$C_3H_7N$); 111; 96; 71; 70; 57.

UV ($H_2O$) lambda$_{max.}$ 264 nm. ($\epsilon$20400), 224 nm. ($\epsilon$8600).

EXAMPLE 12

1-methylpiperidine-4-spiro-5'-(2'-thiohydantoin) AF195

(a) A solution of 1-methylpiperidine-4-spiro-5'-(2',4'-dithiohydantoin) (AF173) (10.0 g) in ethanolamine (40 ml)-water (75 ml) was refluxed for 1.75 h. The solvent and excess reagent were removed under reduced pressure. Repeated crystallization of the residue from acetonitrile-dichloromethane; aceton, and ethanol-acetonitrile gave pure 1-methylpiperidine-4-spiro-5'-(2'-thio-4'-(8β-hydroxyethyliminohydantoin) m.p. 230°–231°C. (dec.).

$^1$H-NMR ($D_2O$) 11.74 (m, 2H); 1.94 (m, 2H); 2.26 (s, $CH_3N$—); 2.17–2.34 (m, 2H); 2.92 (m, 2H); 3.54 (t, J=5.4 Hz, —C$\underline{H}_2OH$); 3.74 (t, J=5.4 Hz. =$NCH_2$—) ppm.

$^{13}$C-NMR (DMSO-$d_6$) 33.7 ($C_3$ & $C_5$); 45.4 (—$CH_2$—); 45.9 ($CH_3N$—); 50.6 ($C_2$ & $C_6$); 59.2 (—$CH_2$—); 66.3 ($C_4$); 182.5 (—C=S); 195.0 (—C=N—) ppm.

MS m/e 242 (M$^+$); 224 (M$^+$—$H_2O$); 199; 185; 172 (M$^+$-70); 154 (M$^+$-70-$H_2O$); 71; 70.

UV (0.01N HCl) lambda$_{max.}$ 227 nm ($\epsilon$22200); 242 nm ($\epsilon$10200).

The iminohydantoin derivative (1.40 g) was dissolved in aqueous HCl (5.0 ml, 1:1) and refluxed for 1 hr. The reaction mixture was evaporated under reduced pressure and the residue crystallized from methanol to give 1-methylpiperidine-4-spiro-5'-(2'-thiohydantoin) hydrochloric acid salt (0.756 g), identical to the product obtained from the hydrolysis of AF176 (see Example 12).

(b) A solution of 1-methylpiperidine-4-spiro-5'-(2',4'-dithiohydantoin) (AF173) (10.0 g, 0.0465 mole) and n-butylamine (17.0 g, 0.233 mole) in ethanol (80 ml) was heated under reflux for 1.5 h. The crystalline solid which separated from the cool reaction mixture was filtered, washed with small amount of ethanol, with ether and petroleum ether, to give 1-methylpiperidine-4-spiro-5'-(2'-thio-4'-ethyliminohydantoin) (AF189) (11.1 g, 0.0437 mole) 94% yield. The product was crystallized from dichloromethane-methanol to give needles m.p. 236°–239° C.(dec.).

$^1$H-NMR ($CDCl_3$+$CD_3OD$) 0.94 (t, J=7.2 Hz, C$\underline{H}_3H_2$—); 1.38 (m, 2H); 1.60 (m, 2H); 1.69 (m, 2H); 1.89 (m, 2H); 2.40 (m, 2H); 2.41 (s, $CH_3N$—); 2.91 (m, 2H); 3.47 (t, J=7.2 Hz, —$CH_2$—N=) ppm.

MS m/e 254(M$^+$); 19.7(M$^+$—$C_4H_9$); 184(M$^+$-70); 149; 128; 71; 70; 57($C_4H_9^+$).

The iminohydantoin derivative AF189 (10.45 g) was dissolved in aqueous hydrochloric acid (15.0 ml, 16%) and refluxed for 1 h. The reaction mixture was distilled until only a small amount of liquid remained. Addition of ethanol (50 ml)to the residue and cooling gave a solid which was filtered and washed with a small amount of ethanol and with ether to give 1-methylpiperidine-4-spiro-5'-(2'-thiohydantoin) hydrochloric acid salt (AF195)(8.42 g, 87% yield) m.p.>295° C.(dec.), identical to the product obtained before.

EXAMPLE 14

1-Methylpiperidine-4-spiro-5'-(oxazolidine-2'-thione) AF165

To anhydrous DMSO (10 ml) containing a small amount of KOH powder, 4-aminomethyl-4-hydroxy-1-methylpiperidine (0.595 g., 4.13 mmole) was added with stirring, followed by carbon disulfide (0.340 g, 4.47 mmole). The reaction mixture was heated at 50° C. for 2 h. The solvent was removed in vacuum and the residue was crystallized several times from methanol, acetone and $CH_2Cl_2$ to give a crystalline solid m.p. 190°–195° C. (211 mg).

¹H-NMR (CDCl₃) 1.80–1.98 (m, 2H); 2.03–2.16 (m, 2H); 2.32 (S, CH₃N—); 2.44–2.72 (m, 4H); 3.51 (s-C$\underline{H}_2$N—C=S) ppm.

¹³C-NMR (DMSO-dc) 35.1 (C₃Cl₅); 4.57 (CH₃N—); 51.5 (C₂Cl C₆); 53.1 (—CH₂NH—); 86.4 (C₄); 187.2 (—C=S) ppm.

EXAMPLE 15

N-methylnortrapane-3-spiro-5'-(3'-methylhydantoin) AF167, and N-methylnortropane-3-spiro-5'-(3'-ethylhydantoin), AF168 a) N-methylnortropane-3-spiro-5'-hydantoin

A mixture of tropinone (45 g, 0.32 mole) in ethanol (160 ml), ammonium carbonate (93 g 0.96 mole) in water (400 ml), and KCN (25.8 g, 0.40 mole) in water (84 ml), was heated at 60° C. for 2 hours, and then kept at room temperature for 16 hours. N-methylnortropane-3-spiro-5'-hydantoin (61.33 g, 0.29 mole. 92% yield) separated and was dried in a dessicator: m.p. 330° C.

Mass Spectrum m/e 209 (M⁺)

¹H-NMR (CD₃COOD) 2.1(m,2H,H6=H7(α)) 2.3(m,₂H, H2=H4(β)), 2.4(m, 2H, H2=H4(α)), 2.7 (m, 2H, H6=H7(β)), 2.9 (s, 3H) 3.0 (bs, NH) 4.1 (bs, 2H, H1=H5) ppm.

¹-NMR (DCl, D₂O) 2.3 (m, 4H, H6=H7(α) and H2=H4 (β), 2.5 (m, 2H, H2=H4(α)), 2.7 (m,2H,H6=H7(β)), 2.9(s, 3H), 4.15(bs,2H, H1=H5)ppm.

¹³C-NMR (DCl, D₂O) 25.5 (C6=C7, t), 33.5 (C2=C4, t), 39.7 (CH₃, q), 59.3 (C3–C5', s), 63.0 (CI=C5, d), 159.3 (C2', s), 180.2 (C4',s) ppm.

b) AF167 and AF168

N-methylnortropane-3-spiro-5'-hydantoin (1 eq.) and KOH (1 eq.) were mixed in water at room temperature for a few minutes. Methyl iodide or ethyl bromide (2 eq.) in methanol or ethanol was added dropwise to the aqueous solution. The reaction mixture was extracted with chloroform and dried over magnesium sulfate before evaporation. The products AF167 and AF168 were obtained in about 10% yield.

AF167

¹H-NMR (D₂O) 1.65 (m, 2H, H6=H7(α)), 1.8 (m, 2H, H2=H4(β)), 2.2 (m, 2H, H2=H4(α)), 2.4 (m, 2H, H6=H7 (β)), 2.55 (s, 3H), 2.85 (s, 3H), 3.25 (bs, 2H,H1=H5)ppm.

¹H-NMR (CDCl₃ 1.55 (m, 2H, H6=H7(α)), 1.75 (m, 2H, H2=H4(β)), 2.2 (m, 2H, H2=H4(α)), 2.4 (s,3H), 2.45 (m, 2H, H6=H7(β)), 3.0 (s,CH3), 3.3 (bs, 2H, H1=H5), 6.3 (bs,NH) ppm.

Mass Spectrum m/e 223 (M⁺)

AF168

¹H-NMR (CDCl₃, CD₃OD) 1.1(t, 3H), 1.6 (m, 2H, H6=H7(α)), 1.75 (m, 2H, H2=H4(β)), 2.2(m, 2H,H2=H4(α)), 2.35(s,3H), 2.4(m, 2H, H6=H7(β)), 3.3(bs,2H,H1=H5) 3.55(q,2H)ppm.

¹H-NMR (CDCl₃) 1.2 (t, 3H), 1.6 (m, 2H, H6=H7(α)), 1.75 (m, 2H, H2=H4(β), 2.2 (m, 2H, H2=H4(α)), 2.4 (s,3H), 2.45 (m, 2H, H6=H7(β)), 3.3 (bs, 2H H1=H5), 3.55 (q, 2H), 6.3 (bs,NH) ppm.

¹³C-NMR (CDCl₃, δ) 13(C$\underline{H}_3$CH₂), 25(C6=C7), 35(C2=C4), 40(N—C$\underline{H}_3$), 40.5(N—C$\underline{H}_2$), 59(C3–C5'), 60(C1=C5), 159(C2'), 180(C4')ppm.

Mass Spectrum m/e 237 (M⁺)

EXAMPLE 16

1-methylpiperidine-4-spiro-5'-(3'-ethyloxazolidine-2'-one) AF172 a) 4-acetamidomethyl-4-hydroxy-1-methylpiperidine 4-aminomethyl-4-hydroxy-1-methylpiperidine (2.95 g, 0.02 mole), potassium carbonate (6.5 g, 0.047 mole) and acetic anhydride (8.5 g, 0.08 mole) in methanol were mixed at room temperature for two hours. Sodium hydroxide was added for neutralization and the solution extracted with chloroform. After evaporation, a yellow oil was obtained which was identified as 4-acetamidomethyl-4-hydroxy-1-methylpiperidine (3.4 g, 0.018 mole, 91% yield).

b) 4-ethylaminomethyl-4-hydroxy-1-methylpiperidine 4-acetamidomethyl-4-hydroxy-1-methylpiperidine (3.4 g, 0.018 mole) in dry THF was refluxed in the presence of lithium aluminium hydride (4 g). After 3 days, the mixture was poured into an ice-water bath and filtered through Celite. The solvent was evaporated and after addition of water the solution was extracted with chloroform, and the extract was dried with magnesium sulfate and evaporated to yield 1.03 g (33% yield) crude material. The product thus obtained, 4-ethylaminomethyl-4-hydroxy-1-methylpiperidine, was used without further purification.

c) 1-methylpiperidine-4-spiro-5'-(3'-ethyloxazolidine-2-one)AF172

4-ethylaminomethyl-4-hydroxy-1-methylpiperidine (16.8 g, 0.1 mole) and N,N'-carbonyldiimidazole (32 g, 0.2 mole) were mixed in 400 cc chloroform under nitrogen. Evaporation gave 50 g crude material which was washed thoroughly with hexane, which after evaporation afforded the product, 1-methylpiperidine-4-spiro-5'-(3'-ethyloxazolidine-2-one) AF172, as a yellowish oil (16.8 g, 0.085 mole, 85% yield).

¹H-NMR (CDCl₃) δ1.15(t,3H), 1.8(m,2H), 1.95(m,2H), 2.3(s,3H), 2.55(m,2H), 3.28(s,2H), 3.32(q,2H)ppm.

¹³C-NMR (CDCl₃) 13(C$\underline{H}_3$CH₂), 22(CH₃C$\underline{H}_2$), 37(CH₃CH₂N), 39(CH₂NEt), 52(NCH₂CH₂), 55(C=O). 157.5 (C=O) ppm.

Mass spectrum m/e 198 (M⁺)

EXAMPLE 17

1-methylpiperidine-4-spiro-4'-(3'-ethyloxazolidine-2-one) AF174 a) 4-acetamido-4-hydroxymethyl-1-methylpiperidine 4-amino-4-hydroxymethyl-1-methylpiperidine (2.95 g, 0.02 mole), potassium carbonate (6.5 g, 0.047 mole) and acetic anhydride (8.5 g, 0.08 mole) in methanol were mixed at room temperature for two hours. Sodium hydroxide was added for neutralization and the solution extracted with chloroform. After evaporation the white solid obtained was crystallized with warm acetone affording 4-acetamido-4-hydroxymethyl-1-methylpiperidine (1.67 g, 0.009 mole, 45% yield).

b) 4-ethylamino-4-hydroxymethyl-1-methylpiperidine 4-acetamido-4-hydroxymethyl-1-methylpiperidine (1.6 g, 8.6 mmoles) in dry THF was refluxed in the presence of lithium aluminium hydride (3 g). After 4 hours, the mixture was poured into an ice-water bath and filtered through Celite. The solvent was evaporated and after evaporation of most of the water, the solution was extracted with chloroform, dried with magnesium sulfate and evaporated to yield 1.13 g (77% yield) of quite pure material. The product, 4-ethylamino-4-hydroxymethyl-1-methylpiperidine, so obtained, was used without further purification.

c) 1-methylpiperidine-4-spiro-4'-(3'-ethyloxazolidine-2-one) AF174

4-ethylamino-4-hydroxymethyl-1-methylpiperidine (172 mg, 1 mmole) and N,N'-carbonyldiimidazole (486 mg, 3 mmoles) were mixed in chloroform under nitrogen during 3 hours. Following evaporation, a crude material was obtained which was washed thoroughly with hexane, which after evaporation afforded the product, 1-methylpiperidine-4-spiro-4'-(3'-ethyloxazolidine-2-one) AF174, as a white solid (140 mg, 0.71 mmole, 71% yield).

$^1$H-NMR (CDCl$_3$) δ1.10 (t,3H), 1.6(m,2H), 1.95(m,4H), 2.25(s,3H), 2.85(m,2H), 3.2(q,2H), 4.1(s,2H)ppm.

Mass spectrum m/e 198 (M$^+$)

EXAMPLE 18

2-N-Methylspiro-(1,3-succinimide-4.3')quinuclidine AF133 a) Ethyl (3-quinuclidylidene)-cyanoacetate

A mixture of 3-quinuclidinone (30 g., 0.24 mole), ethyl cyanoacetate (40 g., 0.35 mole), ammonium acetate (3.8 g.), acetic acid (11 g,) and 120 ml benzene, was heated under reflux and water was removed by azeotropic distillation (total of 4 ml water). The benzene solution was cooled, potassium carbonate (30 g.) in 120 ml water was added and the mixture was extracted with toluene (3×500 ml). The toluene extracts were combined, dried and the product was precipitated as a hydrochloric acid salt to yield 63 g. (95% yield) of crude product. TLC ammonium hydroxide (25% in water) 2% v/v in methanol on silica Art 5735 (Merck) R$_f$ 0.67.

The product can be further purified by crystallization in ethanol or isopropanol.

$^1$H-NMR δ(CDCl$_3$-TMS) free base,: 1.29(t,3H,CH$_3$); 4.2 (q,2H,CH$_2$); 1.7–1.9, 2.8–3.2(m,quinuclidine skeleton).

$^{13}$C-NMR δ(CDCl$_3$-TMS): 14(CH$_3$); 62(CH$_2$O); 189 (C=O); 162 (C=N); 115 (C—CN); 100 (C=C); 33.7 (C—H), b) 3-carboethoxy-3-carboethoxymethylquinuclidine Ethyl (3-quinuclidylidene)-cyanoacetate (64 g., 0.24 mole) and potassium cyanide (17 g., 0.26 mole) dissolved in 25 ml water, were dissolved in 125 ml ethanol. The mixture was refluxed for twenty minutes, cooled, decanted from potassium chloride and the remaining potassium chloride was washed with two 50 ml portions of ethanol. The combined alcoholic solution was evaporated and the oily residue was dissolved in 250 ml concentrated hydrochloride acid and refluxed for 24 hr. The solution was then evaporated and the residue washed several times with acetone and dried. The dried solid was refluxed in ethanol saturated with hydrogen chloride for 20 hr. Then ethanol was removed and the residue was basified carefully using sodium carbonate and extracted into chloroform. The chloroform solution was dried, evaporated and the crude diester was further purified by column chromatography using 2% methanol in chloroform as an eluting system.

MS m/e 2.69 (M$^+$); base peak m/e 196 (M—C—OEt).

$^1$H-NMR δ(CDCl$_3$-TMS) 1.2(dt, 6H, CH$_3$); 4.2–4.3 (dt, 4H), CH$_2$O); 1.3–1.6. 2.6–3.1 (m, quinuclidine skeleton).

c) 2-N-Methyl spiro-(1,3-succinimide 4,3') quinualidine (AF133)

3-carboethoxy-3-carboethoxymethylquinuclidine (3.35 g, 12 mmole) was dissolved in 4.5 g methylamine and was heated under pressure at 190° C. (90 hrs). The reaction mixture was cooled, evaporated and the solid residue was purified by column chromatography on silica using 2% methanol in chloroform containing 0.2 ammonia as an eluting system. AF133 was obtained as a white solid, m.p. 94°–96° C. 1.2 g (5.7 mmole).

MS M$^+$ 209.

$^1$H-NMR δ(CDCl$_3$-TMS). 3.4(d,1H)(H$_2$); 2.96(s,3H) (CH$_3$); 2.5(d,1H)(H$_2$); 1.5–1.9(m,quinuclidine skeleton).

EXAMPLE 19

2-N-Ethyl-spiro-(1,3-succinimide 4,3')quinuclidine AF134

The crude 3-carboethoxy-3-carboethoxymethyl- quinuclidine (20 g.) was dissolved in 70% aqueous ethyl amine and heated at 140° C. under pressure for seven hrs. The reaction was monitored by G.C. The crude product was extracted with chloroform which was then dried and evaporated. The oily residue was purified by column chromatography on silica using chloroform/petroleum ether/ethanol/aqueous ammonia 17/13/3/0.4. The free base was precipitated as a hydrochloric acid salt, to yield 6.6 g. of white solid, m.p. 270°–272° C. TLC ammonium hydroxide (25% in water) 2% v/v in methanol on silica Art 5735 Merck R$_f$ 0.47.

MS M+222

$^1$H-NMR δ(CDCl$_3$-TMS) free base: 1.5 (t,3H,CH$_3$); 3.5 (q,2H, N—CH$_2$); 1.6–3.3 (m,quinuclidine skeleton).

EXAMPLE 20

1-Methylpiperidine-4-spiro-5'-(oxazolidine-2',4'-dione) AF169 and 1-Methylpiperidine-4-spiro-5'-(3'-ethyloxazolidine-2',4'-dione) AF180 a) 4-Hydroxy-4-cyano-1-methylpiperidine

To freshly distilled 1-methylpiperidin-4-one (81.72 g, 0.72 mole) in water (200 cc), were added about 100 cc HCl 37% to pH 3. The reaction mixture was cooled in an ice bath and potassium cyanide (49 g, 0.75 mole) in water (200 cc) was added at an adequate rate in order to maintain an internal temperature of about 10° C. The reaction was stirred two hours more after the addition and then filtered. After washing with water and drying, the product, 4-hydroxy-4-cyano-1-methylpiperidine, was obtained in 67% yield as a white powder (67 g, 0.48 mole, mp. 135° C.), $^1$H-NMR (CDCl$_3$) δ1.9 (m,2H), 2.2 (m,2H), 2.4 (s,3H), 2.45 (m,2H), 2.75 (m,2H), 2–3.5 (bm, 1H, OH) ppm.

b) 4-Hydroxy-4-carbamoyl-1-methylpiperidine

The compound 4-hydroxy-4-cyano-1-methylpiperidine (36.4 g, 0.26 mole) was gradually added to sulfuric acid (80 ml), under external cooling. The mixture was maintained at room temperature for 41 hours, then was added to powdered ice (30 g). The resulting solution was neutralized with barium carbonate (376 g) to pH 8–9 and after addition of water the resulting barium sulfate was separated and washed with methanol. The filtrate was concentrated under reduced pressure. The product, 4-hydroxy-4-carbamoyl-1-methylpiperidine (28.16 g, 0.18 mole, 69% yield), crystallized from ethanol as a white solid (mp. 180° C.).

$^1$HNMR (CD$_3$OD) δ1.51 (m,2H), 2.15 (m,2H), 2.25 (s,3H), 2.4 (m,2H), 2.7 (m,2H) ppm.

Mass Spectrum m/e 158 (M$^+$), c) 1-methylpiperidine-4-spiro-5'-(oxazolidine-2',4'-dione) AF169

To a solution of potassium methoxide (9.8 g, 0.14 mole) in dry ethanol (60 ml), was added a solution of 4-hydroxy-4-carboxamide-N-methyl piperidine (27.5 g, 0.17 mole) and diethyl carbonate (26.23 g, 0.22 mole) in ethanol (300 ml). The resulting mixture was refluxed at 80° C. for 60 hours. The reaction mixture was evaporated, the residue was shaken with cold water (70 ml) and neutralized with HCl (2N) to pH 7. The solution was concentrated to half volume and the white precipitate filtered. Trituration with ethanol yielded 1-methylpiperidine-4-spiro-5'-(oxazolidine-2',4'-dione) AF169 (22 g, 0.12 mole) in 70% yield as a white solid (mp. 285° C. (dec)).

$^1$H-NMR (D$_2$O, pH 7) 2.07 (m,2H), 2.27 (m,2H), 2.95 (s,3H), 3.30 (m,2H), 3.60 (m,2H) ppm.

Mass Spectrum (the pH of the compound is 7) m/e 185 and 184 (M$^+$+1 and M$^+$).

d) 1-methylpiperidine-4-spiro-5'-(3'-ethyloxazolidine-2',4'-dione) AF180

To a solution of 1-methylpiperidine-4-spiro-5'-(oxazolidine-2',4'-dione) (2.8 g, 0.015 mole) in dry DMF (100 cc), potassium hydride (65% in oil) was slowly added until the reaction stopped warming up (4.9 g were used). The white suspension was refluxed for one hour and cooled. Ethyl bromide (4.6 g, 0.042 mole) was added dropwise. The reaction warmed up spontaneously. After the mixture has cooled down to room temperature, it was refluxed for two hours. After cooling, a white solid was separated and washed with ethanol. After evaporation of the solvents, the crude product was chromatographed on a silicagel column, using chloroform and methanol as eluent. The fractions containing the product were evaporated. The product was isolated and identified in the free-base form. For practical handling, it was converted to the hydrochloric acid salt with an HCl/ether/ethanol solution from which it precipitated as 1-methylpiperidine-4-spiro-5'-(3'-ethyloxazolidine-2',4'-dione), hydrogen chloride salt (0.746 g, 0.003 mole, 21% yield) mp. 305° C. (dec)).

$^1$H-NMR (CDCl$_3$, free base) δ1.2 (t,3H), 1.75 (m,2H), 2.15 (m,2H), 2.3 (s,3H), 2.32 (m,2H), 2.80 (m,2H), 3.55 (q,2H)ppm.

$^{13}$C-NMR (CDCl$_3$, free base) δ13 (C̱H$_3$CH$_2$), 32 ( C̱H$_2$CH$_3$), 35 (CH$_2$—C̱H$_2$—C, 46 (N—C̱H$_3$), 50 ( C̱H$_2$—N—CH$_3$), 85 (C̱ spiro), 155 (OC̱=O), 175 (C—C̱=O) ppm.

Mass spectrum (free base)) m/e 212 (M$^+$).

EXAMPLE 21

1-Methylpiperidine-4-spiro-4'-(2'-methyl-2'-thiazoline) AF151(S)

a) A mixture of 1-methylpiperidine-4-spiro-4'-(2'-methyl-2'-oxazoline), AF151 (1.85 g 11.0 mmole); phosphorus pentasulfide (1.83 g., 8.23 mmole) and p-toluenesulfonic acid monohydrate (4.20 g., 22.08 mmole) in xylene (70 ml.), was magnetically stirred and refluxed for 3 hr. The solvent was azeotropically distilled and the residue left was made basic with concentrate aqueous solution of NaOH, then extracted with dichloromethane. The organic extract was dried (Na$_2$SO$_4$) and the solvent was removed to give a brown oil (2.10 g.) which was chromatographed on a silica gel column (Kieselgel S. 0.032–0.063 mm., Riedel DeHaen, 70 g.). Elution with a solvent mixture of chloroform (97%)-methanol (3%) which contained 10M ammonia, gave fractions which contained pure AF151(S) (0.90 g.).

b) An intimate mixture of powders of 4-acetamido-4-hydroxymethyl-1-methylpiperidine (8.00 g., 0.043 mole) and phosphorus pentasulfide (6.10 g., 0.0275 mole) was suspended in xylene (120 ml.), magnetically stirred and refluxed for 6 hr. The reaction mixture was left at room temperature overnight and the precipitate obtained was filtered and washed with petroleum ether (40°–60° C.) to give gray powder (13.0 g.). The powder obtained was cooled and made basic with an aqueous concentrated solution of NaOH, then extracted with dichloromethane several times. The combined extracts were dried (Na$_2$SO$_4$) and evaporated. The residue left was extracted with hexane and the hexane removed to give a red oil (3.53 g.) which was distilled to give colorless oil b.p. 60°–68° C. (0.4 mm.), (2.40 g.), which was chromatographed on a column of silica gel 60 (Merck. 100 g.). Elution with a solvent mixture of CCl$_3$:Et$_2$O:MeOH:NH$_4$OH (70:25:4:1) gave pure AF151(S) (1.71 g.).

$^1$H-NMR (CDCl$_3$) 1.65–1.78(m,2H); 1.90–2.04(m,2H); 2.19(s,CH$_3$C=N—); 2.32(s,CH$_3$N—); 2.30–2.43(m,2H); 2.60–2.75(m,2H); 3.11(s,CH$_2$S—) ppm.

$^{13}$C-NMR (CDCl$_3$) 19.9(C̱H$_3$C=N—); 35.8(C$_3$&C$_5$); 43.1(—CH$_2$S—); 45.6(CH$_3$N—); 52.1(C$_2$&C$_6$); 78.5(C$_4$); 161.0(S—C̱=N—) ppm.

MS m/e 184(M$^+$, 100%); (26%); 109(56%); 72(93%); 71(24%).

EXAMPLE 22

1-Methylpiperidine-4-spiro-4'(5)'-(2'-methyl-2'-imidazoline) AF190 a) 4-amino-4-cyano-1-methylpiperidine

1-Methylpiperidin-4-one (33.0 g, 0.292 mole), potassium cyanide (19.5 g, 0.299 mole) and ammonium chloride (16.5 g, 0.308 mole) were suspended in methanol (225 ml) and water (150 ml) and the mixture was stirred at room temperature for 12 days. The precipitate obtained was filtered and the filtrate was evaporated under reduced pressure. To remove water which may have remained in the residue, ethanol was added to it and then azeotropically distilled. Ethanol was added again to the residue, which dissolved in part and left an inorganic solid which was filtered and washed with ethanol. The filtrate and washings were combined and the solvent removed to leave a viscous oil (35.5 g) which showed two spots on TLC (chloroform:methanol:ammonium hydroxide (aq.) 17:2:1-silica gel). It was crystallized from ether to give a solid which was further crystallized from the same solvent to give 4-cyano-4-hydroxy-1-methylpiperidine as crystals m.p. 130°–133° C. The mother liquor when concentrated deposited a second crop of a crystalline solid which was mostly 4-amino-4-cyano-1-methylpiperidine. $^1$H-NMR (CDCl$_3$) 1.72–1.88 (m,2H); 2.01 (m,2H); 2.25–2.37(m,2H); 2.32(s, CH$_3$N—); 2.74–2.83(m,2H) ppm.

MS m/e 139(M$^+$); 112(M$^+$—HCN); 71; 70.

The 4-amino-4-cyano-1-methylpiperidine upon acetylation with acetic anhydride and pyridine gave 4-acetamido-4-cyano-1-methylpiperidine which was crystallized from petroleum ether-dichloramethan m.p. 143°–144° C.

$^1$H-NMR (CDCl$_3$) 1.78–1.96 (m,2H); 2.04 (s,CH$_3$CON—); 2.32 (s,CH$_3$N—); 2.35–2.50 (m,4H); 2.66–2.84 (m,2H); 6.22 (s, —NHCO—) ppm. MS m/e 181 (M$^+$); 122 (M$^+$—CH$_3$CONH$_2$)

IR(CHCl$_3$) 3438, 3303, 2940, 2804; 2242 (C≡N); 1670 (amide) cm$^{-1}$. Acid hydrolysis (H$_2$SO$_4$) of the 4-amino-4-cyano-1-methylpiperidine gave 4-amino-4-carbamoyl-1-methylpiperidine which was crystallized from ethylacetate-dichloromethane m.p. 145°–147° C.

$^1$H-NMR (CDCl$_3$) 1.44 (m,2H); 1.68 (br-NH$_2$); 2.12–2.34 (m,4H); 2.30 (s, CH$_3$N—); 2.70–2.82 (m,2H); 5.47 (br —NH—); 7.39 (br, —NH—) ppm.

MS m/e 158 (M$^+$-1); 157(M$^+$); 140 (M$^+$—NH$_3$, 100%); 113 (M$^+$—CONH$_2$), 96; 71.

b) 4-amino-4-aminomethyl-1-methylpiperidine

A solution of 4-amino-4-cyano-1-methylpiperidine (3.60 g) in dry dimethoxyethane was added to mechanically stirred suspension of LiAlH$_4$ (3.0 g) in dry dimethoxyethane under nitrogen atmosphere, at such a rate that the temperature didn't rise over 50° C. At the end of the addition the mixture was heated under reflux for 6 hr. Excess LiAlH$_4$ was destroyed by adding to the cold (0° C.) stirred reaction mixture, under nitrogen, 4M NaoH (10 ml), water (3 ml), saturated NaOH solution (10 ml) and water (5 ml). The organic solvent was separated and the aqueous phase was extracted several times with hot THF. The organic solvent which was separated and the THF extracts were combined, dried (Na$_2$SO$_4$) and the solvents were removed to give the title compound as a viscous oil (3.17 g) which was purified by distillation b.p. 60°–62° C. (0.8 mm).

$^1$H-NMR (CDCl$_3$) 1,43 (m, 2H); 1.58 (m, 2H); 2.15 (br. —NH$_2$) 2.30 (s, CH$_3$N—); 2.30 (m, 2H); 2.56 (s, —C̱H$_2$NH$_2$); 2.56 (m, 2H) ppm. Acetylation of the diamine obtained gave diacetamide as a solid m.p. 175°–176° C. (from acetonitrile).

$^{1}$H-NMR (CDCl$_3$) 1.74 (m, 2H); 1.96–2.10 (m, 2H); 1.99 (s, CH$_3$CON—); 2.02 (CH$_3$CON—); 2.21 (m, 2H); 2.28 (s, CH$_3$N—); 2.51–2.61 (m, 2H); 3.50 (d, J=5.7 Hz, —CH$_2$NH—); 5.62 (s, —NHCO—); 7.18 (t, —CH$_2$NHCO—) ppm.

MS m/e 227 (M$^+$); 184 (M$^+$—CH$_3$CO); 169 (M$^+$—CH$_3$CONH); 168 (M$^+$—CH$_3$CONH$_2$); 167; 155; 112; 109 (100%); 96; 71; 70.

The diacetamide was also obtained by hydrogenation of 4-amino-4-cyano-1-methylpiperidine with hydrogen (50 psi) with Raney-Ni as catalyst in hot (60° C.) acetic anhydride containing sodium acetate.

c) 1-Methylpiperidine-4-spiro-4'(5)'-(2'-methyl-2'-imidazoline) AF190.

To a solution of b) 4-amino-4-aminomethyl-1-methylpiperidine (0.248 g., 1.734 mmole) in dichloromethane (5 ml), ethyl acetimidate hydrochloride (0.282 g., 2.282 mole) was added and the mixture was stirred at room temperature for 3 hr. The solvent was removed under reduced pressure and the residue was made basic with concentrate aqueous Na$_2$CO$_3$ solution, then extracted with dichloromethane. The extract was dried (Na$_2$CO$_3$) and the solvent was removed to give a colorless oil (191 mg), which was chromatographed on a column of silica gel. Elution with a solvent mixture of methanol:chloroform: 1% ammonium hydroxide (aq.), while increasing the methanol content from 10% to 99% gave pure product AF190 as an oil which solidified upon refrigeration.

$^{1}$H-NMR (CDCl$_3$) 1.57–1.84 (m, 4H); 1.93 (s, CH$_3$C=N—) 2.17–2.33 (m, 2H); 2.29 (s, CH$_3$N—); 2.56 (m, 2H); 3.37 (s, —CH$_2$—N—) ppm.

$^{13}$C-NMR (CDCl$_3$) 15.2 (CH$_3$C=N—); 37.3 (C$_3$ & C$_5$); 46.1 (CH$_3$N—); 52.5 (C$_2$ & C$_6$); 59.7 (C$_4$); 63.7 (—CH$_2$N—); 162.1 (—C=N—) ppm.

MS m/e 167 (M$^+$); 152 (M—CH$_3$); 138; 109(100%); 97; 96; 72; 71; 70.

IR (neat) 3260; 2933; 2852; 2800; 1620 (—C=N—) cm$^{-1}$.

EXAMPLE 23

1-methylpiperidine-4-spiro-4'(5')-[2'-methyl-4'H(5'40H)-imidazol-5'(4')-one] AF230

4-acetamido-4-cyano-1-methylpiperidine (1.03 g) was dissolved in concentrated sulfuric acid (4.0 ml) and left at room temperature for 4 days. The reaction mixture was added to cold water (10 ml) and then barium carbonate was added until no reaction was evident. The precipitated barium sulfate was filtered off, and washed with water and ethanol. The pH of the combined filtrate and washings was adjusted to 13 with concentrated NaOH solution, and the solvents were removed under reduced pressure. The residue was extracted with ethanol, the extract was evaporated, the residue was extracted with dichloromethane, and the extract was evaporated to give an oil (0.75 g), which was chromatographed on a column of silicagel 60 (Merck 0.040–0.063 mm, 32 g). Elution with 1:9 methanol (containing 15% w/w NH$_3$)-chloroform gave pure AF230 (0.185 g), crystallized from dichloromethane-ether m.p. 231°–234° C.

$^{1}$H-NMR (CDCl$_3$) δ1.49(m,2H), 1.97(m,2H), 2.20(s, CH$_3$—), 2.34(s,CH$_3$—) 2.48(m,2H), 2.80(m,2H), 9.83(br. —NH—) ppm.

$^{1}$H-NMR(D$_2$O) δ1.55(m,2H), 1.88(m,2H), 2.22(s,CH$_3$—), 2.29(s,CH$_3$—), 2.33(m,2H), 2.90(m,2H) ppm.

MS m/e 181 (M$^+$); 111 (M$^+$-70); 104; 94; 77; 71(100%); 70.

UV (EtOH) lambda$_{max.}$ 224 nm. (ε4650), 248 nm. (ε2450).

IR (KBr) 3140; 2795; 2540; 1665; 1540 cm$^{-1}$.

Cyclization of 4-acetamido-4-cyano-1-methylpiperidine could also be effected in basic media. Thus, reflux of this compound in 1N ethanolic KOH or in aqueous 1N NaOH also gave AF230. In the latter case, there was also obtained 4-acetamido-4-carbamoyl-1-methylpiperidine, m.p. 207°–208° C. (dec.), crystallized from dichloromethane-methanol.

$^{1}$H-NMR (CDCl$_3$) δ2.05(CH$_3$CO—), 2.08–2.30 (m,6H), 2.28 (CH$_3$N—), 2.63(m,CH$_2$—), 5.40(brs, —NH—), 5.56 (brs, —NH—), 7.04 (brs, —NH—) ppm.

MS m/e 199 (M$^+$); 181 (M$^+$—H$_2$O); 155 (M$^+$—CONH$_2$); 140 (M$^+$—CH$_2$CONH$_2$); 122; 112; 111; 96; 71(100%); 70.

AF230 may exist in the form of tautomers, as indicated by the title.

EXAMPLE 24

1-methylpiperidine-4-spiro-5'-(2'-methyl-2'-oxazoline-4'-one), AF238

(a) 4-acetamidocarbonyl-4-acetoxy-1-methylpiperidine

To a mixture of 4-cyano-4-hydroxy-1-methylpiperidine (2.55 g, 18 mmole) and acetic anhydride (11 ml, 108 mmoles) in a three-necked flask, 5.1 g (2 equivalents) of a 60% solution of perchloric acid (HClO$_4$) was added dropwise. An exothermic reaction occurred, but the temperature dropped after 20 minutes. The solution was stirred for 2 hours, and was left standing overnight at room temperature. The white precipitate was filtered off and washed with ether and petroleum ether. The perchloric acid salt of 4-acetamidocarbonyl-4-acetoxy-1-methylpiperidine was obtained in almost quantitative yield.

$^{1}$H-NMR [perchlorate] (D$_2$O) δ2.2–2.4(m,2H), 2.26(s,3H), 2.27(s,3H), 2.5(m,2H), 2.95(s,3H), 3.32(m,2H), 3.58 (m,H) ppm.

$^{1}$H-NMR [free base] (CDCl$_3$) δ2.05–2.27(m,4H), 2.13(s,3H), 2.28(s,3H), 2.67–2.75(m,4H), 8.4(bs,1H,NH) ppm.

MS m/e 242 (M$^+$); 182, 167, 139, 123(100%), 114, 96, 82, 70, 60.

UV (H$_2$O) lambda$_{max.}$ 206 nm. (ε20400).

IR (KBr) 3380, 3020, 1740, 1670(sh), 1550, 1400, 1380, 1250 cm$^{-1}$.

(b) 1-methylpiperidine-4-spiro-5'-(2'-methyl-2'-oxazoline-4'-one), AF238.

The perchloric acid salt of 4-acetamidocarbonyl-4-acetoxy-1-methylpiperidine (70 mg, 0.25 mmole) in xylene was heated at 172° C. (silicone oil bath temperature), whereupon the white suspended solid turned yellow. A strong smell of acetic acid was perceptible in the course of the reaction. TLC shows total conversion to 1-methylpiperidine-4-spiro-5'-(2'-methyl-2'-oxazoline-4'-one), AF238, which was characterized as the perchloric acid salt.

$^{1}$H-NMR (D$_2$O) δ2.2(m,3H), 2.25(m,2H), 2.45(m,2H), 2.8(s,3H), 3.25(m,2H), 3.5(m,2H) ppm.

MS m/e 182 (M$^+$); 140, 123, 112, 104, 96, 77, 70(100%).

EXAMPLE 25

1-methylpiperidine-4-spiro-5'-(1'-methyl-3'-ethylhydantoin), AF161

To a mixture of AF160 (100 mg, 0.47 mmole) and KH (100 mg, 35% w/w in mineral oil) in 5 ml DMF, was added methyl p-toluenesulfonate (0.4 g, 1 mmole), the solution was stirred 10 minutes at room temperature, and acidified with oxalic acid in ether. The precipitate was dissolved in water, basified, and extracted with petroleum ether, and the extracts were concentrated and chromatographed on silica using 90:10:1 chloroform/methanol/aqueous ammonia. The pure fractions were combined and evaporated, and the residue was dissolved in ether and precipitated as an HCl salt (85 mg, yield 72%).

$^1$H-NMR (free base, CDCl$_3$) δ1.2(t,J=6 Hz,3H), 1.6–1.65 (m,2H), 2.0–2.1(m,2H), 2.39(s,3H), 2.75–2.85(m,4H), 2.86 (s,3H), 3.55(q,J=6 Hz,2H) ppm.

$^1$H-NMR (HCl salt, D$_2$O) δ1.2(t,J=6 Hz,3H), 2.1–2.15(m, 2H), 2.3–2.4(m,2H), 2.95(s,3H), 3.0(s,3H), 3.5(q,J=6 Hz,2H) ppm.

MS m/e 225 (M$^+$ 18%): 71(100%).

EXAMPLE 26

1-methylpiperidine-4-spiro-5'-(1',3'-diethylhydantoin) AF162

To a mixture of 1-methylpiperidine-4-spiro-5'-hydantoin (110 mg, 0.6 mmole) and KH (0.2 g, 35% in mineral oil w/w) in 3 ml DMF, there was added ethyl bromide (0.5 g, 4.6 mmole), the solution was stirred 30 minutes at room temperature, diluted with ether and acidified with excess oxalic acid. The precipitate was dissolved in water, basified, and extracted several times with chloroform, and the extracts were combined, concentrated and chromatographed on silica gel using a gradient of chloroform and 90:10:1 chloroform/methanol/aqueous ammonia, to give pure AF162 (60 mg, yield 42%).

$^1$H-NMR (free base, CDCl$_3$) δ1.2(t,J=6 Hz,6H), 1.65–1.7 (m,2H), 1.96–2.15(m,2H), 2.4(s,3H), 2.5–2.6(m,4H), 3.3(q, J=6 Hz,2H) ppm.

$^1$H-NMR (HCl salt, D$_2$O) δ1.15(t,J=6 Hz,6H), 2.05–2.15 (m,2H), 2.25–2.35(m,2H), 2.9(s,3H), 3.3(q,J=6 Hz,3H) ppm.

$^{13}$C-NMR (HCl salt, D$_2$)O δ14.0; 28.6; 35.0; 44.0; 52.7; 59.2; 157.0; 177.0 ppm.

MS m/e 239 (M$^+$ 75%); 71(100%).

EXAMPLE 27

1-Methylpiperidine-4-spiro-4'-(2'-methylthio-5'-methoxy-4'H-imidazole) AF191

1-Methylpiperidine-4-spiro-4'-(2',5'-dimethylthio-4'H-imidazole) AF177 (0.700 g, 2.881 mmole) and sodium methoxide (0.360 g, 6.667 mmole) were heated under reflux in methanol (15 ml) for 3.5 hours. Evolution of gas was observed. The solvent was removed from the reaction mixture and the residue was extracted with dichloromethane. The organic extract was evaporated to give a solid residue (0.613 g), which was extracted with hot petroleum ether. The solvent was evaporated from the extract to leave a residue (0.263 g), which on crystallization from petroleum ether gave pure AF191, m.p. 84°–85° C.

$^1$H-NMR(CDCl$_3$) 1.40(m,2H); 1.97 (m,2H); 2.36(s, CH$_3$N—); 2.52(s,CH$_3$S—); 2.53(m,2H); 2.70–2.80(m,2H); 4.10(s,CH$_3$O—) ppm.

$^{13}$C-NMR(CDCl$_3$) 13.6(CH$_3$S—); 32.3(C$_3$); 46.2 (CH$_3$N—); 51.9(C$_2$); 57.9(CH$_3$O—); 74.2(C$_4$); 171.6(—N=C—SCH$_3$); 196.0(—N=C—OCH$_3$) ppm.

MS m/e 228M$^+$+1).

EXAMPLE 28

1-Methylpiperidine-4-spiro-4'-(2'-methylthio-5'-amino-4'H-imidazole) AF192

A solution of AF177 (0.411 g) in a reagent (15 ml) prepared by dissolving ammonia in methanol (15% w/w) was stirred 3 days at room temperature. The reaction mixture was evaporated and a fresh 15 ml portion of the reagent was added to the residue, and the reaction was repeated 2× more. Finally, the reaction mixture was evaporated under reduced pressure, and the solid residue was washed with acetone to give AF192, a white solid (0.266 g), m.p.>240° C. (dec.) (from ethanol).

$^1$H-NMR(D$_2$O) 1.48(m,2H); 1.89 (m,2H); 2.29(s, CH$_3$N—); 2.46(m,2H); 2.48(s,CH$_3$S—); 2.86(m,2H) ppm.

MS m/e 212 M$^+$); 142 (M$^+$-70); 70.

EXAMPLE 29

1-Methylpiperidine-4-spiro-4'-(2'-methylthio-5'-amino methyl-4'H-imidazole) AF193 and 1-methylpiperidine-4-spiro-4'-(2',5'-bis(aminomethyl)-4'H-imidazole) AF194

A solution of AF177 (0.338 g) in aqueous methylamine (5.0 ml; 35%) was heated at 80° C. for 2 hours. The water and excess reagent were removed by evaporation under reduced pressure and the residue was chromatographed on a column of silicagel (Merck 60, 0.040–0.06 mm). Elution with an 80:20:1 solvent mixture of chloroform/methanol/aq. ammonia gave AF193 as a white solid (0.061 g). Crystallization from acetonitrile gave m.p. 193°–194° C.

$^1$H-NMR(CDCl$_3$) 1.44(m,2H); 1.85 (m,2H); 2.38(s, CH$_3$N—); 2.52 (s, CH$_3$S—); 2.66(m,2H); 2.81(m,2H); 3.06 (s,CH$_3$NH—); 6.47(—NH—) ppm.

MS m/e 226 M$^+$); 179(M$^+$—CH$_3$S); 170 (M$^+$—CH$_3$NHCN); 169; 156(M$^+$-70).

Elution with an 50:50:1 solvent mixture of chloroform/methanol/aq. ammonia gave AF194 as a white solid (0.130 g). Crystallization from acetonitrile gave m.p. 113°–114° C.

$^1$H-NMR(CDCl$_3$+CD$_3$OD) 1.44(m,2H); 1.81 (m,2H); 2.37(s,CH$_3$N—); 2.57(m,2H); 2.80(m,2H); 2.95(s, CH$_3$NH—); 2.96(m,CH$_3$NH—) ppm.

MS m/e 209 M$^+$); 152; 139(M$^+$-70).

When repeating the above reaction, but using two moles of methylamine for each mole of AP177, the main product obtained was AF193, with only traces of AF194.

EXAMPLE 30

1-Methylpiperidine-4-spiro-4'-(2'-methyl-2'-oxazoline) AF150

(a) 1-Methyl-4-nitromethylpiperidin-4-ol hydrochloride

This starting material was prepared using a slight modification of the method of A. D. Cale (U.S. Pat. No. 4,746, 655, 1988). A mixture of N-methylpiperidinone (142 g, 1.28 mole) and nitromethane (78.1 g., 1.28 mole), was added to a well-stirred solution of sodium ethoxide (1.28 mole), 20% in ethanol, maintaining the internal temperature at 5°–80° C. A white solid precipitates, the stirring is continued for 20 minutes and another 40 minutes at room temperature. The resulting solution was acidified with 500 ml, of 7.2N HCl in isopropyl alcohol. The hydrochloride end the inorganic salts were extracted with CR$_3$OH (3×200 ml) and the solvent removed in vacuo to give the title compound, m.p. 180°–182° C. (non hygroscopic).

m/z: 174 (M$^+$ of free base, 100%), 157 (M—OH, 20%), 127 (M—H—NO$_2$, 25%), 113 (M—NO$_2$—CH$_3$, 40%).

(b) 4-Aminomethyl-1-methylpiperidin-4-ol hydrochloride

Palladium on charcoal (10%, 4 g.) was added portionwise to a solution of 1-methyl-4-nitromethylpiperidin-4-ol (133.5 g) in methanol (1500 ml). The compound was hydrogenated in a Paar at a pressure of 55 psi at room temperature for 48 hours. The solution was cautiously filtered, treated with active charcoal, the solvent removed and the residue was triturated with ethanol (200 ml.) to give the title compound, m.p. 177°–179° C.

m/z: 144(M⁺ of free base, 15%). 127 (M—OH, 25%), 114 (M—CH$_2$NH$_2$, 100%).

(c) 1-Methylpiperidine-4-spiro-4'-(2'-methyl-2'-oxazoline) AF150

A solution of KOH (1.43 g. of 86%) in methanol (50 ml.) was added to a solution of 4-aminomethyl-1-methylpiperidin-4-ol hydrochloride (3.61 g., 0.02 mole) in absolute methanol (50 ml.). After stirring for 10 minutes, a solution of ethyl acetimidate hydrochloride (2.7 g.) in 20 ml. absolute methanol was added, and stirring continued for 30 minutes at room temperature. The solvent was removed, and the residual solid was dissolved in a solution of 2.8 g. Na$_2$CO$_3$ in 50 ml. water, which was concentrated to dryness in vacuo. The white solid was extracted with 2×50 ml. chloroform, treated with active charcoal, dried (Na$_2$SO$_4$) and the solvent removed to afford the title product (62.5% yield), m.p. 45° C. (sublimed at 40° C./0.05 mm Hg), giving a single spot on silica TLC eluted with 2% NH$_3$ in CH$_3$OH, R$_f$=0.4.

m/z: 168 (M⁺ of free base, 100% at 7.5 ev).

$^1$H-NMR (300 MHz, CDCl$_3$): δ3.56 (2H, q, J=1.5 Hz), 2.53 (4H, m), 2.34 (3H, s), 1.96 (3H, t, J=1.5 Hz), 1.82 (4H, m).

Replacement of the KOH used in this Example by the equivalent amount of NaOH or Et$_3$N, gave similar results.

(d) AF150-dibenzoyl-D-tartrate

A hot solution of dibenzoyl-D-tartaric acid (5.4 g., 15 mmole) in 500 ml. toluene was added while stirring to AF150 (5.5 g., 32 mmole) dissolved in 200 ml. dry toluene. The precipitate was allowed to settle and the supernatant liquid was decanted off. The residual solid was washed with 3×100 ml. dry toluene and dried under reduced pressure to afford 8.4 g. (80% yield) of a white slightly hygroscopic solid.

TLC chloroform/alumina (Merck Art 5581) Rf=0.4.

m/z: 168 (M⁺)

$^1$H-NMR (300 MHz, D$_2$O containing 1.5 mg. Na$_2$CO$_3$/0.5 ml. D$_2$O): δ1.95 (s, 6H, CH$_3$—C), 2.35 (s, 6H, CH$_3$—N), 3.5 (s, 4H, CH$_2$), 5.7 (s, 2H), 7.5–8.2 (m, 10H, aromatic hydrogens).

EXAMPLE 31

1-Methylpiperidine-4-spiro-4'-(2'-ethyl-2'-oxazoline) (2'-ethyl analog of AF150)

This compound was prepared similarly to the compound of Example 31, using the equivalent amount of ethyl propionimidate hydrochloride, in place of ethyl acetimidate hydrochloride. The product was obtained as a liquid, b.p. 53°/0.03 mm Hg, in 60.5% yield.

$^1$H-NMR (300 MHz, CDCl$_3$): δ3.52 (2H, t, J=1.5 Hz), 2.47 (4H, m), 2.30 (3H, s), 2.26 [2H, quartet (J=7 Hz), triplets (J=1.5 Hz)], 1.86 (2H, m), 1.72 (2H, m), 1.18 (3H, t),

EXAMPLE 32

1-Methylpiperidine-4-spiro-5'-(2'-methyl-2'-oxazoline) AF151

(a) 1-Methylpiperidine-4-spiro-5'-hydantoin

A mixture of solutions of 1-methylpiperidine-4-one (36.44 g., 0.322 mole) in ethanol (150 ml.), ammonium carbonate (93.0 g., 0.968 mole) in water-(400 ml.) and potassium cyanide (25.8 g., 0.396 mole) in water (82 ml.), was heated at 60° C. for 2.5 hours and then left at room temperature overnight, when 1-methylpiperidine-4-spiro-5'-hydantoin separated. It was filtered off and washed with small amounts of cold water, ethanol and ether, to give a crystalline powder (27.0 g.). Concentration of the filtrate and washings gave a second crop (20.0 g.). The product was crystallized from methanol: m.p. 265°–276° (dec.).

IR (KBr) 3170 (NH); 1700 (C=O) cm$^{-1}$ m/z 183(M⁺, 38%); 71 (100%)

$^1$H-NMR (300 MHz, D$_2$O): δ1.8 (2H), 2.06 (sextet, 2H), 2.49 (S, —CH$_3$), 2.58 (t, 2H), 3.14 (t, 1H), 3.20 (t, 1H).

(b) 4-Amino-1-methylpiperidine-4-carboxylic acid 1-methylpiperidine-4-spiro-5'-hydantoin (9.75 g., 0.0533 mole) and barium hydroxide octahydrate (28.8 g., 0.00913 mole) in water (150 ml.) were heated at 160° C. in an autoclave for three hours. The contents of four such batches were combined and the precipitated barium carbonate was filtered off. The filtrate was neutralized with solid carbon dioxide and the precipitate was removed by filtration. The filtrate was concentrated to a small volume to give 4-amino1-methylpiperidine-4-carboxylic acid (32.0 g., 95% yield), m.p. 275°–280° C. (dec.).

IR (KBr) 3300, 1655, 1580 cm$^{-1}$ m/z 158(M⁺, 90%); 141 (98%, M—OH); 113 (12%, M—CO$_2$H); 96 (100%); 71 (52%)

$^1$H-NMR (300 MHz, C$_5$D$_5$N+D$_2$O): δ1.2 (m, 2H), 1.48 (s, CH$_3$N—), 1.7 (m, 2H), 1.9 (m, 2H), 2.0 (m, 2H).

c) 4-Amino-4-hydroxymethyl-1-methylpiperidine

Lithium aluminum hydride powder (15.62 g., 0.412 mole) in dry tetrahydrofuran (THF) (600 ml.) was heated under reflux for 15 minutes, after which 4-amino-1-methylpiperidine-4-carboxylic acid (31.0 g., 0.196 mole) in the form of a dry powder was added portionwise under nitrogen, with efficient stirring. After the addition was completed, the reaction mixture was heated under reflux for four hours, cooled to 0° C. under nitrogen with efficient stirring, worked up by careful slow addition of water (20 ml.), 15% aqueous NaOH (20 ml.) and again water (10 ml.). The reaction mixture was filtered and the precipitate was extracted with boiling THF (3×15 ml.). The THF filtrate and the extracts were combined and the solvent removed at 25 mm to give a yellow viscous oil (28.0 g., 98.9% yield). IR (neat) 3320 (NH), 3200 (br. OH), 1587 (NH$_2$), 1468, 1448 cm$^{-1}$ m/z 144(M⁺, 15%); 127 (M—OH); 113 (N—CO$_2$H); 96 (100%); 70 (41%).

$^1$H-NMR (300 MHz, CDCl$_3$): δ1.41 (m, 2H), 1.60 (m, 2H), 2.24 (s, CH$_3$—N), 2.29 (m, 2H), 2.48 (m, 2H), 2.50 (br., —NH$_2$), 3.29 (s, —CH$_2$OH).

(d) 1-Methylpiperidine-4-spiro-5'-(2'-methyl-2'-oxazoline) AF151

A mixture of 4-amino-4-hydroxymethyl-1-methylpiperidine (1.80 g.) with acetic acid (20 ml.) and xylene (20 ml.) was azeotropically distilled for 28 hours. The remaining acetic acid and xylene were removed at reduced pressure (25 mm Hg) to leave a residual viscous oil which was basified to pH 11 with an aqueous solution of K$_2$CO$_3$. Extraction with chloroform and evaporation of the extract gave a small amount of residual-brown oil (0.27 g.). The aqueous solution remaining after chloroform extraction was evaporated to remove water, the residual solid was extracted with chloroform and the extract was dried (Na$_2$SO$_4$) and evaporated, to afford as residue a very hygroscopic solid (3.0 g.). TLC showed that the latter gave mainly one spot, which was more polar than the starting aminoalcohol. A portion of the hygroscopic solid, which melted at 150°–160° C., was heated under vacuum, and almost immediately began to distil as a colorless oil at 45° C./0.15 mm Hg. This oil, on keeping in the freezer, formed crystalline needles melting at room temperature. The distillate was the acetic acid salt of the title compound.

IR (neat) 1664 (—C=N); 1565 & 1398 (—$CO_2^-$); 1256 (C—O) cm$^{-1}$ m/z 168(M$^+$ of free base); 109; 70.

$^1$H-NMR (300 MHz, CDCl$_3$): δ1.77 (m, 2H), 1.96 (m, 2H), 1.98 (s, CH$_3$—), 2.0 (s, CH$_3$—), 2.49 (s, CH$_3$—N—), 2.91 (m, 4H), 3.95 (s, —CH$_2$O—), 9.30 (br. s, —CO$_2$H).

$^{13}$C—NMR (300 MHz, CDCl$_3$): δ14.0 (CH$_3$CO$_2$—) 22.9 (CH$_3$C=N—), 35.6 (C$_3$ and C$_5$), 44.4 (CH$_3$N$^+$), 51.1 (C$_2$ and C$_6$), 67.0 (C$_4$), 77.4 (C$_5'$), 164.3 (C—=N), 176.7 (—CO$_2$—).

$^1$H-NMR of free base (300 MHz, CDCl$_3$): δ1.64 (m, 2H), 1.84 (m, 2H), 1.98 (s, CH$_3$—), 2.26 (m, 2H), 2.30 (s, CH$_3$—), 2.69 (m, 2H), 3.94 (s, —CH$_2$—).

EXAMPLE 33

1-Methylpiperidine-4-spiro-5'-(2'-ethyl-2'-oxazoline) (2'-ethyl analog of AF151)

A mixture of 4-amino-4-hydroxymethyl-1-methylpiperidine (3.0 g.) with propionic acid (50 ml.) and xylene (90 ml.) was azeotropically distilled for 5 hours. The residue (7 ml.) was basified to pH 11–12 with an aqueous solution of K$_2$CO$_3$. Extraction with chloroform and evaporation of the extract gave a mixture of non-polar compounds (0.80 g.). The aqueous solution remaining after chloroform extraction was evaporated to remove water, the residual solid was extracted with chloroform and the extract was dried (Na$_2$SO$_4$) and evaporated, to afford as residue a hygroscopic solid (3.6 g.). TLC showed that the latter gave mainly one spot, which was more polar than the starting amino-alcohol (silica gel, solvent 40:58:2 methanol-chloroform-aqueous ammonia). A portion of the hygroscopic solid (1.5 g.) was heated under vacuum, and almost immediately began to distil as a viscous colorless oil at 50° C./0.1 mm Hg. The distillate is the propionic acid salt of the title compound.

m/z 182(M$^+$ of free base, 14%); 167 (5%), 154 (71%), 125 (9%), 109 (100%), 96 (45%), 81 (30%), 74 (57%), 70 (89%), 57 (64%).

$^1$H-NMR (300 MHz, CDCl$_3$): δ1.12 (t, J=7.5 Hz, CH CH$_2$—), 1.17 (t, J=7.6 Hz, CH$_3$CH$_2$—), 1.75 (m, 2H), 2.00 (m, 2H), 2.29 (q, J=7.5, CH$_3$CH$_2$—), 2.30 (q, J=7.6, CH$_3$CH$_2$—), 2.56 (s, CH$_3$N—), 3.02 (m, 2—CH$_2$—), 3.95 (s, —CH$_2$O—), 7.52 (br. —CO$_2$H).

To a stirred solution of the above propionic acid salt (700 mg.) in CHCl$_3$, a saturated aqueous solution of K$_2$CO$_3$ was added until evolution of CO$_2$ had ceased. The mixture was then stirred for 0.5 hour and the phases were separated. The aqueous phase was extracted with CHCl$_3$, the combined separated CHCl$_3$ phase and extracts were dried (Na$_2$SO$_4$), and the solvent was evaporated to afford the title compound (free base) as a residual colorless oil (550 mg.), which showed a single spot on TLC.

$^1$H-NMR (300 MHz, CDCl$_3$): δ1.17 (t, J=7.6 H, CH$_3$CH$_2$—), 1.61 (m, —CH$_2$—), 1.86 (m, —CH$_2$—), 2.18 (m, —CH$_2$—), 2.29(q, J=7.6, CH$_3$CH$_2$—), 2.30(s,CH$_3$N—), 2.71 (m, —CH$_2$—), 3.94 (s, —CH$_2$O—).

m/z 182(M$^+$ 2.5%), 167 (9%), 154 (78%), 125 (17%), 109 (100%), 96 (65%), 81 (54%), 70 (96%), 57 (77%).

An alternative route to compounds such as AF150 and AF151 depends on the cyclodehydration of the appropriate amides. Dehydrating agents such as P$_2$O$_5$, sulfuric acid, BF$_3$-etherate, CaCl$_2$, and molecular sieves, can be used for the above reactions. Corresponding thiazolines instead of oxazolines can be obtained by analogous reactions using P$_2$S$_5$.

EXAMPLE 34

1-Methylpiperidine-4-spiro-5'-(2'-methyl-2'-thiazoline) AF150(S)

(a) 4-Acetamidomethyl-4-hydroxy-1-methylpiperidine

4-Aminomethyl-4-hydroxy-1-methylpiperidine (0.83 g., 5.7 mmole) was dissolved in 10 ml. CHCl$_3$, and acetic anhydride (0.58 g., 5.7 mmole) was added. The reaction mixture warmed spontaneously to 40°–50° C. After 30 minutes, the solvent was evaporated and the crude residue was chromatographed on a silica gel column (Merck 7734), using as eluent 33:67 2% aq. ammonia-methanol.

m/z 186 (M$^+$)

$^1$H-NMR (300 MHz, CDCl$_3$): δ1.60 (multiplet, 4H, H3 and H4), 2.01 (singlet, 3H, CH$_3$—C), 2.29 (singlet, 3H, CH$_3$—N), 2.38 (multiplet, 2H, H1), 2.55 (multiplet, 2H, H2), 2.98 (multiplet, 1H, NH), 3.26 (doublet, 2H, H5) ppm.

$^1$H-NMR (300 MHz, D$_2$O): δ1.42 (multiplet, 4H, H3 and H4), 1.81 (singlet, 3H, CH$_3$—C), 2.08 (singlet, 3H, CH$_3$—N), 2.27 (multiplet, 2H, H1), 2.46 (multiplet, 2H, H2), 3.03 (singlet, 2H, H) ppm.

The impurity gives a peak at 3.44 ppm.

(b) 1-Methylpiperidine-4-spiro-5'-(2'-methyl-2'-thiazoline) AF150(S)

A mixture of 4-acetamidomethyl-4-hydroxy-1-methylpiperidine (6.5 g., 35 mmole) with phosphorus pentasulfide (10 g., 22 mole) was heated at 220° C. for 30 minutes, cooled, and dissolved in 30 ml. concentrated aq. HCl. The solution was mixed with 100 ml. cold concentrated aq. NaOH, extracted with 2×100 ml. CHCl$_3$, and the combined extracts were dried and evaporated to afford 5 g. of a black oily residue, which was purified by distillation at 75° C./1 mm Hg to yield 1.8 g. clear liquid.

m/z: 184 (M$^+$)

$^1$H-NMR (300 MHz, CDCl$_3$): δ1.8–2.0 (m, 4H), 2.17 (t, 3H, CH$_3$—C), 2.2 (s, 3H, CH$_3$—N), 3.9 (q, 2H, CH$_2$-thiazoline ring).

EXAMPLE 35

1-Methylpiperidine-4-spiro-5'-(2'-thione-3'-ethylhydantoin) AF181

To a solution of 4-amino-1-methylpiperidine-4-carboxylic acid (1.78 g, 0.0113 mole) and sodium hydroxide (0.47 g, 0.0118 mole) in water (3.0 ml), ethyl isothiocyanate (1.00 g, 0.0111 mole) was added and the mixture heated under reflux for 6.5 h. The reaction mixture was acidified to pH 1 with concentrated hydrochloric acid and the reflux continued for an additional 1.5 h. On standing at room temperature the reaction mixture deposited a solid (0.61 g) which was crystallized from methanol to give crystals (83 mg) m.p.>260° C. The $^1$H-NMR spectrum of this solid shows that it is the hydrochloric acid-salt of AF181.

$^1$H-NMR (D$_2$O) δ1.16(t, j=7.2 Hz, CH$_3$CH$_2$—); 2.0–2.4 (m,4H); 2.94(s, CH$_3$N—); 3.20(m, 1H); 3.4–3.74(m, 3H); 3.80(q, J=7.2 Hz, CH$_3$CH$_2$—) ppm.

The mother liquors left after the isolation and crystallization of the above salt were combined, made basic to pH 13 with concentrated aqueous sodium hydroxide solution, then extracted with dichloromethane. The extract was dried (Na$_2$CO$_3$) and evaporated to give a yellowish solid which was chromatographed on a silica gel column (Merck 60 0.04–0.06 mm). Elution with chloroform/methanol/ammonium hydroxide (aq.) 96:3:1 gave first 1,3-diethyl-2-thiourea (0.287 g) m.p. 76°–78° C. (crystals from ether) and afterwards 8-methyl-3-ethyl-1,3,8-triazaspiro[4.5]decane-4-one-2-thione (AF181) (135 mg) as the free base. It was crystallized from ether-dichloromethane to give needles m.p. 180° C.

$^1$H-NMR (CDCl$_3$) δ1.24(t, J=7.2 Hz. CH$_3$CH$_2$—); 1.69 (m,2H); 2.05–2.30(m,4H); 2.35(s, CH$_3$N—); 2.90(m,2H); 3.87(q, J=7.2 Hz, CH$_3$CH$_2$—) ppm.

MS m/e 227(M$^+$); 71; 70.

EXAMPLE 36

1-Methylpiperidine-4-spiro-5'-(2'-thione-3'-t-butylhydantoin) AF184

A mixture of 4-amino-1-methylpiperidine-4-carboxylic acid (1.80 g, 0.0114 mole) and t-butylisothiocyanate (1.00 g, 0.0087 mole) in water (3.0 ml) was heated at 80° C. for 5 h. As the reaction according to TLC was not completed, ethanol was added (4.0 ml) and the reaction mixture heated under reflux for an additional 1 h. It was acidified to pH 1 with concentrated hydrochloric acid and the reflux continued for an additional 1 h. After standing overnight at room temperature a precipitate separated and it was filtered to give the starting amino acid (0.60 g). The mother liquor was evaporated and the residue made basic with concentrated aqueous sodium hydroxide solution, then extracted with dichloromethane. The organic extract was dried (Na$_2$SO$_4$) and the solvent removed to give a crystalline solid (0.101 g), needles from ether-dichloromethane, m.p. 200°–201° C.

$^1$H-NMR (CDCl$_3$) δ1.63(m, 2H); 1.81[s, (CH$_3$)$_3$C—]; 2.00–2.21(m, 4H); 2.33(s, CH$_3$N—); 2.87(m, 2H); 7.82(bs, —NH—) ppm.

MS m/e 255(M$^+$); 199(M$^+$—C4H8); 96; 71; 70; 57.

EXAMPLE 37

1-Methylpiperidine-4-spiro-5'-(3'-t-butylhydantoin) AF213

The title compound was synthesized in a similar way as AF181. The product was obtained as the hydrochloric acid salt of 1-methylpiperidine-4-spiro-5'-(3'-t-butylhydantoin) AF213 and was crystallized from methanol, m.p. 300°–303° C. (dec.).

$^1$H-NMR (D$_2$O) δ1.55[s, (CH$_3$)$_3$C—]; 2.01(m, 2H); 2.22 (m, 2H); 2.92(s, CH$_3$N—); 2.97–3.5(m, 2H); 3.62(m, 2H) ppm.

The free base obtained was crystallized from ether-dichloromethane and had a m.p. 221°–223° C.

$^1$H-NMR (CDCl$_3$) δ1.57(m, 2H); 1.60[s, (CH$_3$)$_3$C—]; 2.01–2.18(m, 4H); 2.31(s, CH$_3$N—); 2.88(m,2H); 4.77(bs, —NH—) ppm.

$^{13}$C-NMR (CDCl$_3$) δ28.6[(CH$_3$)$_3$C—]; 33.5(C6&C10); 46.2(CHO$_3$N—); 51.0(C7&C9); 57.5 and 58.1[C5 & (CH$_3$)$_3$C—]; 158.4(C2); 177.4(C4) ppm.

MS m/e 239(M$^+$); 237; 224(M$^+$—CH$_3$); 194; 181; 155; 110; 104; 71; 56; 43.

EXAMPLE 38

1-Propargylpiperidine-4-spiro-5'-(3'-ethylhydantoin) AF196

A mixture of piperidine-4-spiro-5'-(3'-ethylhydantoin) (AF160)DES (40.9 mg, 0.21 mmole) and propargyl bromide (24.7 mg, 0.21 mmole, 80% w/w in toluene) was stirred in methanol (1.0 ml) at 25° C. for 24 h. The methanol was removed by a stream of nitrogen, and the resultant mass was made basic by aqueous sodium carbonate and extracted with chloroform. The chloroform extracts were evaporated and the residue was purified on a preparative silica-gel plate (chloroform/methanol/aqueous ammonia 90/10/1) and precipitated by an excess of oxalic acid to yield a crystalline solid (29 mg).

$^1$H-NMR (D$_2$O, oxalic acid salt) δ1.12(t, 3H,J=6 Hz,CH$_3$CH$_2$—); 2.1–2.35(m, 6H); 3.12(t, 1H,J=3.5 Hz); 3.5(q, J=6 Hz,CH$_3$CH$_2$—); 3.7– 3.85(m, 2H); 4.12(d, J=3.5 Hz) ppm.

MS m/e 235(M$^+$); 196(M$^+$—C$_3$H$_3$); 95; 80; 67; 56.

EXAMPLE 39

1-Methylpiperidine-4-spiro-5'-[3'-(4-pyrrolidino-2-butynyl)hydantoin] AF197

A mixture of 1-methylpiperidine-4-spiro-5'-(3'-propargylhydantoin) (AF185) (204 mg, 0.92 mmole), pyrrolidine (88 mg, 1.23 mmole), paraformaldehyde (52 mg,1.7 mmole) and cuprous chloride (4.2 mg) was stirred in dioxane (10 ml) for 70 hrs at room temperature. The dioxane was removed by a stream of nitrogen, the resultant mass was made basic by aqueous potassium carbonate and extracted with chloroform. The chloroform extracts were evaporated and 50% by weight of the residue was purified on a preparative silica-gel plate (chloroform/methanol/ether/aqueous ammonia 150/20/100/6), crystallized twice from ether to yield a crystalline solid (25 mg).

$^1$H-NMR (CDCl$_3$, free base) δ1.12 (m); 2.1–2.2(m); 2.35 (s,3H); 2.6(m); 2.9–2.95(m); 3.4(t, 2H,J=3.5 Hz); 4.15(t,2H, J=3.5 Hz); 5.9(bs,1H) ppm.

Ms m/e 304(M$^+$); 234(M$^+$—C$_4$H$_8$N); 71(C$_4$H$_9$N$^+$).

EXAMPLE 40

1-methylpiperidine-4-spiro-5'-(2'-methyl-1',4'-oxazolidine-3'-one) AF260

A mixture of 1-methyl-4-piperidone (5.0 g, 44.2 mmole), ethyl-(s)-lactate (5.75 g, 48.8 mmole), ammonium carbonate (6.38 g) and p-toluenesulfonic acid (2.1 g) in toluene (100 ml) was sealed in a stainless steel pressure vessel and heated at 107° C. with stirring for 24 h. The toluene was removed from the reaction mixture by distillation and the residue chromatographed on a column of silica gel (Merck 60). Elution with a solvent mixture of chloroform/methanol/ammonia 92:7:1 gave a fraction (1.01 g) which was further separated by chromatography on a silica gel column. Elution with a solvent mixture of chloroform/ether/methanol/ammonium hydroxide 541:37:7:2 gave a crude product (0.441 g), which was crystallized from ether-petroleum ether and then from toluene to give 1-methylpiperidine-4-spiro-5'-(2'-methyl-1',4'-oxazolidine-3'-one) (AF260) as needles (85 mg) m.p. 148°–150° C.

$^1$H-NMR (CDCl$_3$) δ1.42(d, j=6.6 Hz, CH$_3$CH—); 1.85 (m, 4H); 2.31(s, CH$_3$N—); 2.52(m, 4H); 4.40(q, j=6.6 Hz, CH$_3$CH—); 7.64(bs, —NH—) ppm.

MS m/e 184(M$^+$); 156, 126, 114, 84; 71; 70; 43(100%).

EXAMPLE 41

1-Methylpiperidine-4-spiro-5'-(2'-methyl-1',4'-thiazolidine-3'-one) AF261; and Example 42: 1-Methylpiperidine-4-spiro-5'-(2',4'-dimethyl-1',4'-thiazolidine-3'-one) AF266 a) A mixture of 1-methyl-4-piperidone (5.65 g, 0.050 mole), thiolactic acid (6.37 g, 0.060 mole) and ammonium carbonate (7.20 g) in benzene (150 ml) was heated under reflux for 16 h, when a solid sublimed (ammonium carbonate) which condensed outside the reaction flask. From time to time this solid was added again to the reaction flask together with an additional portion of new ammonium carbonate (total 6.2 g). Finally, the benzene was removed by distillation and the residue washed with ether to give an ether soluble material (0.76 g) and an insoluble one (12.9 g), which was dissolved in a small amount of methanol and made basic with a solution of ammonia in methanol. It was evaporated and chromatographed on a column of silica gel (Merck 60). Elution with a solvent mixture of chloroform/methanol/ammonia 89:10:1 gave a fraction (0.61 g) which was identified as 1-methylpiperidine-4-spiro-5'-(2',4'-dimethyl-1',4'-thiazolidine-3'-one) AF266. It is a low melting point hygroscopic solid.

$^1$H-NMR (CDCl$_3$) δ1.53(d, j=7 Hz, CH$_3$CH—); 1.69(m, 2H); 2.16–2.44(m, 4H); 2.32(s, CH$_3$N—); 2.87(m, 2H); 2.90(s, CH$_3$NCO—); 3.79(q, j=7 Hz, CH$_3$CH—) ppm. $^{13}$C-NMR (CDCl$_3$) δ19.7(CH$_3$CH—); 27.2(CH$_3$NCO—); 36.0 and 37.3(C6&C10); 39.7(C2); 45.3(CH$_3$N—); 51.8 and 52.2 (C7&C9); 68.5(C5); 172.8(C3) ppm.

The hydrochloric acid salt of AF266 was obtained by treating a solution of the free base in ether with a solution of hydrochloric acid in isopropyl alcohol to give a hygroscopic solid which was crystallized from isopropyl alcohol m.p. 238°–240° C. (dec.). $^1$H-NMR (D$_2$O, HCl salt) δ1.48(d, J=7.2 Hz, CH$_3$CH—); 2.05(m, 2H); 2.57(m, 2H); 2.89 and 2.91(2s, CH$_3$N$^+$— and CH$_3$NCO—); 3.31(m, 2H); 3.61(m, 2H); 4.04(q, j=7.2 Hz, CH$_3$CH—) ppm.

MS m/e 214(M$^+$); 181; 156; 125; 124; 96; 71; 70; 57(100%); 43.

Continuing the elution of the column with a solvent mixture of chloroform/methanol/ammonia 85:14:1 gave a fraction (3.50 g) which was crystallized from ether-dichloromethane to give 1-methylpiperidine-4-spiro-5'-(2'-methyl-1',4'-thiazolidine-3'-one) AF261 as needles (1.83 g) m.p. 133°–1340° C.

$^1$H-NMR (CDCl$_3$) δ1.53(d, J=7 Hz, CH$_3$CH—); 1.9–2.20 (m, 4H); 2.20–2.42(m, 2H); 2.30(s, CH$_3$N—); 2.68(m, 2H); 3.85(q, J=7 Hz, CH$_3$CH—); 6.90(bs, —NH—) ppm.

$^{13}$C-NMR (CDCl$_3$) δ19.9(CH$_3$CH—); 41.0 and 41.3 (C6&C10); 41.3(C2); 45.7(CH$_3$N—); 52.5 and 52.8 (C7&C9); 63.6(C5); 176.3(C3) ppm.

MS m/e 200(M$^+$); 167, 140(M$^+$—CH$_3$CHS—); 91; 71; 70; 69; 57.

The hydrochloric acid salt of AF261 was obtained by treating a solution of the free base in ether with a solution of hydrochloric acid in isopropyl alcohol, m.p. 285°–287° C.

$^1$H-NMR (HCl salt, in D$_2$O) δ1.50(d, j=7.1 Hz, CH$_3$CH—); 2.17–2.44(m, 4H); 2.89(s, CH$_3$N—); 3.24(m, 2H); 3.59 (m, 2H); 4.10(q, J=7.1 Hz, CH$_3$CH—) ppm.

b) A mixture of 1-methyl-4-piperidone (5.65 g, 0.050 mole), thiolactic acid (6.37 g, 0.060 mole) and ammonium carbonate (7.20 g) in benzene (100 ml) was sealed in a stainless steel pressure vessel and heated overnight at 95° C. with magnetic stirring. The solvent was removed from the reaction mixture and the residue dissolved in a small amount of methanol and loaded on a dry column of silica gel (Merck 60, 200 g). Elution with a solvent mixture of chloroform/methanol/ammonia(aq.) 94:5:1 gave first AF266 (0.71 g) and afterwards AF261 (3.02 g).

c) A mixture of 1-methyl-4-piperidone (2.50 g, 22.1 mole), thiolactic acid (2.81 g, 26.5 mmole) and methylamine (0.90 g, 29.0 mmole) in toluene (60 ml) was sealed in a stainless steel pressure vessel and heated at 96° C. with stirring for 24 h. The reaction mixture is a viscous oil from which separated a precipitate and a toluene solution. The solution was separated and the solvent removed by distillation. The residue (1.68 g) was distilled at reduced pressure to give pure 1-methylpiperidine-4-spiro-5'-(2',4'dimethyl-1',4'-thiazolidine-3'-one)AF266 b.p.100° C. (0.35 mm Hg) as a solid (1.02 g) m.p. 43°–45° C.

EXAMPLE 43

1-Methylpiperidine-4-spiro-5'-(2'-ethyl-1',4'-thiazolidine-3'-one) AF267, and Example 44: 1-Methylpiperidine-4-spiro-5'-(2'-ethyl-4-methyl-1',4'-thiazolidine-3'-one) AF272

The title compound AF267 was prepared as described for the preparation of AF261, using 2-mercaptobutyric acid instead 2-mercaptopropionic acid (thiolactic acid). It was crystallized from acetone m.p. 140°–141° C.

$^1$H-NMR (CDCl$_3$) δ1.02(t, j=7.2 Hz, CH$_3$CH$_2$—); 1.75 and 2.06(m, CH$_3$CH$_2$—); 1.98(m, 4H); 2.30(s, CH$_3$N—); 2.32(m, 2H); 2.67(m, 2H); 3.81(dd, —CHS—); 6.35(bs, —NH—) ppm.

$^{13}$C-NMR (CDCl$_3$) δ11.4(CH$_3$CH$_2$—); 27.1(CH$_3$CH$_2$—); 41.5(C6&C10); 45.8(CH$_3$N—); 49.0(C2); 52.7 and 52.9 (C7&C9); 63.7(C5); 175.5(C3) ppm.

MS m/e 214(M$^+$); 181; 140; 71; 57.

The hydrochloric acid salt of AF267 had m.p. 267°–269° C. (dec.). As a by product 1-Methylpiperidina-4-spiro-5'-(2'-ethyl-4'-methyl-1',4'-thiazolidine-3'-one)AF272 was obtained as a viscous oil.

$^1$H-NMR (CDCl$_3$) δ1.00(t, j=7.4 Hz, CH$_3$CH—); 1.67(m, 2H); 1.58–1.78(m) and 2.13(m) (CH$_3$CH$_2$—); 2.20–2.42(m, 4H); 2.32(s, CH$_3$N); 2.89(s, CH$_3$NCO—); 2.90(m, 2H); 3.76(dd, j1=3.6 Hz, j2=9.0 Hz. CH$_3$CH$_2$CH—) ppm.

MS m/e 228(M$^+$); 195; 170; 138; 125; 96; 71; 70; 57.

EXAMPLE 45

1-Methylpiperidine-4-spiro-5'-(1'-sulfoxy-4'-aza-2'-methyl-3'-one) AF262

A mixture of 1-Methylpiperidine-4-spiro-5'-(2'-methyl-1', 4'-thiazolidine-3'-one) (AF261 ) (48.4 mg, 0.24 mmole) in 2.0 ml acetic acid and 0.5 ml aqueous hydrogen peroxide (32%) was stirred at 25° C. for twenty minutes. The reaction mixture was acidified by addition of excess of hydrochloric acid and diluted with 20 ml petroleum-ether/ether 4/1. The precipitate was dissolved in aqueous sodium carbonate and the solution was extracted with chloroform. The chloroform extract was dried, evaporated and the resultant mass was chromatographed on a preparative silica-gel plate (chloroform/methanol/aqueous-ammonia 80/20/1) to yield 3.3 mg of oil, which was precipitated from ether by oxalic acid to yield one isomer (>90% purity) of a crystalline solid.

$^1$H-NMR (CDCl$_3$, free base) δ1.52(d, 3H,J=6 Hz)CH$_3$CH—; 1.85–2.7[m, 8H]; 2.36(s,3H)CH$_3$—N; 3.55 (q,J=6 Hz)CH$_3$CH—); 7.0(bs,1H) ppm.

Ms m/e 216(M$^+$); 199; 167; 149; 125; 111.

EXAMPLE 46

Piperidine-4-spiro-5'-(2'-methyl-1',4'-thiazolidine-3'-one) AF263

A mixture of 1-methylpiperidine-4-spiro-5-(2'-methyl-1', 4'-thiazolidine-3'-one) (AF261 ) (250 mg, 1.25 mmole) and α-chloroethyl chloroformate (0.15 ml, 1.4 mmole) was heated in 5 ml dichloroethane at 60° C. for ninety minutes.

The dichloroethane was removed under a stream of nitrogen and the oily residue was dissolved in methanol and heated at 60° C. for one hour. The methanol was evaporated, the residue was dissolved in aqueous sodium carbonate, extracted with chloroform and separated on a preparative silica-gel plate (chloroform/methanol/aqueous ammonia 80/20/1) to yield 20 mg free base that was precipitated as a crystalline oxalic acid salt.

$^1$H-NMR (D$_2$O, oxalic acid salt) δ1.51(d, 3H,J=6 Hz, CH$_3$CH—); 2.2–2.35 (m, 4H); 3.1–3.6(m,4H); 4.1(q,J=6 Hz,CH$_3$CH—) ppm.

MS m/e 186(M$^{30}$); 153; 126; 57.

EXAMPLE 47

1-Methylpiperidine-4-spiro-5'-(3'-methyl-1',4'-oxathiolane-2'-one) AF265

A solution of 1-methyl piperidone (11.3 g 0.1 mole), thiolactic acid (15 ml) and p-toluenesulfonic acid in acetonitrile was refluxed for 24 h and followed by TLC (Silica-20% methanol in chloroform). Then, the solution was evaporated dissolved in chloroform and washed with a solution of sodium bicarbonate and then with water. The organic phase was dried on sodium sulfate and evaporated. The product was purified on a silicagel column (Merck 60). Elution with a solvent mixture of chloroform/methanol/ ammonia gave 10.27 g of an oil which crystallize on standing at room temperature. It was identified as 1-methylpiperidine-4-spiro-5'-(3'-methyl-1',4'-oxathiolane-2'-one) (AF265) mp. 92° C.

$^1$H-NMR (CDCl$_3$) δ11.6(d, 3H)), 1.98–2.12 (m,2H), 2.13–2.3 (m,2H 2.34–2.55 (m,2H), 2.55–2.72 (m,2H), 2.30 (s,2H), 4.06(q, 1H) ppm.

$^{13}$C-NMR (CDCl$_3$) δ18 (CH$_3$CH, quartet), 39 (C6 and C10, one triplet), 40 (CH$_3$CH, doublet), 45.5 (CH$_3$—N, quartet), 51.8 and 52 (C7 and C9, two distinct triplets), 87(C5, singlet), 175 (C=O) ppm.

MS m/e 201 (M$^+$)

The compound AF265 (free base) was dissolved in acetone and oxalic acid was added (one mole for two moles of free base). A white solid precipitated after a few seconds. It was filtered, washed with acetone, chloroform and ether, and dried in a dessicator. It was identified as the oxalic acid salt of AP265. The stability of this salt is still under investigation. Some of it decomposed in water, possibly by hydrolysis of the lactone and the signals due to the product obtained by ring opening can be seen in the $^{13}$C-NMR spectrum which was recorded in D$_2$O for at least 3 hours of scan accumulation. In the $^1$H-NMR spectrum measured immediately after dissolution, only the spiro compound is visible. It was found that a solution of AF265 in water shows after one week about one third of ring opening, m.p. 120° C.

$^1$H-NMR (D$_2$O) δ1.55 (d, 3H), 2.3–2.6 (m,4H), 2.9(s,3H), 3.2–3.4 (m,2H), 3.4–3.7(m,2H), 4.4 (q,1H) ppm.

$^{13}$C-NMR (D$_2$O) δ17.5 (CH$_3$CH), 36 and 36.5 (C6 and C10), 41.5 (CH$_3$CH), 43 (CH$_3$—N), 51 (C7 and C9), 84(C5), 167 (CO of the oxalic acid), 177 (C=O) ppm.

EXAMPLE 48

Piperidine-4-spiro-5'-(3'-methyl-1',4'-oxathiolane-2'-one) AF269

The starting material 1-methylpiperidine-4-spiro-5'-(3'-methyl-1',4'-oxathiolane-2'-one) (AF265) (80 mg), was dissolved in benzene and the solution evaporated to dryness to ensure that no moisture is present. Under a nitrogen atmosphere. dichloromethane dried on molecular sieve was added (about 4 ml) followed by 1-chloroethyl chloroformate (56 mg). The reaction mixture was heated to 100° C. for about one hour then evaporated. Chloroform was added and a white solid filtered off, washed with chloroform and carbon tetrachloride, then dried. The product was identified as the hydrochloric acid salt of piperidine-4-spiro-5'-(3'-methyl-1',4'-oxathiolane-2-one (AF269)

$^1$H-NMR (D$_2$O) δ1.55(d, CH$_3$CH), 2.25–2.55 (m, 4H), 3.3–3.42 (m,4H), 4.4 (q. CH$_3$CH)ppm.

MS m/e 187 (M$^+$).

EXAMPLE 49

1-Methylpiperidine-4-spiro-2'-(5'-methyl-1',3'-oxazolidine) AF264

A mixture of 1-methyl-4-piperidone (11.30 g, 0.10 mole) and DL1-amino-2-propanol (9.75 g, 0.13 mole) was heated under reflux for 1.5 h. The reaction mixture was distilled under reduced pressure. After removal of a fraction which distilled at 30°–110° C. (18 mm Hg) and contained water, excess of the amino-alcohol and the product, the pure product 1-methylpiperidine-4-spiro-2'-(5'-methyl-1',3'-oxazolidine) (AF264), was distilled at 11°–115° C. (18 mm Hg, 10.70 g).

$^1$H-NMR (CDCl$_3$) δ1.22(d, J=6 Hz, CH$_3$CHO—); 1.75 (m, 4H); 2.30(s, CH$_3$N—); 2.49(m, 4H); 2,70(dd) and 3.27(dd) j1=6.6 Hz, J2=12 Hz, —CH$_2$NH—); 4.04(m, j1=6.6 Hz, j2=6 Hz, CH$_3$CHO—) ppm.

$^{13}$C-NMR (CDCl$_3$) δ20.3(CH$_3$CHO—); 35.3 and 36.7 (C6&C10); 45.5(CH$_3$N—); 51.7(—CH$_2$NH—); 52.8 (C7&C9); 71.8(CH$_3$CHO—); 93.3(C5) ppm.

MS m/e 170(M$^+$); 169(M$^+$-1); 123; 112; 85; 83(100%) ;71;70; 58.

EXAMPLE 50

1-Methylpiperidine-4-spiro-2'-(4'-ethyl-1',3'-oxazolidine) AF268

A mixture of 1-methyl-4-piperidone (5.65 g, 0.05 mole) and DL 2-amino-1-butanol (6.24 g, 0.07 mole) were heated under reflux for 3 h. The reaction mixture was distilled at reduced pressure. After removal of a fraction which distilled at 30°–128° C. (19 mm Hg, 5.65 g) and contained mainly the product and smaller amounts of water and the reactants, the pure product 1-methylpiperidine-4-spiro-2'-(4'-ethyl-1',3'-oxazolidine)(AF268) was distilled at 129°–130° C, (19 mm Hg, 4.5 g).

$^1$H-NMR (CDCl$_3$) δ0.97(t, J=7.5 Hz, CH$_3$CH$_2$—); 1.45 and 1.69(m, CH$_3$CH$_2$—); 1.70–1.89(m, 4H); 2.30(s, CH$_3$N—); 2.32–2.62(m, 4H); 3.25 and 3.96(m, —CH$_2$O—); 3.29(m, —CHCH$_2$CH$_3$) ppm.

$^{13}$C-NMR (CDCl$_3$) δ10.7(CH$_3$CH$_2$—); 26.1(CH$_3$CH$_2$—); 34.9 and 36.3(C6&C10); 45.3(CH$_3$N—); 52.5 and 52.7 (C7&C9); 58.5(C3); 69.5(C2); 93.1(C5) ppm.

EXAMPLE 51

1-Methylpiperidine-4-spiro-5'-(3'-ethyl-1',4'-oxathiolane-2'-one) (AF271)

A solution of 1-methylpiperidone (1.921 g, 0.017 mole), 2-mercaptobutyric acid (2 g, 0.0167 mole) and p-toluenesulfonic acid (300 mg) in acetonitrile was refluxed for 36 hrs. Then the solution was evaporated, dissolved in methanol and the product separated on a silicagel column with chloroform/methanol/ammonia (97:2.5:0.5) as eluent. Further purification was performed on a silicagel column with chloroform/methanol (95:5) as eluent.

$^1$H-NMR (CDCl$_3$) δ1.0(t,CH$_3$CH$_2$), 1.6(m,3H), 2.1(m, 1H, CH$_3$CH$_2$), 2.25–2.4(m,4H), 2.3(s,3H), 2.8–2.95(m,2H), 3.75(dd, CH$_2$CH)ppm.

MS m/e 215 (M$^+$)

EXAMPLE 52

Synthesis of Piperidine-4-spiro-5'-(3'-propargylhydantoin) (AF186)

Compound AF185 was demethylated according to the procedure developed for AF160(Des) (see Example 3) and was further purified by chromatography on a silica column (chloroform/methanol/ammonia 80:19:1) The free base was precipitated as a white non-hygroscopic hydrochloric acid salt.

$^1$H-NMR (D$_2$O HCl salt) δ2.0–2.15(m,2H); 2.2–2.35(m, 2H); 2.68(t,1H J=3.5 Hz); 2.91(s,CH$_3$N—); 3.25–3.35(m, 2H); 3.55–3.65(m,2H), 4.3(d,2H, j=3.5 Hz)ppm.

MS m/e 207(M$^+$, base peak); 179; 151; 113.

EXAMPLE 53

Synthesis of 1-Methylpiperidine-4-spiro-5'-[3'-(2-butynyl)hydantoin] (AF199)

Compound AF199 was synthesized according to the procedure developed for AF185 (see Example 50), and was further purified by chromatography on a silica column (chloroform/methanol/ammonia 80:19:1) The free base was precipitated as a white non-hygroscopic hydrochloric acid salt.

$^1$H-NMR (CDCl$_3$, free base) δ1.65–1.8(m,2H); 1.78(t,3H, J=1.7 Hz); 1.9–2.25(m,4H); 2.33(s,CH$_3$N—); 2.8–2.95(m, 2H); 4.22(q,2H,J=1.7 Hz); 6.7(bs,1H)ppm.

MS m/e 235(M$^+$); 165; 154; 71(base peak);

EXAMPLE 54

1-Methylpiperidine-4-spiro-5'-(2'-methyl-1',4'-thiazolidine-3'-one) AF261, and its optical isomers (+)AF261 & (−)AF261

Compound AF261 as a free base (3.23 g., 16 mmole) and di-p-toluoyl-D-tartaric acid (5.8 g, 15 mmole) were placed in 250 ml flask, isoamyl alcohol 28 g and toluene 130 g were added and the mixture was refluxed for 5 minutes. The clear solution was partially evaporated under reflux by a stream of N$_2$ until the formation of a slight turbidity and allowed to stand overnight. The resulting precipitate was filtered off and recrystallized from isoamyl alcohol-toluene several times until enantiomeric purity of above 98% (by GC and NMR) was obtained. The solid product was basified and precipitated as the hydrochloric acid salt to yield 207 mg white non-hygroscopic solid $[α]^{25}{}_D$=54.8° (hydrochloric acid salt in methanol).

The mother liquor was evaporated, basified and treated with Di-p-toluoyl-L-tartaric acid and crystallized four times until obtaining enantiomeric purity of above 98% (by GC and NMR). The solid product was basified and precipitated as the hydrochloric acid salt to yield 207 mg white non-hygroscopic solid $[α]^{25}{}_D$=+55.78° (hydrochloric acid salt-in methanol).

Determination of optical purity was done by NMR using (R)-(−)-2,2,2-trifluoro-1-(9-anthryl)ethanol as resolving agent. 7.5 mg of it vs 2.5 mg of each enantiomer in C6D6 shows the presence of a single enantiomer. The NMR spectrum of the hydrochloric acid salt was identical to that of the (±) AF261.

The purity of each enantiomer was determined by GC using a capillary column Chrompack XE-60-S-Val-S-α-PEA, WCOT fused silica 50 m., id 0.26 mm., od 0.35 mm., flow 0.9 ml N$_2$, oven temperature 175° C.; retention time 64 min. and 65 min.

The NMR spectrum of the hydrochloric acid salt was identical to that of the (±) AF269.

EXAMPLE 55

1-Methylpiperidine-4-spiro-5'-(2'-ethyl-1',4'-thiazolidine-3'-one) AF267, and its optical isomers (+)AF267 & (−)AF267

Compound AF267 as a free base and di-p-toluoyl-D-tartaric acid were treated according to the procedure developed for AF261 (see example 53), until enantiomeric purity of above 90% (by GC) was obtained. The solid product was basified and precipitated as the HCl salt to yield 207 mg white non-hygroscopic solid. $[α]^{25}{}_D$=−67.0° (CHl salt in methanol, >90% optical purity). The mother liquor was evaporated, basified and treated with di-p-toluoyl-L-tartaric acid in the same manner. After four recrystallizations, the resulting product (>90% ee) was basified and precipitated as the HCl salt, $[α]^{25}{}_D$=70.8° (HCl salt in methanol, >95% optical purity).

The purity of each enantiomer was determined by GC using a capillary column Chrompack XE-60-S-Val-S-α-PEA, WCOT fused silica 50 m., id 0.26 nm., od 0.35 mm., flow 0.9 ml $_{N2}$, oven temperature 175° C.; retention time 83 min. and 88 min. The NMR spectrum of the hydrochloric acid salt was identical to that of the (+) AF267.

EXAMPLE 56

Synthesis of 1-methylpiperidine-4-spiro-2'-(5'-methyl-1',3'-dioxolan-4'-one) AF274

Lactic acid (8 ml) was dried azeotropically with benzene. To the dry and still hot lactic acid more dry benzene was added followed by p-toluenesulfonic acid (300 mg) and 1-methylpiperidone (5.00 g, 0.027 mole). The mixture was refluxed until no additional water separated. Then the solution was evaporated and the residue dissolved in chloroform and washed with saturated sodium bicarbonate solution (25 ml). The water phase was washed with chloroform (25 ml) and the combined organic phases washed again with water (2×10 cc). The organic phase was dried on sodium sulfate mixed with charcoal, filtered and evaporated to give 8.7 g of an oily crude product. After combined trituration with hexane, ether and petroleum-ether (40–60) the remaining oil was dissolved in acetone and then oxalic acid (1eq.) was added to it. After a while, a white solid precipitated which was identified as the oxalic acid salt of 1-methylpiperidine-4-spiro-2'-(5'-methyl-1',3'-dioxolan-4'-one) AF274.

$^1$H-NMR (oxalic acid salt, CDCl$_3$+DMSO-d6) δ1.5(d, 3H, J=7 Hz), 2.15(m,4H), 2.63(s,3H), 2.9(m, 2H), 3.05(m, 2H), 4.55(q, 1H, J=7 Hz) ppm.

$^1$H-NMR (free-base, CDCl$_3$) δ1.5(d,3H, J=7 Hz), 1.95(m, 4H), 2.32(s,3H). 2.5(m,2H), 2.6(m,2H), 4.5(q, 1H, J=7 Hz)ppm.

Mass spectrum m/e 185 (M$^+$)

EXAMPLE 57

2-methyl-1,4-thiazolidine-3-one-spiro[5.3']-quinuclidine AF273

A mixture of 3-quinuclidinone (2.50 g, 20.0 mole), thiolactic acid (2.55 g, 24.0 mmole), and ammonium carbonate (2.9 g) in toluene (100 ml) was sealed in a stainless steel pressure vessel and heated at 108° C. with stirring for 28 h. An oil separated from the reaction mixture, it was removed and the toluene solution which remained was evaporated to give a residue (2.5 g). It was crystallized from acetone to give a crystalline solid (0.460 g) which is mostly composed from one enantiomeric pair of AF273. It was crystallized again from acetonitrile and then from dichloromethane to give one pure enantiomeric pair (±) AF273A (0.210 g). m.p. 201°–202° C.

$^1$H-NMR (CDCl$_3$) δ1.53(d, j=7.2 Hz, CH$_3$CH—); 1.65 (m, 2H); 1.92)m, 2H); 2.03(m, 1H); 2.83(m, 4H); 3.18 and 3.32(dd, J=15 Hz, —NCH$_2$CNH—); 3.89(q, J=7.2 Hz. CH$_3$CH—); 8.58(bs, —NH—) ppm.

MS m/e 212(M$^+$); 155; 142(M$^+$-70); 123; 96; 71; 70(100%); 58.

The mother liquor from the first crystallization which was enriched in the other enantiomeric pair, was chromatographed on a column of silica gel (Merck 60). Elution with a solvent mixture of chloroform/methanol/ammonia(aq.) 96:3:1 gave first the second pure enantiomeric pair (±) AF273B (0.106 g) m.p.181°–182° C. (from acetonitrile).

$^1$H-NMR (CDCl$_3$) δ1.52(d, j=7 Hz, CH$_3$CH—); 1.64(m, 2H); 1.93(m, 2H); 2.03(s, 1H); 2.70–2.98(m, 4H); 3.19(s, —NCH$_2$CNH—); 3.85(q, J=7 Hz. CH$_3$CH—); 8.60(bs, —NH—) ppm.

MS same as (±) AF273A.

Next a mixture of all the isomers was obtained, end finally the other pure enantiomeric pair (±) AF273A.

EXAMPLE 58

1-Methylpiperidine-4-spiro-5'-(2'-methyl-1',4'-thiazolidine-3'-thione) (AF275)

A suspension of 1-methylpiperidine-4-spiro-5'-(2'-methyl-1',4'-thiazolidine-3'-one) (AF261 ) (1.00 g, 5.00 mmole) and Lawesson's Reagent (1.40 g, 3.46 mmole) in dry toluene (25 ml) was stirred and heated to 100° C. for 3 h. The solvent was removed from the reaction mixture and the residue separated on a dry silicagel column (Merck 60, 0.040–0.665). Elution with a solvent mixture of chloroform, methanol, ammonium hydroxide 96:3:1 (v/v) gave pure 1-methylpiperidine-4-spiro-5'-(2'-methyl-1',4'-thiazolidine-3'-thione) (AF275) (0.81 g) needles from acetone m.p. 171°–172° C. (dec.).

$^1$H-NMR (CDCl$_3$) 1.69(d, J=7.1 Hz, CH$_3$CH—); 2.00 (m, 2H); 2.00–2.35 (m, 4H); 2.30 (s, CH$_3$N—); 2.80 (m, 2H); 4.26 (q, J=7.1 Hz. CH$_3$CH—); 8.74 (bs. —NH—) ppm.

MS m/e 216(M$^+$); 156; 98; 97; 96(100%); 70.

EXAMPLE 59

1-Methylpiperidine-4-spiro-4'(5')-(2'-methylthio-2'-imidazoline-5'(4')-one) (AF187)

(a) 1-Methylpiperidine-4-spiro-5'-(2'-thiohydantoin) (AF195) hydrochloric acid salt (1.00 g, 4.25 mmole) was added to a stirred sodium stirred sodium hydroxide (0.36 g, 9.00 mmole) solution in methanol (30 ml). A precipitate was formed (NaCl). Methyl iodide (0.664 g, 4.68 mmole) was added at room temperature to the above mixture and stirring continued for 1.3 h. The reaction mixture was evaporated at reduced pressure and the residue extracted with hot dichloromethane. Removal of the dichloromethane gave a residue (0.58 g), which was separated on a column of silicagel (Merck 60, 0.040–0.065). Elution with a solvent mixture of chloroform, methanol, ammonium hydroxide 89:10:1(v/v) gave 1-methylpiperidine-4-spiro-4'(5')-(2'-methylthio-2'-imidazoline-5'(4')-one) (AF187) (0.23 g); m.p. 176°–177° C. (from acetone).

$^1$H-NMR (CDCl$_3$) 1.57 (m, 2H); 2.00 (m, 2H); 2.35 (s, CH$_3$N—); 2.52 (m, 2H); 2.56 (s, CH$_3$S—); 2.84 (m, 2H): 6.73(bs, —NH—) ppm.

$^{13}$C-NMR (CDCl$_3$) 12.6 (CH$_3$S—); 32.7 (C$_3$); 45.8 (CH$_3$N—); 50.8 (C$_2$); 68.3 (C$_4$); 163.8 (—C—SCH$_3$); 188.1 (—C=O) ppm.

MS m/e 213(M$^+$); 198(M$^+$—CH$_3$); 143(M$^+$-70); 71.

UV(EtOH) lambda$_{max.}$ 236 nm (ε7800); 255 nm (shoulder. (8ε4300).

(b) A solution of 1-methylpiperidine-4-spiro-4'-(2'-methylthio-5'-aminomethyl-4'H-imidazole) AF193 (30 mg) in aqueous hydrochloric acid (0.5 ml, 16%) was left at room temperature for three days. The solvent was removed at reduced pressure and the residue made basic with concentrate aqueous sodium hydroxide solution, then extracted with dichloromethane-methanol. The extract was dried (Na$_2$SO$_4$) and the solvent removed to give a residue, which was separated on a thick layer silicagel plate (Merck kieselgel 60 F$_{254}$), developed with chloroform, methanol, ammonia (aq.) 79:20:1(v/v) to give AF187 (8 mg), identical to an authentic sample.

EXAMPLE 60

1-Methylpiperidine-4-spiro-4'-(1'-ethyl-2'-ethylthio-2'-imidazoline-5'-one) (AF188)

To a suspension of 1-methylpiperidine-4-spiro-5'-(2'-thiohydantoin) hydrochloric acid salt (AF195) (4.04 g, 0.0172 mole), and potassium hydroxide (3.85 g, 0.0686 mole) in ethanol (100 ml), ethyl bromide was added (5.60 g, 0.0514 mole) and the mixture was refluxed with stirring. After reflux of 2 h, the main product was still the monoethyl derivative, therefore more potassium hydroxide (0.95 g, 0.0169 mole) and ethyl bromide (2.00 g, 0.0184 mole), were added to the reaction mixture and the reflux continued for additional 3 h. The solvent was evaporated under reduced pressure, water (20 ml) was added to the residue and it was extracted with ether. The extract was dried (Na$_2$SO$_4$) and the solvent removed to give a residue (0.973 g) which was crystallized from petroleum ether to give pure 1-methylpiperidine-4-spiro-4'-(1'-ethyl-2'-ethylthio-2'-imidazoline- 5'-one) (AF188) (0.513 g) m.p. 95°–96° C. Chromatography of the mother liquor, after removal of the solvent, on a dry silicagel column (20 g, Merck 60. 0.040–0.065 mm) and elution with a solvent mixture of chloroform, methanol, ammonia(aq.) 84:5:1 gave an additional amount of pure AF188 (0.310 g).

$^1$H-NMR (CDCl$_3$) 1.19 (t, J=7.2 Hz, CH$_3$CH$_2$N—); 1.40 (t, J=7.2Hz, CH$_3$CH$_2$S—); 1.43 (m, 2H); 1.99 (m, 2H); 2.36 (s, CH$_3$N—); 2.51 (m, 2H); 2.77 (m, 2H); 3.18; (q, J=7.2 Hz, CH$_3$CH$_2$S—); 3.49 (q, J=7.2 Hz. CH$_3$CH$_2$N—) ppm.

$^{13}$C-NMR (CDCl$_3$) 14.1 (2CH$_3$CH$_2$—); 24.4(CH$_3$CH$_2$S—) 33.0 (C$_6$); 35.1 (CH$_3$CH$_2$N—); 46.2 (CH$_3$N—); 51.0 (C$_7$); 68:6 (C$_5$); 158.8 (—N=C—); 183.9(—C=O) ppm.

MS m/e 255(M$^+$); 226(M$^+$—Et); 185(M$^+$-70); 71; 70.

EXAMPLE 61

1-Methylpiperidine-4-spiro-4'-(1'-ethyl-2'-imidazoline-5'-one) (AF220)

Raney nickel (0.30 g) was added to a solution of 1-methylpiperidine-4-spiro-4'-(1'-ethyl-2'-ethylthio-2'- imidazoline -5'-one) (AF188) (0.214 g) in ethanol (10 ml) and the mixture refluxed for 4 h. As the reaction was not complete, more raney nickel (0.30 g) was added and the reflux continued for additional 4 h. The reaction mixture was filtered and the catalyst washed with methanol and dichloromethane. The filtrate and washings were combined and evaporated to give 1-methylpiperidine-4-spiro-4'-(1'-ethyl-2'-imidazoline-5'-one) (AF220) (0.160 g) as an oil.

$^1$H-NMR (CDCl$_3$) 1.27 (t, J=7.3 Hz, C$\underline{H}_3$CH$_2$—); 1.46 (m,2H); 2.03 (m, 2H); 2.36 (s, CH$_3$N—); 2.48 (m, 2H); 2.82 (m, 2H); 3.53 (q, J=7.3 Hz, CH$_3$C$\underline{H}_2$—); 7.72 (s, —CH=N—) ppm.

$^{13}$C-NMR (CDCl$_3$) 13.9 (C$\underline{H}_3$CH$_2$—); 32.2 (C$_6$); 35.3 (CH$_3$C$\underline{H}_2$—); 45.7 (CH$_3$N—); 56.5 (C$_7$); 68.2 (C$_5$); 151.6 (—N=CH—); 183.9 (—C=O) ppm.

An attempt to purify the product by chromatography on a dry silicagel column (20 g, Merck 60 0.040–0.065 mm) eluting with a solvent mixture of chloroform, ether, methanol. ammonia (aq.) (25:17:3:1) (v/v) gave as the main product the ring-opened hydrolysis product; 1-methylpiperidine-4-formylamino-4-N-ethylcarboxamide (AF221) crystallized from ether-dichloromethane m.p. 108°–109° C.

$^1$H-NMR (CDCl$_3$) 1.13 (t, J=7.2 Hz, C$\underline{H}_3$CH$_2$—); 2.04–2.32 (m, 6H); 2.28 (s, CH$_3$N—); 2.65 (m, 2H); 3.28 (dq. CH$_3$C$\underline{H}_2$—); 5.73 (s, HCON$\underline{H}$—); 6.97 (bs, EtN $\underline{H}$CO—); 8.18 (s,HCON—) ppm.

MS m/e 213(M$^+$); 195(M$^+$—H$_2$O); 168(M$^+$-EtNH$_2$); 141 (M$^+$-EtNHCO); 98; 97; 96; 71; 70.

The hydrolysis product AF221 can be ring-closed to AF220 by heating it (150° C.) in vacuum.

The compounds according to the invention exhibit pharmacological activity End are therefore useful as pharmaceuticals, e.g. for therapy. More particularly, the spiro-compounds provided by the present invention have central and peripheral (or both) activity on the nervous system. One common characteristic activity is on the cholinergic system where the compounds are ligands (e.g. agonists or antagonists) on the muscarinic receptors.

The agonistic or antagonistic profile of the compounds was evaluated in a number of tests including computer-assisted molecular evaluation, biological testing in vitro and in vivo.

Computer-assisted molecular evaluation For muscarinic agonistic activity E pharmacophoric model, based on examination of numerous agonists, was constructed. The model includes definition of those parts, in the structure of the agonists that are essential for activity, their mutual spacial orientation and to some extent the maximal volume allowed for a ligand to be an agonist.

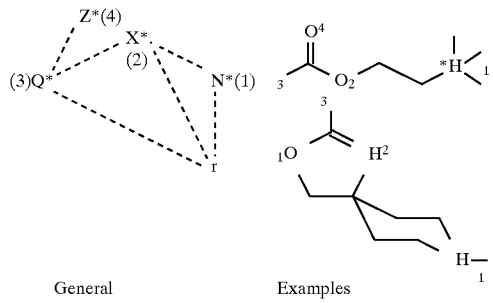

General    Examples

In the above formulae, point r is a negative charge interacting with the cationic head of the agonist. Its position relative to the nitrogen is defined in the model. Important distances (D) are as follows: D(r-N*)=3.0; D(r-X*)=6.50; D(r-Q*)=8.70; D(x*-Q*)=2.45. The optimal dihedral angle r-x*-Q*-z*=–85. Deviation from those optimal model parameters within certain limits does not abolish activity (Table 1).

Certain important features of this model are listed below:

1. The model allows one to distinguish between full and partial muscarinic agonists. The distinction is based upon correlation between the distance r-X* and agonistic efficacy.
2. The nature of the atom in position 4, corresponding to the carbonyl oxygen in acetylcholine can vary considerably as well as the dihedral angle r-x*-Q*-z* within the class of muscarinic agonists.
3. When the distance r-Q* becomes too large for agonistic activity, weakly binding antagonists are obtained. From this model prediction regarding receptor subtype specificity of a muscarinic agonist can be made, based upon the agonist structural rigidity; the nature of Z* and the model parameters.

The pharmacophoric model can be used in screening of new compounds for potential muscarinic activity in the following way a: the new structure is optimized to determine its low energy conformers; b: these conformers are examined for the proper arrangement of the pharmacophoric elements. Alternatively the new structure can be forced into the pharmacophoric conformation by using one of the induced fit routines. The resulting conformation is then compared to the low energy conformation of the same structure. Application of these procedures produced a reliable answer in all the cases examined (Table 1). Albeit there is no way to predict whether muscarinic activity is manifested only by compounds conforming to this model, those that do fit are active as agonists.

The limitation of volume for the cationic head for muscarinic agonists is inferred from docking experiments of the relevant structures (as depicted in Table 1) into a molecular model of the transmembrane domain of the m1 muscarinic receptor. Compounds larger than quinuclidine derivatives cannot be accommodated by the macromolecular binding site.

The compounds listed in Table 1 are divided into four groups. The first group includes several well known muscarinic agonists. Their structures are characterized by optimal pharmacophoric parameters. The second group includes agonists that display suboptimal pharmacophoric patterns and are therefore mainly partial agonists. Structures of the compounds in the third group deviate from the pharmacophoric pattern for muscarinic activity, defined by the previous groups. These compounds are therefore either antagonists or devoid of muscarinic activity. Group four lists some of the potential muscarinic agonists based on their pharmacophoric parameters.

TABLE 1

| Pharmacophoric parameters for muscarinic agonists. | | | | |
|---|---|---|---|---|
| Agonist | Selectivity | r-X* (A) | r-Q* (A) | X*-Q* (A) | r-X*-Q*-Z* |
| (Group 1) | | | | | |
| ACh | M2 > M1 | 6.40 | 8.44 | 2.40 | –86 |
| Dioxolane | M2 > M1 | 6.51 | 8.71 | 2.42 | –85 |
| Muscarine | M2 > M1 | 6.50 | 8.53 | 2.44 | –75 |

TABLE 1-continued

Pharmacophoric parameters for muscarinic agonists.

| Agonist | Selectivity | r-X* (A) | r-Q* (A) | X*-Q* (A) | r-X*-Q*-Z* |
|---|---|---|---|---|---|
| Methylfurm | M2 > M1 | 6.40 | 8.54 | 2.43 | −59 |
| Oxatholane | M2 > M1 | 6.55 | 8.90 | 2.43 | −25 |
| (Group 2) | | | | | |
| AF102B | M2 > M1 | 5.93 | 8.24 | 2.45 | −173 |
| AF150 | M2 > M1 | 5.78 | 7.91 | 2.45 | −118 |
| AF151 | M2 > M1 | 5.82 | 8.20 | 2.45 | −170 |
| AF150(S) | M2 > M1 | 5.72 | 8.35 | 2.82 | −84 |
| AF151(S) | M2 > M1 | 5.88 | 8.15 | 2.38 | −177 |
| AF160 | M2 > M1 | 5.80 | 8.26 | 2.72 | −96 |
| AF160 (Des) | M2 > M1 | 5.78 | 8.26 | 2.70 | −95 |
| (Group 3) | | | | | |
| AF133 | | 5.98 | 8.33 | 2.96 | 34 |
| AF134 | | 6.00 | 8.58 | 2.62 | 9 |
| AF168 | | 6.69 | 9.10 | 2.72 | −44 |
| AF172 | | 5.71 | 9.64 | 4.00 | −101 |
| (Group 4) | | | | | |
| AF170 | | 6.07 | 8.62 | 3.01 | −60 |
| AF181 | | 5.92 | 8.35 | 2.75 | −88 |
| AF184 | | 5.93 | 8.44 | 2.65 | −87 |
| AF185 | | 5.96 | 8.21 | 3.13 | −105 |
| AF196 | | 5.92 | 8.40 | 2.73 | −87 |
| AF202 | | 5.78 | 8.10 | 2.42 | −170 |
| AF210 | | 5.89 | 8.20 | 2.43 | −170 |
| AF215 | | 5.94 | 7.93 | 2.44 | −108 |
| AF216 | | 5.72 | 8.32 | 2.84 | −96 |
| AF260 | | 5.75 | 8.02 | 2.45 | −132 |
| AF261 | | 5.91 | 7.80 | 2.37 | −107 |
| AF264 | | 5.77 | 8.07 | 2.46 | −128 |
| AF265 | | 5.82 | 7.72 | 2.38 | −94 |
| AF267 | | 5.91 | 7.84 | 3.25 | −105 |
| AF270 | | 5.79 | 8.27 | 2.73 | −93 | methylfurmethide

Biological Testing

Test No. 1. Isolated Guinea-pig ileum preparation.

Compounds of the invention were tested for their agonistic and antagonistic activities in the guinea-pig ileum preparation (method used as described by Fisher et al., J. Pharm. Exp. Therap. 257:392–403 (1991). Table 2 summarizes the results obtained with some of the compounds.

TABLE 2

Effect on guinea-pig ileum preparation

| Compound | $EC_{50}$ ($\mu M$) | Remarks |
|---|---|---|
| AF102B* | 3.5 | partial agonist |
| AF134* | | antagonist at 6 $\mu M$ |
| AF151(S) | 7.3 | full agonist |
| AF160 | 3.2 | full agonist |
| AF160 (Des) | | partial agonist at 0.1 mM maximal contraction of 80% of carbachol |
| AF177 | | weak antagonist at 0.25 mM |
| AF178 | 100 | partial agonist (80% of ACh) |
| AF179 | 100 | partial agonist (80% of ACh) |
| AF180 | 100 | partial agonist (80% of ACh) |
| AF182 | | antagonist at 0.1 mM; full antagonist 0.2 mM |

(U.S. Pat. No. 4,855,290); weak antagonist for ACh-induced contraction Behaved as a muscarinic antagonist in the guinea-pig ileum preparation; surprisingly, it inhibited AF102B-induced contractions better than it blocked ACh-induced contractions. Thus if the contraction induced by AF102B in this preparation are mediated mainly through M3 receptors, AF134 appears to be a selective M3 antagonist in this preparation.

Test No. 2. Binding to muscarinic receptors in the brain; competition with [$^3$H]QNB, [$^3$H]NMS and [$^3$H]OXO-M in membranes prepared from rat cortex and cerebellum.

Rat cerebral cortex and cerebellar membrane preparations, using the ligands [$^3$H]NMS, [$^3$H]Pirenzepine and [$^3$H]oxotremorine-M were used for evaluating the new compounds (Tables 3 and 4).

TABLE 3

Competition of tested compounds with [$^3$H]PZ, [$^3$H]QNB or [$^3$H]NMS (rat cortex), and [$^3$H]QNB or [$^3$H]NMS (cerebellum), respectively.

Cortex

| | [$^3$H]PZ | | [$^3$H]QNB | | [$^3$H]NMS | |
|---|---|---|---|---|---|---|
| Compound | $K_H \mu M(\%)$ | $K_L \mu M$ | $K_H \mu M(\%)$ | $K_L \mu M$ | $K_H \mu M(\%)$ | $K_L \mu M$ |
| Carbachol | 0.06(38) | 18.6 | 6.8(18) | 980 | 0.1(41) | 11 |
| Oxo-tremorine | | | | 2.4 | | |
| McN-A-343 | | | | 7.9 | | |
| AF102B | | 1 | | 7.1 | | 1.1,1.5 |
| AF133 | | 2.7 | | | | |
| AF134 | | 0.13 | | | | |
| AF151(S) | 0.75(11) | 20 | 24(44) | 459 | | |
| AF160 | 1.4(34) | 19 | | 58 | 0.45(31) | 12 |
| AF160 (Des) | 1.3(36) | 9 | | 40 | | 7 |
| AF178 | 17(58) | 90 | | | | |
| AF180 | | 5.4 | | | | |
| AF177 | 0.06(10) | 7 | | | 0.1(14) | 13 |
| AF182 | 0.06(27) | 8.3 | | | 0.12(23) | 9.2 |
| AF183 | | | 0.06(14) | 100 | | 260 |
| AF185 | | | | 4.8 | | 9 |

Cortex

| | [$^3$H]PZ | | [$^3$H]NMS | |
|---|---|---|---|---|
| Compound | $K_H \mu M(\%)$ | $K_L \mu M$ | $K_H \mu M(\%)$ | $K_L \mu M$ |
| AF181 | | 3.6 | | |
| AF184 | | 0.64 | | |
| AF196 | | >1000 | | |
| AF197 | | 48 | | |
| AF213 | | 5.7 | | |
| AF264 | | 294 | | |
| AF260 | 0.2(36) | 16 | 0.014(12) | 32 |
| AF261 | 0.03(26) | 25 | 8.6(33) | 100 |
| AF261A | | 18 | | 20 |
| AF261B | 0.13(34) | 6.7 | 0.032(31) | 4.2 |
| AF263 | 0.33(14) | 10 | 0.19(23) | 13 |
| AF265 | 0.93(12) | 49 | 0.18(27) | 39 |
| AF267* | | 2.8* | | 5.88 |
| AF267A | | | | 10.9 |
| AF267B | | | | 4.3 |

Cerebellum

| | [$^3$H]QNB | | [$^3$H]NMS | |
|---|---|---|---|---|
| Compound | $K_H \mu M(\%)$ | $K_L \mu M$ | $K_H \mu M(\%)$ | $K_L \mu M$ |
| Carbachol | 1.5(54) | 52 | 0.02(56) | 6 |
| Oxotremorine | | 0.8 | | |
| McN-A-343 | | 24.4 | | |
| AF102B | | 18.1 | | 1.4,0.4 |
| AF133 | | 5.1 | | |
| AF134 | | 3.8 | | |
| AF151(S) | | 45 | | |
| AF160 | | 61 | 0.56(46) | 19 |
| AF160 (Des) | 5(36) | 86 | | 2.4 |
| AF178 | | 200 | | |

TABLE 3-continued

Competition of tested compounds with [3H]PZ,
[3H]QNB or [3H]NMS (rat cortex), and [3H]QNB or [3H]NMS
(cerebellum), respectively.

| | | |
|---|---|---|
| AF180 | 350 | |
| AF177 | | 20 |
| AF182 | | 21 |
| AF183 | | 310 |
| AF185 | | 7 |
| AF181 | | 5 |
| AF184 | | 2.9 |
| AF197 | | 18 |
| AF260 | 0.46(58) | 87 |
| AF261 | 0.83(45) | 23 |
| AF261A | | 18 |
| AF261B | 0.29(53) | 24 |
| AF267 | | 2.3 |
| AF267A | | 6.9 |
| AF267B | 0.15(26) | 3.2 |

*Following $Cu^{2+}$ treatment, the competition assay with [3H]PZ exposed two-site binding sites for AF267 ($K_H$ = 22 nM (18%); $K_L$ = 2.5 μM). This observation indicates that AF267 binds to muscarinic receptors in rat cerebral cortex as an agonist (Fisher et al. J. Pharmacol. Exptl. Therap. 257: 392–403 (1991).

The calculated ratios of $Ki^{PZ}/Ki^{NMS}$ or $Ki^{PZ}/Ki^{QNB}$ (Table 3) are a commonly used indication for M1 selectivity of muscarinic ligands, lower ratios being indicative of better M1 selectivity. In addition the ratios of $Ki^{PZ}/Ki^{QNB}$ from rat cerebral cortex vs cerebellar membrane preparations are also indicative of M1 selectivity of muscarinic ligands, lower ratios than 1 being indicative of M1 selectivity (Fisher et al, J. Pharmacol. Exptl. Therap. 257:392–403 (1991). Using these assays we could detect that some of the compounds in this invention show a relatively high preference for M1 muscarinic receptors. Such are: AF133, AF134, AF160, AF160(Des), AF177, AF178, AF181–AF185, AF261, AF265, AF267.

AF185, for example, exhibited 3-fold higher affinity for competing with [3H]PZ as compared with its competition for [3H]NMS binding sites (Ki=1.4±0.15 μM vs. 5±1 μM, respectively; Table 3). This is in sharp contrast with AF102B (U.S. Patent), which displayed almost similar affinities for competing with both ligands (Ki=1.43±0.2 μM vs. 1.86±0.43 μM, respectively; Table 3). Since [3H]PZ is believed to specifically label the M1AChR in the rat cerebral cortex membranes, our new data may indicate that AF185 is a more M1-selective ligand compared with AF102B.

The [3H]NMS binding curves of some of the new compounds in the cerebral cortex membranes indicated interaction with two sites: about a quarter of the binding sites exhibited high affinity towards these compounds. This may indicate high agonistic efficacy in this preparation. Such compounds are: AF260, AF261, AF263 and AF265.

Surprisingly, some of the new compounds exhibited two-site competition curves with [3H]PZ in rat cerebral cortex (Table 3). These include: AF160, AF160(Des), AF260, AF261, AF265. The two-site competition curves of these compounds with [3H]PZ were converted to single mass-action curves in the presence of the stable GTP analog, GppNHp (not shown). Similar observations on GppNHp sensitivity were observed for competition with [3H]NMS (not shown). This indicates that these compounds behave as efficacious agonists for M1 receptors in rat cerebral cortex. This is in contrast with AF102B competition assays which typically yield mass-action curves. These observations may suggest some differences between recognition of rat cortex M1 receptors by AF102B and these new compounds.

AF267 exhibited single-site competition curves with both [3H]NMS and [3H]PZ in rat cerebral cortex membranes. Studies of phosphoinositides (PI) hydrolysis and arachidonic acid release described below indicated that this compound is a partial agonist. The mass-action binding pattern was therefore similar to data for the M1-selective agonist AF102B to muscarinic receptors in this preparation. We have previously demonstrated that treatment of rat cerebral cortex membranes with 0.1 mM CuSO4 may expose cryptic agonistic binding properties of AF102B (Fisher et al, JPET 257:392–403, 1991; the published data employed competition of AF102B with [3H]QNB, but similar observations were obtained using [3H]NMS and [3H]PZ). Also, such treatment may increase the proportion of high affinity sites for certain agonists, which already exhibit high-affinity sites without $Cu^{2+}$ treatment (e.g., AF160). We have therefore studied the binding properties of AF267 following $Cu^{2+}$ treatment. Such treatment followed by competition assay with [3H]PZ exposed 18% high affinity sites for AF267 ($K_H$=22 nM, i.e. about 100-fold higher affinity compared with $K_L$=2.5 μM) without significant change in the low affinity sites. This observation suggests that AF267 may bind to muscarinic receptors in rat cerebral cortex similarly to to AF102B. The ability of $Cu^{2+}$ treatment to expose the high-affinity sites for certain partial agonists may be related to stabilization of receptor/G-protein interaction by coordination complexes of the metal ions with crucial sulfhydryls on these macromolecules(Gurwitz et al, BBRC 1984, 120:271–277). In control membranes this interaction is apparently not favored in the presence of partial agonists, which thus do not exhibit a high-affinity site in competition assays with labelled antagonists.

The ability of compounds to displace [3H] oxotremorine-M {[3H]OXO-M} binding provided a measure of affinity for the high affinity agonist state of the receptor. The ratio of the Ki values for the displacement of [3H]NMS or [3H]QNB and [3H]OXO-M is used in the literature to predict efficacy. Ratios greater than 100 are associated with full agonists; antagonists give ratios close to unity and intermediate values indicate partial agonists (Orlek et al., J. Med. Chem. 34:2726, 1991).

The new compounds were studied in a competition assay with the labeled, non-selective muscarinic agonist, [3H] OXO-M, employing rat cerebral cortex membranes; the potent agonistic character of AF179 and AF160 is reflected in their relatively

TABLE 4

Competition with [3H]OXO-M by congeners of AF160 and reference muscarinic agonists in rat cerebral cortex preparation

| Compound | Ki (μM) | $Ki^{NMS}/Ki^{OXO-M}$ |
|---|---|---|
| A. Mass action curves[a]: | | |
| CCh | 0.06 ± 0.05(3) | 380 |
| Pilocarpine | 0.1 | |
| AF102B | 0.6 ± 0.2(3) | 2.1 |
| AF160 | 1.8 ± 0.2(3) | 9.4 |
| AF177 | 11 | 1.4 |
| AF179 | 1.3 ± 0.3 | 31 |
| AF182 | 14 | 1 |
| AF183 | >100 | ~1 |

| | $K_H$ (μM) | % H | KL (μM) | $Ki^{NMS}/K_L{}^{OXO-M}$ |
|---|---|---|---|---|
| B: Two-site competition curves[b] | | | | |
| AF160 Exp. 1 | 0.05 | 36 | 2.2 | |
| (Des) Exp. 2 | 0.03 | 58 | 1.8 | |

TABLE 4-continued

Competition with [³H]OXO-M by congeners of AF160 and
reference muscarinic agonists in rat cerebral cortex preparation

|  | | | | | |
|---|---|---|---|---|---|
| | Exp. 3 | 0.02 | 42 | 2.1 | |
| | mean(1–3) | 0.033 ± 0.007(3) | 45 ± 6 | 2.0 ± 0.1 | 3.5 |
| AF185 | Exp. 1 | 0.04 | 53 | 49 | 0.18 |
| | Exp. 2 | 0.01 | 18 | 3 | 3 |

Note: binding experiments were performed using washed rat cerebral cortex membranes in TRIS/Mn$^{2+}$ buffer for 0.5 hour at 25° C.; Ki$^{NMS}$ data are mean values from Table 3. Data generally are from 1–4 experiments.
[a]data are for drugs exhibiting mass-action competition curves with [³H]OXO-M.
[b]data are for drugs exhibiting two-site competition curves with [³H]OXO-M; with AF160 (Des) and AF185, mass-action curves were observed in certain experiments.

Surprisingly, AF169(Des) and AF185 were the only drugs tested whose competition curves (using [³H]OXO-M and rat cerebral cortex membranes) did not exhibit single-site mass-action curves (Table 4). The extremely potent competition of these drugs with a sub-fraction of receptors labeled by [³H]OXO-M in rat cerebral cortex membranes may indicate that these drugs are highly subtype selective. Thus, the calculated ratios of Ki$^{NMS}$/KH$^{OXO-M}$ (Table 4) may indicate that AF160(Des) is a potent agonist for a subset of rat cerebral cortex muscarinic receptors, compared with the other congeners of the AF160 group and with AF102B itself. However, this was not observed: competition curves of both AF160(Des) and AF185 with [³H]NMS consistently yielded simple mass-action curves. In fact, only AF160 which exhibited a two-site curve in competing with [³H]NMS yet competed with [³H]OXO-M with a simple mass-action curve. Therefore, the explanation of receptor subtype heterogeneity which is exclusively detected in the [³H]OXO-M binding, but not in the [³H]NMS binding assays, does not seem attractive. Alternative explanations could involve possible interactions with allosteric sites on the muscarinic receptors, which are not detected by the state of the receptor which binds antagonists such as [³H]NMS but is unmasked by using the agonist [³H]OXO-M. Another possible explanation for the shallow competition curves in the [³H]OXO-M binding assay, is that the system has not reached equilibrium. In the competition assays employing AF160 (Des) or AF185, equilibrium was not reached at 30 min, since binding data were different at 30 min compared with 60 min at 25° C. When the assays were terminated at 30 min. shallow competition curves with [³H]OXO-M were observed for both AF160(Des) or AF185. A likely explanation is that AF160(Des) and AF185 have relatively slow kinetics (both slow association rates and slow dissociation rates) compared with AF102B. This would result in a very slow approach to equilibrium in competition assays, yielding the apparent detection of two-site binding isotherms under non-equilibrium conditions. It is reasonable to assume that both association and dissociation rates are relatively slow: if only the association rates of AF160(Des) and AF185 were slow compared with AF102B, they would have demonstrated much lower affinities than AF102B. On the other hand, if their dissociation rates were lower, their affinities should have been much higher than that of AF102B.

The rat cerebellum is relatively homogeneous with respect to the mAChR subtypes expressed (mostly M2). AF102B exhibited similar potencies in competing with [³H]OXO-M binding in both the rat cortex and cerebellum. In contrast. AF160(Des) and AF185 exhibited higher potencies in the cortex vs. the cerebellar membranes; this was reflected as two-site competition curves only in the cortex membranes (re also Table 4 for cortex). Again this might indicate different kinetics for these compounds in the cortex vs the cerebellum, respectively.

Test No. 3. Second messenger activations in brain slices and in cell cultures.

In a procedure for measuring the efficacy of the tested compounds as agonists on the M1 muscarinic receptors, brain slices from rat cortex (200 μM cubes) are prepared. For phosphoinositides (PI) turnover assay, these brain slices are loaded with [³H]inositol (4 μCi/ml) by incubating them in Krebs balanced salt solution containing the labeled ligand for 1 h at 37° C. under oxygenation. After washing, 50 μl aliquots are added to each tube containing 10 mM LiCl in fresh Krebs solution with or without the tested compound. Following incubation for 20 min at 37° C., the reaction is terminated and labeled products are separated on AG-1-X8 columns as described by Berridge (Biochem. J. 258, 849–858, 1983). Partial agonists, according to the compound tested, produced a less than 80% activation of PI hydrolysis as compared with CCh (a full agonist). Thus for example, AF160 caused a significant elevation in IP$_3$ (1.6 fold). In comparison to CCh. AF160 was a partial agonist with an efficacy of 50% of the reference compound. AF160 (Des) was also active, although to a lesser extent than AF160. AF102B as another M1 agonist was less active than AF160, white AF178 was not active in this assay.

Cell cultures enriched in one subpopulation of muscarinic receptors are used to evaluate second messenger activations by the tested compounds. For PI turnover studies the method of Berridge (Biochem. J. 258:849–858, 1983) is used; for arachidonic acid mobilization studies cells are labeled for 16 h with 0.2 μCi/ml of tritiated-arachidonic acid in original growth media. Prior to assay, cells are washed a total of six times with serum-free DME supplemented with HEPES (20 mM) and bovine serum albumin (1 mg/ml). Following the washing procedure, 0.5 ml of the same medium are added with ensuing addition of the tested ligands. Assays are terminated by transferring the media to Eppendorf tubes and centrifuging for 10 min at 6000 g. Radioactivity in supernatants is counted and presented as dpm tritiated-arachidonic acid released per well. Cyclic AMP accumulation in intact cells is evaluated according to the method of Pinkas-Kramarski et al, Neurosci. Lett. 108:335–340, 1990, whereas adenylyl cyclase activity in isolated membranes is determined according to Johnson and Salomon (Methods in Enzymology Vol 195. R. A. Johnson and J. D. Corbin. eds. Academic Press, pp 3–21, 1991).

Compounds of Formulae I–IX with a maximal rate of PI turnover and/or arachidonic acid mobilization (but no significant activation of adenylyl cyclase) higher than 25% are preferred. Some examples for such activity can be found in AF160, AF160(Des), AF178. AF179, AF180, AF185, AF260, AF261, AF263, AF265, AF266, AF267. These compounds are capable of activating M1 muscarinic receptors.

Unlike acetylcholine, CCh, oxotremorine-M and other classical full agonists, these compounds induce selective activation of distinct signalling via M1 (or M3) muscarinic receptors. In particular, the selective activation by muscarinic agonists of PI hydrolysis without (or with minimal) activation of cAMP accumulation is the general pattern of activity of the new compounds. These observations may imply induction of the M1 muscarinic receptor-coupling to distinct G-proteins by these selective muscarinic ligands. Thus in addition to the activation of the M1 receptors, these compounds are also selective at the level of distinct secondary messengers. This concept of select activation of only distinct G-proteins via the same muscarinic receptor using selective muscarinic ligands was recently described by the inventors under the concept of ligand-selective signaling employing CHO cells transfected with the rat m1AChR (Fisher et al. Biorganic & Medicinal Chem. Lett. 2:839–844, 1992) and in a neuronal type cell line, e.g. PC12M1 cell line (Sac. Neuroci. Abs. November 1993). The possible relevance of this signaling pathway for the development of cholinergic replacement therapy for Alzheimer's disease (AD) is evident in view of findings on elevated Gs levels in AD patients and aged brains (Harrison et al., Mol. Brain Res. 10:71, 1991; Young et al., Dev. Brain Res., 61:243, 1991). Thus compounds from the present invention can be important for the treatment of Alzheimer's disease. Some of the compounds are full agonists while others are partial agonists when compared with CCh in stimulating PI hydrolysis in cell cultures transfected with m1AChR. Partial agonists are: AF160, AF160(Des), AF178, AF180, AF181, AF265, AF267, AF260, AF261, AF263 and AF266 had full agonistic activities in this assay. Concentration response curves for AF260 and AF261 indicated that maximal activities were obtained at 10 $\mu$M and 100 $\mu$M, respectively. AF265 and AF267 behaved as partial agonists, with maximal activities of 75% and 66% relative to 1 mM CCh, respectively. AF181 presented weak partial agonistic activity in this assay. Thus, at a concentration of 1 mM it partially activated PI hydrolysis but attenuated CCh-induced PI hydrolysis, as expected for a partial agonist AF213 and AF184 showed antagonistic activity as these compounds blocked the PI hydrolysis signal of CCh. Of the enantiomers of AF267, the more active is AF267B, the (−)-enantiomer; this compound activates PI hydrolysis in cells transfected with the m1 receptors even at 10 $\mu$M (40% of CCh) and at 100 $\mu$M (80% of CCh).

We tested the potency or the new compounds to induce desensitization of the CCh-mediated PI hydrolysis signal. AF261 induced a smaller desensitization response compared with CCh: following a 24 hour exposure to 100 $\mu$M or 1 mM AF261, the PI hydrolysis response to stimulation with 1 mM CCh was decreased by 45% as compared to a reduction by 60% following pre-incubation with 1 mM CCh. AF267, a compound which presented partial agonistic activity in inducing PI hydrolysis, was less capable in inducing desensitization. Thus, following an overnight incubation with 1 mM AF267, the original CCh-mediated PI response was reduced by merely 29%.

We also tested the new compounds for their ability to induce PI hydrolysis in cells transiently transfected with the human m1AChR, m3AChR or m5AChR, in parallel experiments as described by Pittel and Wess (Mol. Pharmacol. 45:61–64, 1994). AF267 exhibited the highest selectivity towards the m1AChR subtype, being about 100-fold more potent for m1AChR as compared to m3AChR-transfected cells ($ED_{50}$ values were 1.5 and 150 $\mu$M, respectively). This is particularly evident when comparing the signal induced by 10 $\mu$M AF267, which is already maximal in m1AChR-transfected cells, but is only 15% of the maximal CCh signal in m3AChR-transfected cells. AF265 was somewhat more potent and more efficacious in m1AChR than in m3AChR transfected cells and much less active in m5AChR. Similar results were obtained with AF267 and in particular for its more active enantiomer, the (−)-enantiomer, in cell cultures stably transfected with m1 AChR and m3 AChR, respectively.

Arachidonic acid (AA) release is another biochemical pathway that is activated by agonists of the m1AChR. Since this biochemical pathway may be linked to the m1AChR via a different G protein than the PI hydrolysis, we also tested the new compounds in this assay, employing the cell cultures stably transfected with rat m1AChR. AF263, AF265, AF266 and AF267 (at 1 mM) showed partial agonistic activities in this assay. Of the enantiomers of A267, the active enantiomer is A267B, the (−)-enantiomer, which is a full agonist on AA release at 0.1 and 1 mM. AF260 and AF261 showed full agonistic activities compared with 1 mM CCh, in agreement with observations of PI hydrolysis in the same cell line. We observed a tendency of these agonists to induce more AA release compared with 1 mM CCh. This may indicate that the CCh-mediated signal is already undergoing desensitization during the assay period (20 min at 37° C.). It is plausible that this desensitization is smaller with the tested compounds. Alternatively, certain tested compounds may be more efficacious than CCh as M1-agonists, i.e. "superagonists". In that case, it is not clear why this property was not observed in the PI hydrolysis assay employing AF260 and AF261.

Pre-incubation of cell cultures transfected with m1AChR with 1 mM CCh for 3 h followed by extensive wash-out of the ligand (6×1 ml) reduced the AA release considerably. The basal AA release was minimally affected, indicating that no residual CCh was present following the wash-out. By comparison, in the same experiment pre-incubation with 1 mM AF265 or AF102B diminished the AA release response to 1 mM CCh only to about half the original response. For longer incubation periods, we preferred drug concentrations of 100 $\mu$M, as concentrations of 1 mM have no physiological relevance for long-term treatments. Following pre-incubation with 100 $\mu$M CCh for 24 hours the AA response was almost completely last. We compared the ability of the new compounds to desensitize the CCh-mediated AA release signal. Surprisingly, pre-incubation with 100 $\mu$M AF265 for 24 hours did not result in any decrease in the AA response. This deserves particular notice, considering our findings that this compound is a partial agonist in this assay. In contrast, stimulation with AF260, AF261 and AF263 (all at 100 $\mu$M for 24 h) considerably reduced the CCh-mediated AA release signal. Similar pre-incubations with AF102B or AF267 resulted in relatively small interference with the subsequent CCh-mediated AA release signal, again pointing to the similarity between these two compounds.

Test 4. Neurotrophic-like effects in cell cultures

Activation of M1 receptors by agonists can lead to synergistic effects with nerve growth factor (NGF) in certain cell cultures enriched with m1 receptors. e.g. PC12 (rat pheochromocytoma cells) transfected with the rat m1AChR (PC12M1 cells), (Pinkas-Kramarski et al, J. Neurochem. 59:2158–2166, 1992).

It has now been discovered, in accordance with another aspect of the invention, that compounds of Formulae I–IX with a maximal rate of PI turnover higher than 25% can synergize the neurite outgrowth produced by NGF. Two classes of compounds can be detected among the compounds of the invention: 1) compounds like AF260, AF261 and AF263 which in the absence of NGF induced neurite outgrowth almost similarly to CCh; and 2) those compounds, which in sharp contrast to oxotremorine, do not promote neurite-outgrowth or induce only minimal morphological change in the absence of NGF. Both classes are important for the treatment of AD. In the second class no axonal growth would take place uncontrollably. Therefore, a favorable drug candidate for the treatment of AD, for example, would induce neuritogenesis only under strict control of locally synthesized and released growth factors, such as NGF, brain-derived nerve factor (BDNF), NT-3 etc. Some examples for such a unique activity can be found in compounds like AF160, AF160(Des), AF185 which are at least as potent as AF102B in synergizing NGF-induced neurite outgrowth. Neurites extended following a combined treatment with NGF and these new compounds were stable for long periods in culture. Hence, it can be assumed that the signalling pathway(s) employed by these compounds for induction of neurite outgrowth are not desensitizing rapidly. This is very reminiscent of NGF itself, which induces very stable and long-lasting neurite-promoting effects in PC12 cells, as well as in primary cultures of sympathetic neurons. It should be noted, however, that old untreated cultures of the tested cells deteriorated, and contained many dead cells, which detached from the plate surface. Interestingly, the cell death phenomena were smaller in cultures which were treated previously with a combination of the novel compounds and NGF. It is well known that NGF rescues PC12 cells from programmed cell death (e.g., Rukenstein et al., J. Neuroscience 11:2552–2563, 1991). Therefore, these observations show that it is possible that similar survival-promoting responses are mediated by compounds of the present invention. All these properties provide additional utility for these compounds in relation to potential treatment for Alzheimer's disease patients.

The neurotrophic-like activity of those agonists of the present invention in the neuronal cells, which is also dependent on the presence of NGF, probably indicates that these compounds exerts neurotrophic activities in conjunction with some signal(s) mediated via NGF receptors. One of the possibilities is that these effects are indirect via m1AChRs-mediated increased release of amyloid precursor proteins (APP), vide infra. Notably, endogenous APP are necessary for normal growth of fibroblastic cells, and exogenous APP can stimulate proliferation of these cells (Saitoh et al. Cell, 58:615, 1989; Mattson et al., TINS 16:409–414, 1993). Interestingly, the secreted forms of APP, among other activities, are known to regulate neurite outgrowth and to promote neuronal survival (reviewed by Mattson et al., TINS 16:409–414, 1993). Neuronal cell-death in AD probably involves decreased production and/or availability of neurotrophines, which is turn compromises survival of cholinergic neurons. If the neurotrophic-like events induced by the M1 agonists also occur in the brain this might have a most important. clinical significance and thus may indicate a novel treatment for AD.

Test 5: Amyloid precursor protein (APP) secretion in brain slices and cell cultures There is growing evidence that β-amyloid is a contributor to the pathological process leading to AD. Based on the "Amyloid cascade hypothesis" AD results from the mismetabolism of amyloid precursor protein (APP) (Mattson et al., TINS 16:409–414, 1993). Activation of mAChRs, and in particular the m1 subtype, increases secretion of APP in vitro (Nitsch et al, Science 258:304,1992; Buxbaum et al, PNAS US 89:10075, 1992; Lahiri et al, Biochem. Int. 28:853, 1992). Thus, according to a further aspect of the invention, compounds of Formula I–IX, in particular those showing selective m1 agonistic activity and increased release of APP, can be beneficial not only in the treatment of AD, but in delaying its progression or even in preventing AD.

The method employed for evaluation of APP secretion is the Western immunoblotting technique (Nitsch et al., PNAS 90:5191–5193, 1993). We have employed the 22C11 monoclonal anti-APP, which is widely used for detection of APP. This antibody is directed against the amino-terminal region of APP, and identifies all the APP isoforms reported to date. It does not detect amyloid or c-terminal APP fragments formed following APP secretion. For evaluating the effects of the new compounds on APP release, cell lines transfected with m1 receptors were cultured in 12-well plates (in some experiments, in 6-well plates) as described by Pinkas-Kramarski et al. (J. Neurochem. 59:2158, 1992). Ligands were added from sterile 100×stock solution for tested periods. Experiments were terminated by washing the plates twice in serum-free medium. Cells were scraped off the plates in cold phosphate/saline buffer (pH=7.4; PBS) buffer. Following centrifugation (10 min, 10000 g) the supernatants were discarded and the pellets were suspended in 0.1 ml cold lysis buffer containing protease inhibitors cocktail (50 mM TRIS:HCl (pH=7.4), 150 mM NaCl, 5 mM EDTA. 1% Triton X-100, 0.1 mM PMSF, 5 Units/ml aprotinin, 5 μg/ml pepstatin A, 5 μg/ml leupeptin). The pellets were then sonicated for 5 sec at maximal setting (Branson sonicator, model 130) and centrifuged again. The supernatants (cell membrane extracts) were transferred to clean tubes. Samples were taken for protein determination by the Lowry method.

For APP assay equal amounts of protein (typically 100 μg/lane) were diluted in sample buffer containing 0.6% SDS and 1% 2-mercapto-ethanol, and loaded on 10% acrylamide/SDS minigels (Hoeffer Scientific). Pre-stained molecular weight standards (Sigma) were loaded on each gel. Gels were run at a constant current of 25 mAmp/gel at 4° C. Blotting was performed at 100 mAmp for 16–18 h at 4° C., using a nitrocellulose membrane. The following steps were carried out at room temperature. Membranes were blocked for 1 h by immersing in PBS containing 10% low-fat milk. This step was followed by washing 3×5 min in PBS containing 0.05% Tween-20 and 0.1% BSA (PBST). Anti-APP monoclonal antibody, clone#22C11 from Boehringer Manneheim (cat. #1285-262) was added at a dilution of 1:200 (0.25 μg/ml IgG)in PBST buffer for 2 h at RT or 18 h at 4° C. In some experiments, similar blots were probed with control mouse IgG at a similar concentration. This step was followed by 3×5 min washing steps in PBST. The secondary horseradish peroxidase-linked goat anti-mouse IgG antibodies (from Jackson Immunochemicals; cat. #115-035-003) were used at 1:2000 in PBST for 1 h, followed by washing as above. Staining of immunoblots was performed at room temperature for 15–30 min using a fresh solution of 4-chloronaphthol (0.2 mg/ml in TBS containing 16% ethanol) and $H_2O_2$ (0.01%). Stained blots were photographed (Kodak TMAX negative film) and scanned in an LKB UltroScan KL laser scanner set at 40 μm vertical interval size and 2.4 mm horizontal slit width. Each lane was scanned three times at slightly different positions; data obtained was the mean optical density values.

By this method we measured the amount of APP remaining in the cell membrane fraction following incubation (typically for 24 h) with the tested compounds. The smaller APP levels remaining in the membranes following such incubation with agonists were taken as an indication that more APP was secreted by the cells. This type of measurement is relevant when considering the ability of muscarinic agonists to decrease accumulation of β-amyloid in Alzheimer disease, because only membrane associated APP, unlike secreted forms of APP, may give rise to β-amyloid. For measuring the APP which is secreted to the cell culture medium ("conditioned medium") we had to concentrate the conditioned medium, using Amicon microfiltration membranes (30 kDa cutoff). Following the concentration step, protein amounts in the samples were measured by the Bradford method (Bio-Rad kit #500-0006) using bovine gamma-globulin as a standard. Equal protein amounts were loaded on poly-acrylamide gel electrophoresis (PAGE). The amount of APP in the samples was analyzed by immunoblotting with the 22C11 monoclonal anti-APP antibody, as described above. Molecular weights were estimated from pre-stained standards (Sigma) which were included in each gel.

Compounds of Formulae I–IX with a maximal rate of APP secretion in cell cultures higher than 125% (over basal taken as 100%) are preferred. Such examples for such activity can be found in AF160(Des), AF179, AF185, AF261, AF263, AF265, AF267.

To enable the processing of a larger number of samples simultaneously, some studies were performed using a dot-blot technique (96 dots may be processed simultaneously on a single membrane). In this technique, conditioned medium from stimulated PC12M1 cells is applied directly to nitrocellulose membranes under vacuum (without prior concentration). The membranes are then probed similarly to the immunoblotting protocol. Detailed concentration-response and time-dependency studies were also analyzed by separation of the secreted APP on PAGE. The results of these studies and those obtained from the dot-blot studies are in good agreement. Studies of APP secretion by cells transfected with m1AChR were thus performed with the new compounds and employing also the dot-blot technique and 1 h incubation. Some of the compounds such as AF261, AF263, AF265 and AF267 are full agonists in this assay.

Desensitization of m1AChR-mediated APP secretion is stronger during prolonged incubations with CCh compared with partial agonists from this invention. This explanation is especially attractive, when considering our data on desensitization of the arachidonic acid (AA) release signals in combination with the recent suggestion of Emmerling et al. (BBRC 197:292–297, 1993) that AA release is involved in stimulation of APP secretion. Our data would indicate that some of the new compounds may be favored over the highly efficacious agonists for clinical use to lower cell-associated APP levels over long periods. Compounds which exhibited minimal desensitization in the AA release assay are AF265 and AF267. Measurements of cell-associated APP following incubations with AF265 or AF267 for 24 h (both at 100 $\mu$M) indicated decreased APP levels, which were stronger with AF267 and almost similar to the effect of CCh, while AF265 had a weaker effect.

The data on APP secretion by cell cultures stably transfected with m1AChR clearly demonstrate that several of the new compounds may stimulate APP secretion, and may therefore contribute to decreased amyloid accumulation in vivo. However, to allow an extrapolation of the tissue-culture data to an in vivo situation, it should preferably be demonstrated that the compounds may also stimulate APP secretion in the brain. To that end, APP secretion by rat cerebral cortex slices was studied. In a typical experiment, rat cerebral cortex slices were prepared immediately from freshly-dissected tissue, minced in two perpendicular directions by a McIlwain Tissue Chopper (300×300 micron) and rinsed three times with oxygen-saturated Krebs buffer. Washed slices were equilibrated with this buffer for 50 min at 37° C. Following the equilibration step (which is required for removal of cell debris resulting from the slicing protocol), the buffer was changed to Krebs buffer containing 50 $\mu$g/ml BSA (as a protein carrier) and proteases inhibitors cocktail (0.1 mM PMSF and 5 $\mu$g/ml each leupeptin, pepstatin and aprotinin-A). The slices were dispensed to plastic tubes and stimulated for 1 h at 37° C. (2 h in one experiment) with the indicated concentrations of the tested compounds. At the end of the incubation period, the buffer samples were collected by centrifugation, analyzed for protein content, and equal protein amounts were separated and processed for immunoblotting with 22C11 anti-APP monoclonal antibody, using PAGE similarly to the experiments with cultured cells. Secreted APP appeared as two protein bands, having apparent molecular weights of 117 kDa (major band) and 90 kDa (minor band). These APP bands may correspond to secreted forms of APP751 and APP695 (the major Kunitz-containing and Kunitz-deficient forms of APP). Alternatively, they may correspond to mature and immature (non-glycosylated) forms of secreted APP751). At present, sufficient data to distinguish between these possibilities is unavailable, because the 22C11 monoclonal antibody employed in these studies identifies all forms of secreted APP. Both CCh or AF267, for example (both at 0.1 mM) increased APP secretion by rat cerebral cortex slices by 2–3-fold compared with control APP secretion. This was evident for both the 117 kDa and the 90 kDa protein bands.

The observations on APP secretion by cerebral cortex slices are unique. To date, the only published demonstration of APP secretion by brain tissue in-vitro is by Nitsch et al. (PNAS 90:5191–5193, 1993) who reported that electrical stimulation of rat hippocampal slices increased APP release. Notably, their study did not include stimulation with a receptor agonist. Our observations therefore are innovative and novel, as they are the first demonstration of regulation of APP secretion in brain tissue by any receptor ligand, and in particular, an M1 agonist like AF267. Those compounds which stimulate APP secretion in rat cortical slices are preferred. Such compounds can be considered all those agonists in this invention capable of stimulating second messengers like PI >25% control. These unique observations may indicate the potential of some of the compounds for slowing the deposition of A4-amyloid peptides in brains of Alzheimer's disease patients.

Test 6: Tau protein phosphorylation in cell cultures transfected with the m1AChRs and in rat cortical slices Tau ($\tau$) is a neuron-specific microtubule-associated protein which is abundant in axons. Tau is expressed as several isoforms, all of which are derived by alternative splicing of a single gene (human tau has 6 isoforms, having 352–441 amino acids). It functions in stabilization of microtubules of neuronal axons: its binding to microtubules is regulated by its phosphorylation in distinct sites (Mandelkow and Mandelkow, TIBS 18:480–483, 1993). This binding, in turn, regulates axonal growth and stability (Baas et al., J. Cell Biol. 115:1333–1344, 1991; Mattson, Brain Res. 582:107–118:1992). One of the hallmarks of Alzheimer's disease, in addition to amyloid deposition in plaques, is accumulation of tau or tau-derivatives in neurofibrillary tangles (NFTs). These tangles probably reflect the end-product of neuronal cell death in the diseased brain tissue. Numerous studies have demonstrated changes in tau protein phosphorylation in post-mortem brain samples of AD patients. This phenomena is best documented as increased immuno-reactivity with the monoclonal antibody ALZ-50, which was shown to detect hyper-phosphorylated forms of tau in these brain samples (Vincent and Davies. PNAS 87:4840–4844, 1990; Vincent and Davies, Brain Res. 531:127–135, 1990). It was therefore suggested that alterations in the delicate balance between tau-specific kinases/phosphatases may be involved in the process of neuronal cell death in AD, and therefore a correction of such probable imbalance may be of potential therapeutic value.

Accordingly, the phosphorylation level of tau proteins in cell cultures stably transfected with m1AChR following stimulation with CCh or one of the tested compounds, was studied. This was done by employing the monoclonal antibody tau-1, which was shown to recognize only de-phosphorylated, but not phosphorylated, isoforms of tau (Mandelkow and Mandelkow, TIBS 18:480–483, 1993). Following incubations of the cells or rat cortical slices with the agonists for various periods, the cells or slices were washed three times with PBS, scrapped in PBS containing 0.2 mM EDTA, and the centrifuged 5 min at 10.000×g. The membrane pellets were analyzed for protein content, and equal protein amounts were loaded on PAGE for immunoblotting with the tau-1 antibody. Measurements of immuno-reactivity were carried out similarly to the studies of APP (employing video-densitometry), with the exception that the peroxidase-coupled second antibody was detected using the Enhanced Chemi-Luminescence (ECL) technique (kit RPN-2109; Amersham, UK).

Notably, both CCh or the tested agonists increased tau-1 immuno-reactivity, and this increase was completely blocked by atropine. A striking increase in CCh-mediated tau-1 immuno-reactivity was observed in cells cultured with NGF (50 ng/ml) for 3 days prior to stimulation with the muscarinic ligands. Similar experiments employing varying concentrations of CCh or the tested agonist indicated that the increased tau-1 immuno-reactivity required relatively high ligand concentrations (10–100 $\mu$M).

Tan phosphorylation in rat cerebral cortex slices following stimulation with CCh in comparison with the present compounds, was also measured. Surprisingly, again the muscarinic agonists tested are capable of decreasing tau phosphorylation.

Thus, muscarinic agonists are capable of decreasing tau phosphorylation by activating the transfected m1AChR in cell cultures and more importantly in the brain slices. Also, the effects of these agonists seem to be long-lasting, being evident even following incubations of the cells with 100 $\mu$M ligands for at least three days. These observations may indicate that selective M1-agonists, are capable of decreasing tau phosphorylation.

These observations are novel, as to the best of our knowledge, no relationship was demonstrated to date between the cholinergic deficiency in Alzheimer's disease and the accumulation of phosphorylated tau protein isoforms in the neurofibrillary tangles typical to the diseased brain. These new observations may have relevance to the slowing of the progression of Alzheimer's disease by M1 agonists. In conclusion M1-Agonists can have a number of effects. Thus, surprisingly, the mechanisms of action of m1 agonists is more complex than originally envisaged. The following activities have already been associated with m1 agonists, in vitro (and perhaps in vivo):

1. Binding with and activation of m1 receptors;
2. Distinct activation of select G-proteins (e.g., Gq but not Gs);
3. Neurotrophic-like and synergistic effects with NGF;
4. Secretion of the amyloid precursor protein (APP) and decrease of $\beta$-amyloids;
5. Increasing the proportion of dephosphorylated $\tau$ proteins;
6. NGF-like effects.

All these effects can be interconnected in a model in which activation of m1 AChRs leads to a cascade of related events. These complex mechanisms underlying m1 agonistic activity can be linked into a general scenario which explains the abnormal APP processing, NGF-like deficits and cholinergic deficits in SDAT and AD. Consequently, m1 agonists like those of the present invention may be of value in preventing amyloid formation by promoting selectively and positively the secretase processing pathway, and may also promote the action of neurotrophines in AD, due to their synergistic effect with NGF. Thus, m1 agonists may be useful in a cholinergic replacement strategy and also in delaying the progression of AD. The present compounds which are m1 agonists are (unlike peptides) relatively small molecules, which have neurotrophic-like effects and promote the release and normal processing of APP, and increase the dephosphorylated (or decrease the phosphorylated) tau proteins. Thus, treatment of cells with an m1 agonist might possibly shift the processing of APP from amyloidogenic lysosomal pathway to normal secretory pathway and consequently cholinergic therapies of AD may have longer term effects on $\beta$-amyloid deposition (re also Lahiri et al, Biochem. Int. 28:853–860, 1992). Furthermore, since some of the agonists from this invention show NGF-like effects in a controlled manner and in particular in the presence of NGF, such compounds can be of significant value in the future treatment of AD/SDAT. In this way neurite outgrowth can be better controlled. Moreover, our compounds have a long-lasting beneficial effect on neurite outgrowth, in presence of NGF. Thus it can be speculated that the future possible treatment using such growth factors like NGF for AD/SDAT patients, might require less frequent administrations of the growth factor itself, when administered together with an m1 agonist. Notably, the administration of NGF to the brain is a most difficult task since this compound does not cross the blood-brain barrier. Once this problem will be solved (e.g. via special delivery systems) it will still require repeated administration of NGF-like compounds. m1 Agonists in this regard can reduce the number of the required repeated administration of NGF, since such agonists prolong the effects of NGF (at least, in vitro). Interestingly, clinical trials of NGF (icv) in 2 AD patients showed very serious adverse effects (serious pain, confusion, deterioration of mini-mental score), (3rd Springfield Symposium on Alzheimer's Disease, May 11–15, 1994, Springfield, Ill., USA). The use of M1 agonists like those in the present Invention which synergise with NGF can be of great value in reducing the side-effects associated with NGF in humans, since then lower doses of NGF could be used.

Test No. 7: Pharmacological and toxicological profiles

The study was carried out by observing the animals after iv or oral (mice) or oral (intra gastric for rats) administration of 3–6 dose levels of each substance. Results are summarized in Table 5.

At different time intervals post-administration (10, 20, 30, 45, 60, 120, 240 min and 24 hr) animals were subjected to detailed observations of changes in general behavior, reflexes and autonomic effects. Mortality was recorded at 24 hr post administration of the test compounds. Body temperature in rats was measured using Tele-Thermometer (Model 46 TUC). The various pharmacological and behavioral parameters included: salivation, redness around the nose and mouth, chromodacryorrhea, sedation, ataxia, cyanosis, tremors, convulsions, hypothermia, opisthotonos, respiratory distress, diarrhea, gnawing, piloerection, mortality, changes in pupil diameter, rotarod, hypo- or hyper-activity and vocalization. Some of the tested compounds are non-toxic up to 500 mg/kg (p.o., mice & rats).

TABLE 5

Pharmacological and toxological profiles in mice or rats

| Cpd. AF- | Dose * | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 133 mice | 50♥ |  |  |  |  |  |  |  |  |  |  |  |  |  | 0/5 |
|  | 100♥ |  |  |  |  |  |  |  |  |  |  |  |  |  | 3/5 |
|  | 200♥ |  |  |  |  |  |  |  |  |  |  |  |  |  | 5/5 |
|  | 400 |  |  |  |  |  |  |  |  |  |  |  |  |  | 1/5 |

TABLE 5-continued

Pharmacological and toxological profiles in mice or rats

| Cpd. AF- | Dose * | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 134 | 10♥ | | | | | | | | | | | | | | 0/5 |
| mice | 25♥ | | | | | | | | | | | | | | 0/5 |
| | 50♥ | | | | | | | | | | | | | | 0/5 |
| | 100♥ | | | | | | 4/5 | | | | 2/5 | | | | 3/5 |
| | 100 | | | | | | | | | | | | | | 0/5 |
| | 200 | | | | | | | | | | 1/5 | | | | 0/5 |
| 151 | 50 | 4/4 | 4/4 | 3/4 | 0/4 | 0/4 | 0/4 | 0/4 | 0/4 | | 0/4 | 0/4 | 0/4 | 0/4 | 0/4 |
| (S) | 100 | 4/4 | 4/4 | 4/4 | 0/4 | 0/4 | 0/4 | 0/4 | 0/4 | | 0/4 | 3/4 | 0/4 | 0/4 | 0/4 |
| rats | 200 | 4/4 | 4/4 | 4/4 | 2/4 | 1/4 | 1/4 | 1/4 | 0/4 | | 1/4 | 4/4 | 0/4 | 0/4 | 1/4 |
| | 500 | 4/4 | 4/4 | 4/4 | 4/4 | 4/4 | 4/4 | 4/4 | 0/4 | | 2/4 | 4/4 | 0/4 | 0/4 | 2/4 |
| 160 | 8 | 0/4 | 0/4 | 0/4 | 0/4 | 0/4 | 0/4 | 0/4 | NT | | 0/4 | 0/4 | NT | NT | 0/4 |
| mice | 16 | 0/4 | 1/4 | 0/4 | 0/4 | 0/4 | 0/4 | 0/4 | | | 0/4 | 1/4 | | | 0/4 |
| | 31 | 2/4 | 3/4 | 0/4 | 0/4 | 0/4 | 0/4 | 0/4 | | | 0/4 | 1/4 | | | 0/4 |
| | 63 | 4/4 | 4/4 | 0/4 | 0/4 | 0/4 | 0/4 | 0/4 | | | 0/4 | 0/4 | | | 0/4 |
| | 125 | 3/4 | 4/4 | 4/4 | 0/4 | 0/4 | 1/4 | 0/4 | | | 0/4 | 2/4 | | | 0/4 |
| | 250 | 4/4 | 4/4 | 4/4 | 4/4 | 0/4 | 4/4 | 0/4 | | | 0/4 | 3/4 | | | 0/4 |
| | 500 | 4/4 | 4/4 | 4/4 | 4/4 | 0/4 | 4/4 | 0/4 | | | 0/4 | 3/4 | | | 0/4 |
| rats | 10 | 0/4 | 0/4 | 0/4 | 0/4 | 0/4 | 0/4 | 0/4 | 0/4 | | 0/4 | 0/4 | 0/4 | 0/4 | 0/4 |
| | 25 | 0/4 | 1/4 | 0/4 | 0/4 | 0/4 | 0/4 | 0/4 | 4/4 | | 0/4 | 4/4 | 4/4 | 0/4 | 0/4 |
| | 50 | 4/4 | 4/4 | 0/4 | 1/4 | 0/4 | 0/4 | 0/4 | 4/4 | | 0/4 | 4/4 | 4/4 | 0/4 | 0/4 |
| | 100 | 4/4 | 4/4 | 4/4 | 0/4 | 0/4 | 0/4 | 0/4 | 4/4 | | 1/4 | 4/4 | 4/4 | 0/4 | 0/4 |
| | 200 | 4/4 | 4/4 | 4/4 | 4/4 | 0/4 | 0/4 | 0/4 | 4/4 | | 2/4 | 4/4 | 4/4 | 2/4 | 0/4 |
| | 500 | 4/4 | 4/4 | 4/4 | 4/4 | 0/4 | 0/4 | 0/4 | 4/4 | | 0/4 | 4/4 | 4/4 | 4/4 | 0/4 |
| 160 | 63 | 0/4 | 0/4 | 0/4 | 0/4 | 0/4 | 0/4 | 0/4 | 0/4 | | 0/4 | 0/4 | 0/4 | 0/4 | 0/4 |
| (Des) | 125 | 1/4 | 0/4 | 0/4 | 0/4 | 0/4 | 0/4 | 0/4 | 1/4 | | 0/4 | 1/4 | 0/4 | 0/4 | 0/4 |
| rats | 250 | 2/4 | 0/4 | 0/4 | 0/4 | 0/4 | 0/4 | 0/4 | 1/4 | | 0/4 | 1/4 | 0/4 | 0/4 | 0/4 |
| | 500 | 3/4 | 0/4 | 4/4 | 0/4 | 0/4 | 0/4 | 0/4 | 0/4 | | 0/4 | 3/4 | 0/4 | 1/4 | 0/4 |
| mice | 120 | 0/4 | 0/4 | 0/4 | 0/4 | 0/4 | 0/4 | 0/4 | 0/4 | 0/4 | 0/4 | 0/4 | | | 0/4 |
| | 240 | 0/4 | 0/4 | 0/4 | 0/4 | 0/4 | 0/4 | 0/4 | 0/4 | 4/4 | 0/4 | 1/4 | | | 0/4 |
| | 500 | 1/4 | 0/4 | 0/4 | 0/4 | 0/4 | 0/4 | 0/4 | 0/4 | 0/4 | 0/4 | 2/4 | | | 0/4 |
| | 1000 | 2/4 | 0/4 | 1/4 | 0/4 | 0/4 | 0/4 | 0/4 | 4/4 | 3/4 | 0/4 | 3/4 | | | 0/4 |
| 163 | 25 | 0/4 | 0/4 | 0/4 | 0/4 | 0/4 | 0/4 | 0/4 | NT | 0/4 | 0/4 | 0/4 | NT | NT | 0/4 |
| mice | 50 | 0/4 | 0/4 | 0/4 | 0/4 | 0/4 | 0/4 | 0/4 | | 0/4 | 0/4 | 0/4 | | | 0/4 |
| | 100 | 0/4 | 0/4 | 0/4 | 0/4 | 0/4 | 0/4 | 0/4 | | 0/4 | 0/4 | 0/4 | | | 0/4 |
| | 200 | 0/4 | 0/4 | 0/4 | 0/4 | 0/4 | 0/4 | 0/4 | | 0/4 | 0/4 | 0/4 | | | 0/4 |
| | 400 | 0/4 | 0/4 | 0/4 | 0/4 | 0/4 | 0/4 | 0/4 | | 0/4 | 0/4 | 0/4 | | | 0/4 |
| rats | 50 | 0/4 | 0/4 | 0/4 | 0/4 | 0/4 | 0/4 | 0/4 | 0/4 | NT | 0/4 | 0/4 | 0/4 | 0/4 | 0/4 |
| | 100 | 2/4 | 0/4 | 0/4 | 0/4 | 0/4 | 0/4 | 0/4 | 0/4 | | 0/4 | 0/4 | 0/4 | 0/4 | 0/4 |
| | 200 | 4/4 | 0/4 | 0/4 | 0/4 | 0/4 | 0/4 | 0/4 | 0/4 | | 0/4 | 0/4 | 0/4 | 0/4 | 0/4 |
| | 400 | 4/4 | 0/4 | 0/4 | 0/4 | 0/4 | 0/4 | 0/4 | 0/4 | | 0/4 | 0/4 | 0/4 | 0/4 | 0/4 |
| 177 | 31 | 0/4 | 0/4 | 0/4 | 0/4 | 0/4 | 0/4 | 0/4 | 4/4 | 0/4 | 0/4 | 0/4 | NT | NT | 0/4 |
| mice | 62 | 0/4 | 0/4 | 0/4 | 0/4 | 0/4 | 0/4 | 0/4 | 4/4 | 0/4 | 0/4 | 0/4 | | | 1/4 |
| | 125 | 3/4 | 0/4 | 0/4 | 0/4 | 0/4 | 4/4 | 4/4 | 2/4 | 0/4 | 0/4 | 0/4 | | | 4/4 |
| | 250 | 4/4 | 0/4 | 0/4 | 0/4 | 0/4 | 4/4 | 4/4 | 1/4 | 0/4 | 0/4 | 0/4 | | | 4/4 |
| | 500 | 4/4 | 0/4 | 4/4 | 4/4 | 0/4 | 4/4 | 4/4 | | 0/4 | 0/4 | 0/4 | | | 4/4 |
| 178 | 30 | 0/4 | 0/4 | 0/4 | 0/4 | 0/4 | 0/4 | 0/4 | NT | 0/4 | 0/4 | 0/4 | NT | NT | 0/4 |
| mice | 60 | 1/4 | 2/4 | 0/4 | 0/4 | 0/4 | 0/4 | 0/4 | | 0/4 | 0/4 | 0/4 | | | 0/4 |
| | 144 | 3/4 | 3/4 | 0/4 | 0/4 | 0/4 | 0/4 | 0/4 | | 0/4 | 0/4 | 3/4 | | | 0/4 |
| | 288 | 4/4 | 3/4 | 0/4 | 0/4 | 0/4 | 0/4 | 0/4 | | 0/4 | 3/4 | 2/4 | | | 0/4 |
| | 500 | 4/4 | 4/4 | 0/4 | 0/4 | 0/4 | 4/4 | 0/4 | | 2/4 | 0/4 | 4/4 | | | 0/4 |
| rats | 63 | 1/4 | 0/4 | 0/4 | 0/4 | 0/4 | 0/4 | 0/4 | 0/4 | NT | 0/4 | 0/4 | 0/4 | 0/4 | 0/4 |
| | 125 | 4/4 | 3/4 | 0/4 | 0/4 | 0/4 | 0/4 | 0/4 | 3/4 | | 0/4 | 4/4 | 4/4 | 0/4 | 0/4 |
| | 250 | 3/4 | 3/4 | 1/4 | 0/4 | 0/4 | 0/4 | 0/4 | 3/4 | | 0/4 | 4/4 | 3/4 | 0/4 | 0/4 |
| | 500 | 4/4 | 3/4 | 4/4 | 0/4 | 0/4 | 0/4 | 0/4 | 4/4 | | 1/4 | 4/4 | 4/4 | 0/4 | 0/4 |
| 180 | 63 | 0/4 | 0/4 | 0/4 | 0/4 | 0/4 | 0/4 | 0/4 | NT | 0/4 | 0/4 | 0/4 | NT | NT | 0/4 |
| mice | 125 | 0/4 | 0/4 | 0/4 | 0/4 | 0/4 | 0/4 | 0/4 | | 2/4 | 0/4 | 0/4 | | | 0/4 |
| | 250 | 3/4 | 0/4 | 0/4 | 0/4 | 0/4 | 0/4 | 0/4 | | 3/4 | 0/4 | 0/4 | | | 0/4 |
| | 500 | 4/4 | 3/4 | 3/4 | 0/4 | 0/4 | 0/4 | 0/4 | | 4/4 | 0/4 | 0/4 | | | 0/4 |
| rats | 31 | 0/4 | 0/4 | 0/4 | 0/4 | 0/4 | 0/4 | 0/4 | 0/4 | NT | 0/4 | 0/4 | 0/4 | 0/4 | 0/4 |
| | 62 | 0/4 | 0/4 | 0/4 | 0/4 | 0/4 | 0/4 | 0/4 | 0/4 | | 0/4 | 0/4 | 0/4 | 0/4 | 0/4 |
| | 125 | 1/4 | 0/4 | 0/4 | 0/4 | 0/4 | 0/4 | 0/4 | 0/4 | | 0/4 | 0/4 | 0/4 | 0/4 | 0/4 |
| | 250 | 2/4 | 0/4 | 0/4 | 0/4 | 0/4 | 0/4 | 0/4 | 0/4 | | 0/4 | 0/4 | 0/4 | 0/4 | 0/4 |
| 185 | 31.3 | 0/4 | 0/4 | 0/4 | 0/4 | 0/4 | 0/4 | 0/4 | 0/4 | 0/4 | 0/4 | 0/4 | | | 0/4 |
| mice | 62.5 | 0/4 | 0/4 | 0/4 | 0/4 | 0/4 | 0/4 | 0/4 | 0/4 | 3/4 | 0/4 | 0/4 | | | 0/4 |
| | 125 | 0/4 | 0/4 | 0/4 | 0/4 | 0/4 | 0/4 | 0/4 | 2/4 | 4/4 | 0/4 | 0/4 | | | 0/4 |
| | 250 | 1/4 | 0/4 | 0/4 | 0/4 | 0/4 | 0/4 | 0/4 | 0/4 | 4/4 | 0/4 | 0/4 | | | 0/4 |
| | 500 | 3/4 | 0/4 | 0/4 | 0/4 | 0/4 | 0/4 | 0/4 | 0/4 | 0/4 | 0/4 | 0/4 | | | 0/4 |
| rats | 62.5 | 0/4 | 0/4 | 0/4 | 0/4 | 0/4 | 0/4 | 0/4 | 0/4 | | 0/4 | 0/4 | 0/4 | 0/4 | 0/4 |
| | 125 | 0/4 | 0/4 | 0/4 | 0/4 | 0/4 | 0/4 | 0/4 | 0/4 | | 0/4 | 0/4 | 0/4 | 0/4 | 0/4 |
| | 250 | 0/4 | 0/4 | 0/4 | 0/4 | 0/4 | 0/4 | 0/4 | 0/4 | | 0/4 | 0/4 | 0/4 | 0/4 | 0/4 |
| | 500 | 0/4 | 0/4 | 0/4 | 0/4 | 0/4 | 0/4 | 0/4 | 0/4 | | 0/4 | 0/4 | 0/4 | 0/4 | 0/4 |
| 261 | 3.75 | 0/4 | 0/4 | | 0/4 | 0/4 | 0/4 | 0/4 | 0/4 | | 0/4 | 0/4 | 0/4 | 0/4 | 0/4 |
| rats | 7.52 | 0/4 | 0/4 | | 0/4 | 0/4 | 0/4 | 0/4 | 0/4 | | 0/4 | 0/4 | 0/4 | 0/4 | 0/4 |
| | 15.6 | 3/4 | 4/4 | | 4/4 | 0/4 | 0/4 | 0/4 | 4/4 | | 0/4 | 3/4 | 0/4 | 0/4 | 0/4 |

TABLE 5-continued

Pharmacological and toxological profiles in mice or rats

| Cpd. AF- | Dose * | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| | 62.5 | 4/4 | 4/4 | | 4/4 | 0/4 | 4/4 | 0/4 | 4/4 | | 0/4 | 3/4 | 3/4 | 3/4 | 0/4 |
| | 250 | 4/4 | 4/4 | | 4/4 | 0/4 | 4/4 | 4/4 | 4/4 | | 0/4 | 1/4 | 4/4 | 4/4 | 4/4 |
| 265 | 125 | 0/4 | 0/4 | | 0/4 | 0/4 | 0/4 | 0/4 | 0/4 | | 0/4 | 0/4 | 0/4 | 0/4 | 0/4 |
| rats | 250 | 1/4 | 0/4 | | 0/4 | 0/4 | 0/4 | 0/4 | 2/4 | | 0/4 | 0/4 | 0/4 | 0/4 | 0/4 |
| | 500 | 0/4 | 0/4 | | 0/4 | 0/4 | 0/4 | 0/4 | 0/4 | | 0/4 | 0/4 | 0/4 | 0/4 | 0/4 |
| mice | 125 | 0/4 | 0/4 | 0/4 | 0/4 | | 0/4 | 0/4 | 0/4 | 0/4 | | 0/4 | | 0/4 | 0/4 |
| | 250 | 0/4 | 0/4 | 0/4 | 0/4 | | 0/4 | 0/4 | 2/4 | 2/4 | | 0/4 | | 0/4 | 0/4 |
| | 500 | 2/4 | 0/4 | 0/4 | 0/4 | | 0/4 | 0/4 | 4/4 | 4/4 | | 0/4 | | 4/4 | 0/4 |

*mg/kg, administered orally unless stated otherwise
♥administered intravenously
KEY TO TABLE 5:
1 = salivation
2 = chromodacryorrhea (rats) or lacrimation (mice)
3 = sedation
4 = ataxia
5 = cyanosis
6 = tremors
7 = convulsions
8 = hypothermia
9 = mydriasis
10 = respiratory distress
11 = diarrhea
12 = gnawing
13 = piloerection
14 = mortality

Discussion of Results

AF160

AF160 is a relatively potent muscarinic agonist being more central than peripheral (e.g. hypothermia vs salivation), and less toxic at least 5 times when compared with AF102B. A remarkable finding in this compound was lack of tremors in rats up to the highest tested dose (500 mg/kg, po) and some tremors in mice at doses >125 mg/kg, p.o. A similar pattern was detected in the methyl analog of AF160, namely AF178, where no tremors were detected in both mice and rats up to 500 mg/kg, p.o. Mice are more sensitive to this compound than rats, as peripheral and central side effects occur at lower doses.

In rats, AF160 was found to be a potent agonist. Signs were apparent at a dose as low as 25 mg/kg, $ED_{50}$ values were obtained for hypothermia and gnawing. The extent and severity of symptoms were dose related. The hypothermic effect was long lasting, longer than 4 hr.

Four aspects are remarkable in AF160:
1. Apparently the compound is more CNS active than PNS active (e.g. hypothermia occurs at lower dose than salivation).
2. There is a CNS selectivity since not all CNS effects are observed (e.g. hypothermia vs lack of tremors).
3. The duration of the observed effects is long.
4. No mortality in mice and rats was observed at the highest dose level, 500 mg/kg.

AF160(Des)

In rats, salivation, hypothermia and diarrhea were observed in one out of four animals 45 min after the administration of 125 mg/kg. After increasing the dose to 500 mg/kg the number of animals per group exhibiting these symptoms increased and in addition piloerection and sedation became distinct. The hypothermic effect was not dose-related. No other central or autonomic effects were produced by this compound. The compound is relatively inactive with regard to cholinergic side-effects, In the case of AF160(Des) side effects are elicited at doses >246 mg/kg, p.o., in rats.

In mice, lacrimation, diarrhea and mydriasis were observed after the administration of 240 mg/kg of AF160 (Des). At higher doses and up to 1000 mg/kg, additional symptoms such as salivation, sedation and hypothermia were apparent. The extent and severity of most of the symptoms (except for lacrimation) were dose related. No mortality was observed even at the highest dose level, 1000 mg/kg. Topical application of 1 mg (threshold amount) of AF160(Des) into the eye produced mydriasis within 15 min. In contrast, atropine used as a reference drug for its known local mydriatic effect, produced mydriais within 45 min by as low as 40 μg. This result clearly shows that AF160(Des) induced-mydriasis is central in origin.

AF163

In rats, at a dosage range between 50 to 400 mg/kg, salivation and redness around the nose and mouth were the only effects produced by this compound. These effects were of short onset (10 min) and short duration (20 min). Whereas the number of animals exhibiting salivation was dose related, redness around the nose was found only in one animal at a dose level of 100 mg/kg. In conclusion, only autonomic effects were observed after administration of this compound in rats.

In mice, except for vocalization observed in one animal at the highest dose tested (400 mg/kg), this compound was devoid of any other overt effects. No overt peripheral & central side-effects were detected with AF163, in mice, up to the highest dose tested (400 mg/kg, p.o.). AF163 can be considered a prodrug for AF160 in a similar way as the dithio analog of RS86 (see Bolliger et al, in: Alzheimer's and Parkinson's Disease; Strategies in R&D, eds. Fisher et al, Plenum Press, pp. 585, 1986).

AF177

In mice, hypothermia, hypoactivity and tremors were observed 10 min after the administration of 31 mg/kg. After increasing the dose to 62 mg/kg, the number of symptoms increased. Sedation, ataxia, Straub-taill and falling from the rotarod were observed 20 min after administration in 4/4 mice. Mortality of 1/4 mice occurred 30 min after administration. When increasing the dose to 125, 250 and 500 mg/kg salivation, convulsions and mortality of 4/4 mice were also observed but the onset and the duration of the symptoms became progressively more severe. Calculated $ED_{50}$ values show that AF177 possess central effects mostly. AF177 can be considered a prodrug for a centrally active end potent muscarinic agonist.

AF178

In mice, decreased motor -activity, salivation, lacrimation and diarrhea were seen up to one hour after administration of 60 mg/kg. Increasing the dose to 500 mg/kg resulted in additional symptoms such as respiratory distress, decrease in the performance on the rotarod, tremors and mydriasis. The extent and severity of most of the symptoms were dose related. In general, increasing the doses prolonged the activity. For example: diarrhea, tremors, mydiasis etc. lasted approximately 4 hours. It is worth mentioning that at 500 mg/kg one animal exhibited palpitation within 20 min after the administration, lasting for 10 min. Even though a dose of 500 mg/kg produced profound toxicological symptoms, no mortality was recorded. Thus the estimated $LD_{50}$ would be at a dose higher than 500 mg/kg.

In rats, salivation was the only overt sign following the administration of 62.5 mg/kg of AF178. Increasing the dose to 125 mg/kg more signs were apparent such as chromodacryorrea, hypothermia, diarrhea and gnawing. The extent and severity of those symptoms were increased with the dose. Respiratory distress was apparent only in one animal at a dose of 500 mg/kg, 5 min post injection. The compound cain possess relatively broad safety margin.

AF180

In rats, salivation was the only symptom produced by 125 mg/kg of AF180. It became evident within 20 min after administration and lasted for 40 min. Further increasing the dose to 500 mg/kg increased the duration of the salivation to 230 min. At this dose level, hypothermia was also recorded in three animals 15 to 240 min post injection. No other central or autonomic effects were observed at this dose level.

In mice, hypothermia and mydriasis were observed 20 min after the administration of 125 mg/kg. After increasing the dose to 500 mg/kg, the number of animals per group exhibiting these symptoms increased, and in addition salivation, lacrimation and sedation became distinct. Furthermore the duration of these symptoms was greater than 1.5 hr after administration of 500 mg/kg. No other central or autonomic effects were produced by this compound.

AF185

In mice, mydriasis was observed post administration of 62.5 mg/kg of AF185. At higher doses and up to 500 mg/kg, additional symptoms such as salivation and hypothermia were apparent after administration or the compound. No mortality was observed even at the highest dose level (500 mg/kg).

In rats, except for redness around the nose and mouth, observed in one animal at the highest dose tested (500 mg/kg), this compound was devoid of any other overt effects. It is concluded that AF185 is a very sate compound.

AF261

In rats, hypothermia (a typical CHS effect) was the only symptom produced by 7.5 mg/kg of AF261. It became evident within 10 min after administration and lasted for 50 min. After increasing the dose to 15.6 mg/kg, additional symptoms such as salivation, chromacyorrhea, hypoactivity, ataxia and diarrhea were apparent within 10 min. At higher doses and up to 250 mg/kg, additional signs such as redness around the nose and mouth, tremors, convulsions, opisthotonos, gnawing and piloerection were apparent. These signs could be detected 5–10 min post administration. The severity and the extent of most of those symptoms were dose-related. Mortality of 4/4 rats occurred only at the highest dose tested (250 mg/kg), 45 min after administration.

AF265

In rats, hypothermia (a typical CNS effect) was the only symptom produced by 250 mg/kg of AF265. It became evident within 10 min after administration and lasted for 110 min. No other central or autonomic effects were observed following administration of this compound. Thus this compound is remarkable due to its CNS effect only.

Test No 8: The effects of AF134 in naive rats

The effects of AF134 on memory and learning ability was evaluated in a step-through passive avoidance task, in naive rats. The behavioral paradigm and instrumentation is as described in Fisher et al. Neurosci. Lett. 102:325; (1989). Four groups (20 rats/group) of naive male Sprague-Dawley rats. 200–300 g, 3–4 months old (Charles River Breeding, UK) were treated with one of the following doses of AF134: 1, 5, 10 mg/kg, intraperitoneal (ip) and one group received saline (1 ml/kg, ip).

In AF134-treated rats no significant differences were found between the retention latency of the pre-shock treated rats in which the compound was injected 30 min before the shock and that of post-shock treated rats (in which the compound was injected 60 min after the shock).

In another experimental paradigm AF134 was compared with scopolamine (an antimuscarinic compound) in an 8-arm radial arm-maze in naive rats (behavioral paradigm and instrumentation as described in Fisher et al. Neurosci. Lett. 102:325, 1989). A group of 14 naive rats was treated with scopolamine (0.2 mg/kg,ip) or saline (1 ml/kg, ip) 20 min before running the maze. All arms were baited. Each rat received both treatments with three days interval between treatments. (Ten days of training were followed by ten days of testing). The same experiment in the same rats was repeated with AF134 (5 mg/kg, ip) versus saline (1 ml/kg, ip). Scopolamine showed, as expected, a typical anticholinergic "amnesic" effect at the dose used. However, AF134 did not cause any change in the behaviour of the rats.

AF134, which has antagonistic activity on the M1 (based on binding studies) and M3 muscarinic receptors (based on guinea-pig ileum preparation) does not produce impairment of cognitive effects and thus may be useful in the treatment of motion sickness, Parkinson's disease, mixed Parkinson's and Alzheimer's disease, manic-depression, human bead injury and in a variety of peripheral disorders in the treatment of acute rhinitis, peptic ulcer and asthma.

Test No 9. Behavioral Studies in Animal Models AF160 and AF102B—Radial Arm Maze

The potential beneficial effect of doses of AF160 (3 and 5 mg/kg, p.o.) and AF102B (3 mg/kg, p.o.) in reversing memory deficits of AF64A-injected rats (1.5 nmole/2 $\mu$l/side), was investigated. This animal models mimics to a certain extent the cholinergic hypofunction is SDAT. (Fisher et al, J. Pharmacol. Expl. Therap. 257:392–403,1991). 80 Male Sprague-Dawley rats, 4–6 months old (340–580 g) were used in this study. The time interval between operation and behavioral testing was 2–3 months. One week before starting the behavioral test, rats were transferred to individual cages and were food restricted until reaching approximately 85% of their free feeding weight. Then rats received 5–6 pieces of Altromin (15 g) per day in order to keep their body weight in a steady state. Rats had free access to water. The room was illuminated 12 hr a day (6:00–18:00) and behavioral testing was carried our during the morning.

Behavioral Testing

40 AF64A and 40 saline-injected rats were randomly subdivided into four subgroups and were assigned to AF160 3 mg/kg, AF160 5 mg/kg, AF120B 3 mg/kg (10 ml/kg, p.o.) and DDW. During the first two days of behavioral testing, rats were trained according to the 8 out of 8 RAM-baiting-procedure, in order to familiarize them with the maze and the reinforcing pellets (precision 45 mg). At this stage, rats were placed in the central arena and were allowed free access to all 8 baited arms. Each session was terminated when all eight pellets had been collected or at the end of 15 min, whichever came first. During the third and fourth days pellets were placed only at the end of the arms. Otherwise the other procedures were the same as in pretraining. Testing was carried out during the second week 20 of the experiment. During that time AF160, AF120B or DDW (used as control) were administered once a day, for five days, 60 min before testing.

Data analysis

All movements within the maze were recorded, elapsed time as well as correct and incorrect responses. In order to evaluate the effect of AF160 or AF102B during the testing period compared to the training period which used as a baseline performance, a 3-way ANOVA (2×4×2) with a repeated variable (blocks of training or testing days) and two non-repeated variables (injection of AF64A/Saline, and treatment with various doses of AF160 and AF102B or DDW) was made. Post-hoc comparisons were completed using simple main effects' contrasts.

Results

As regards correct choices out of 8 visited, a significant interaction between groups x treatment x weeks was found [$F(2/48)=3.95$; $P<0.025$]. More specifically, during both training and drug administration period AF64A-injected rats made significantly less correct choices than saline-injected rats ($P<0.01$). Both drugs, AF102B (3 mg/kg) and AF160 (3 mg/kg) improved the performance of AF64A-injected rats during the second week compared to training days ($P<0.001$, respectively). During the second week both groups, AF160 (3 mg/kg) and AF102B (3 mg/kg) reached the same level of performance which was significantly higher than that of the AF64A injected rats treated with water ($P<0.05$). AF160 5 mg/kg had no significant effect on this parameter. In comparison with saline-injected rats, the performance of rats treated with water improved (5%) during the second week compared to the first week ($P<0.01$). Similarly an improvement (7.5%) was also found in rats treated with AF160 (3 mg/kg) ($P<0.001$). AF102B (3 mg/kg) had no effect on this parameter in saline-injected rats.

As regards total errors, a significant interaction was found between groups x treatments x weeks [$F(3/64)=3.49$; $P<0.025$]. In both weeks the number of errors of AF64A-injected rats was significantly higher than that of saline injected rats ($P<0.001$). The number of errors of all four groups of AF64A-injected rats significantly decreased in the second week compared to the first week: AF64A+water-20% ($P<0.01$), AF64A+AF160-3 mg/kg-16% ($P<0.001$), AF64A+AF160-5 mg/kg-15% ($P<0.02$) and AF64A+AF102B-3 mg/kg-30% ($P<0.001$). Although all four groups improved their performance, only that of AF102B-3 mg/kg was higher than the performance of the AF64A+water group. In saline-injected rats, AF160-3 and 5 mg/kg significantly improved the performance in the second week compared to the first week ($P<0.01$, $P<0.001$, respectively) AF102B-3 mg/kg produced a deterioration in performance and this group made more errors in the second week compared to the first week ($P<0.001$).

As regards total time, a significant interaction was found between groups x treatment x weeks [$F(2/48)=3.29$; $P<0.05$). An improvement in time was found in AF64A-injected subgroups except AF64A+AF160-5 mg/kg; AF64A+water-31% ($P<0.01$), AF64A+AF160-3 mg/kg-(47%) ($P<0.00.1$) and AF64A+AF102B 3 mg/kg-(21%) ($P<0.01$). In saline-injected rats a significant effect of improvement in time was found in saline+water-(54%) ($P<0.001$) and saline+AF160 3 mg/kg-(37%) ($P<0.001$). AF102B had no effect on saline-injected rats on this parameter, maybe because of a "floor effect". AF160-5 mg/kg did not affect significantly the saline-injected rats performance although a tendency for improvement can be observed.

Conclusions

1. Rats injected with AF64A (1.5 nmole/2 µl/side) showed a significant impairment in the parameters of correct choices, number of errors and total time compared to saline-injected rats.

2. AF160 (3 mg/kg) significantly improved the performance of AF64A-injected rats (compared to placebo treatment) in the parameters of correct choices and total time. A higher dose of 5 mg/kg was found effective only in the parameter of number of errors compared to baseline (but not to placebo).

AF160(Des)—Morris Water Maze (MWM) task

The objective of this study was to evaluate the ability of the test material AF160(Des) to reverse cognitive impairments in AF64A-injected rats using the MWM task according to the method by Fisher et al, J. Pharmacol. Exptl. Therap. 257:392–403, 1991. AF160(Des) was tested using two doses: 1 and 3 mg/kg p.o. 38 AF64A (3 nmol/2 µl/side)- and 42 saline-injected rats were randomly subdivided into 4 subgroups and were assigned to the different doses of and AF160(Des) (1 and 3 mg/kg, p.o.) or DDW (10 ml/kg, p.o.). The drug was administered once a day for 5 days, 60 min before testing.

No consistent side-effects were observed during behavioral testing. The following results were obtained:

1. An injection of AF64A (3 nmol/2 µl/side) resulted in a significant impairment in performance, as indicated by both parameters escape latency and path length.
2. AF160(Des)-3 mg/kg improved the performance of both AF64A and saline-injected rats on the third block of training. The positive effect suggests using various doses of that compound in the future in order to test its possible beneficial effects on learning and memory deficits. AF185-Passive Avoidance (PA)

This study investigated the effect of AF185, at various doses, on passive avoidance retention in AF64A-treated rats.

Methods

AF64A was injected bilaterally (3 nmol/2 µl/side, icv) to produce the animal model (Fisher et al., J. Pharmacol. Exptl. Therap. 257:392–403, 1991. Four weeks post-operation, AF64A and saline injected groups were randomly subdivided into four subgroups of 10–11 rats each; three subgroups were assigned to different doses of AF185 treatment (1, 5, 10 mg/kg, p.o.) and one subgroup received DDW (10 ml/kg). AF185 was administered immediately after shock and the rats were tested 72 hrs. later. For experimental details see Fisher et al, J. Pharmacol. Exptl. Therap. 257: 392–403, 1991.

Results

The initial and retention latencies measures were analyzed separately by a two-way ANOVA (2×4): Injection-AF64A/Saline vs. Doses of AF185 or DDW.

As regards initial latency, no significant differences were found in the initial latencies between any of the groups.

As regards retention latency, an interaction between groups and treatment was found (F(3/75)=22,31; P<0.001). Simple main effects contrasts showed that the retention latency of AF64A rats with DDW was significantly shorter than that of saline rats treated with DDW (p<0.001). The retention latency of AF64A rats treated with AF185-1,5 or 10 mg/kg was significantly longer than that of AF64A+DDW (p<0.001). No other significant differences were found.

Conclusions

1. AF64A injected rats showed a significant impairment in retention latency compared to saline injected rats.
2. AF64A-injected rats treated with AF185 (1,5 and 10 mg/kg) displayed a retention ability similar to the control animals.
3. AF185 may be a potential compounds for treatment of memory disorders like those observed in Alzheimer's Disease.

The following correlation is provided for examples of specific compounds according to the invention, according to IUPAC systematic nomenclature, with their coda numbers as used herein: 2,8-dimethyl-1-oxo-1-thia-4,8-diaza-spiro[4.5]decan-3-one (AF262); 3-ethyl-8-methyl-1-oxa-4.8-diaza-spiro[4.5]decane (AF268); 2,8-dimethyl-1-oxa-4,8-diaza-spiro[4.5]decane (AF264); 3,8-dimethyl-1,4-dioxa-8-aza-spiro[4.5]decan-2-one (AF274); 2-ethyl-4,8-dimethyl-1-thia-4,8-diaza-spiro[4.5]decane-3-one (AF272); 3-methyl-1-oxa-4-thia-8-aza-spiro[4.5]decan-2-one (AF269); 3-ethyl-8-methyl-1-oxa-4-thia-8-aza-spiro[4.5]decan-2-one (AF271); 2-methyl-1-thia-4,8-diaza-spiro[4.5]decan-3-one (AF263); 3,8-dimethyl-1-oxa-4-thia-8-aza-spiro[4.5]decan-2-one (AF265); 2,8-dimethyl-1-oxa-4,8-diaza-spiro[4.5]decan-3-one (AF260); 2,4,8-trimethyl-1-thia-4,8-diaza-spiro[4.5]decan-3-one (AF266); 2-ethyl-8-methyl-1-thia-4,8-diaza-spiro[4.5]decan-3-one (AF267); 2,8-dimethyl-1-thia-4,8-diaza-spiro[4.5]decan-3-one (AF261); 2,8-dimethyl-1-oxa-3,8-diaza-spiro[4.5]dec-2-en-4-one (AF238); 2,8-dimethyl-1,3,8-triaza-spiro[4.5]dec-1-en-4-one (AF230); 3-ethyl-8-methyl-1,3,8-triaza-spiro[4.5]dec-1-en-4one (AF220); 1-ethyl-8-methyl-3-oxa-1,8-diaza-spiro[4.5]decan-2-one (AF174); 8-methyl-1-oxa-3,8-diaza-spiro[4.5]decane-2-thione (AF165); 3-ethyl-8-methyl-1-oxa-3,8-diaza-spiro[4.5]decan-2-one (AF172); 8-methyl-1-oxa-3,8-diaza-spiro[4.5]decane-2,4-dione (AF169); 3-ethyl-8-methyl-1-oxa-3,8-diaza-spiro[4.5]decane-2,4-dione (AF180); 4-butylimino-8-methyl-1,3,8-triaza-spiro[4.5]decane-2-thione (AF189); 8,N,N'-trimethyl-1,3,8-triaza-spiro[4.5]deca-1,3-diene-2,4-diamine (AF194); methyl-8-methyl-2-methylsulfanyl-1,3,8,-triaza-spiro[4.5]deca-1,3-dien-4-yl)-amine (AF193); 8-methyl-2methylsulfanyl-1,3,8-triaza-spiro[4.5]deca-1,3dien-4-ylamine (AF192); 4-metoxy-8-methyl-2-methylsulfanyl-1,3,8-triaza-spiro[4.5]deca-1,3-diene (AF191); 2,8-dimethyl-1,3,8-triaza-spiro[4.5]dec-1-ene (AF190); 3-ethyl-2-ethylsulfanyl-8-methyl-1,3,8-triaza-spiro[4.5]dec-1-ene-4-thione (AF170); 3-ethyl-2-ethylsulfanyl-8-methyl-1,3,8-triaza-spiro[4.5] dec-1-en-4-one (AF188); 8methyl-2-methylsulfanyl-1,2,8-triaza-spiro[4.5]dec-1-en-4-one(AF187); 8methyl-2,4-bis-methylsulfanyl-1,3,8-triaza-spiro[4.5]deca-1,3-diene (AF177); 8-methyl-4-methylsulfanyl-1,3,8-triaza-spiro[4.5] dec-3-ene-2-thione (AF183); 4-ethylsulfanyl-8-methyl-1,3,8-triaza-spiro[4.5]dec-3-ene-2-thione (AF176); 3ethyl-8-methyl-1,3,8-triaza-spiro[4.5]decane-2,4-dithione (AF163); 8-methyl-1,3,8-methyl-1,3,8-triaza-spiro[4.5]decane-2,4-dithione (AF173); 1-acetyl-8-methyl-1,3,8-triaza-spiro[4.5]decane-2,4-dione (AF164); 3-methyl-1,3,8-triaza-spiro[4.5]decane-2,4-dione (AF179); 3,8-dimethyl-1,3,8-triaza-spiro[4.5]decane-2,4-dione (AF178); 3-ethyl-1,3,8-triaza-spiro[4.5]decane-2,4-dione (AF160 Des); 3-ethyl-8-methyl-1,3,8-triaza-spiro[4.5]decane-2,4-dione (AF160); 3-ethyl-8-methyl-4-thioxo-1,3,8-triaza-spiro[4.5]-decan-2-one (AF182); 8-methyl-3-(4-pyrrolidin-1-yl-but-2-ynyl)-1,3,8-triaza-spiro[4.5]decane-2,4-dione (AF197); 3-prop-2-ynyl-1,3,8-triaza-spiro[4.5]decane-2,4-dione (AF186); 3-tert-butyl-8-methyl-1,3,8-triaza-spiro[4.5]decane-2,4-dione (AF213); 8-methyl-3-prop-2-ynyl-1,3,8-triaza-spiro[4.5]decane-2,4-dione (AF185); 3-tert-butyl-8-methyl-2-thioxo-1,3,8-triaza-spiro[4.5]decan-4-one (AF184); 3-ethyl-8-methyl-2-thioxo-1,3,8-triaza-spiro[4.5]decan-4-one (AF181); 3-ethyl-8-prop-2-ynyl-1,3,8-triaza-spiro[4.5]-decane-2,4-dione (AF196); 5-(1-methyl-piperidin-4-yl)-2-thioxo-imidazolidin-4-one (AF195); 5-methyl-2-(1-methyl-piperidin-4-yl)-thiazolidine-4-thione (AF275); 3-but-2-ynyl-8-methyl-1,3,8-triaza-spiro[4.5]decane-2,4-dione (AF199).

While the present invention has been particularly described herein, with especial reference to exemplified and otherwise specified embodiments, persons skilled in the art will be aware that many variations and modifications may be made. The invention is accordingly not to be construed as restricted to such embodiments which have been particularly described, rather its concept, scope and spirit are to be understood having regard to the claims which follow.

We claim:

1. A spiro-compound, including pharmaceutically acceptable salts thereof, enantiomers and racemates thereof and quaternary compounds derived therefrom when said compound has a tertiary nitrogen atom, wherein said spiro-compound contains a five-membered moiety in which a spiro-junction exists at a carbon atom thereof and simultaneously at a carbon atom of a saturated ring system containing one nitrogen atom, wherein said five-membered moiety is selected from the group consisting of 3-ethylhydantoin, 1-acetylhydantoin, 3-methylhydantoin, 3-propargylhydantoin, 2,4-dithiohydantoin, 2-thiohydantoin, oxazolidine-2-thione, 3-ethyloxazolidine-2-one, oxazolidine-2,4-dione, 3-ethyloxazolidine-2,4-dione, 2-methyl-1,4-oxazolidine-3-one, 2-methyl-1,4-thiazolidine-3-one, 2,4-dimethyl-1,4-thiazolidine-3-one, 2-ethyl-1,4-thiazolidine-3-one, 2-ethyl-1,4-thiazolidine-3-one, 2-methyl-3-oxo-1,4-thiazolidine-1-oxide, 5-methyl-1,3-dioxolane-4-one, N-methylsuccinimide, N-ethylsuccinimide, 3-t-butylhydantoin, 3-(4-pyrrolidino-2-butynyl)hydantoin, 3-(2-butynyl)-hydantoin, 2,5-bis(methylthio)-1H-imidazole, 3-ethyl-4-thiohydantoin, 4-methylthioimidazoline-2-thione, 3-ethyl-2,4-dithiohydantoin, 4-ethylthio-3-imidazoline-2-thione, 1-ethyl-2-ethylthio-2-imidazoline-5-thione, 2-thio-4β-hydroxyethyliminohydantoin, 2,5-bis(aminomethyl)-4H-imidazole, 2-methyl-2-thiazoline, 2-methyl-2-imidazoline, 2-methyl-2-oxazoline-4-one, 2-methyl-4H(5H)-imidazole-5 (4)-one, 2-methylthio-5-methoxy-4H-imidazole, 2-methylthio-5-amino-4H-imidazole, 2-methylthio-5-aminomethyl-4H-imidazole, 2-thione-3-ethylhydantoin, 2-thione-3-t-butylhydantoin, 2-methylthio-2-imidazoline-5 (4)-one), 1-ethyl-2-ethylthio-2-imidazoline-5-one and 1-ethyl-2-imidazoline-5-one; and wherein said saturated ring system containing one nitrogen atom is selected from the group consisting of moieties K, L, M, N and P:

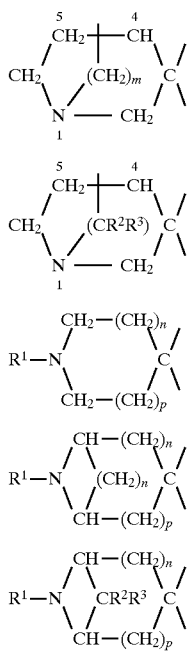

wherein each such moiety is unsubstituted or substituted by 1–3 substituents selected from $C_{1-6}$ alkyl and hydroxyl; wherein the bridge in structures K and L is attached at one end to position 1 and at the other end to position 4 or 5; wherein m is 1, 2 or 3, and n and p are each independently 0, 1, 2, or 3, provided that n+p=1–3; wherein $R^1$ is hydrogen, $C_{1-6}$-alkyl, $C_{2-6}$-alkenyl, $C_{2-6}$-alkynyl, $C_{3-7}$-cycloalkyl, $C_{1-6}$-alkyl substituted by 1–6 halogen atoms, hydroxy-$C_{1-6}$-alkyl, $C_{1-6}$-alkoxy, $C_{1-6}$alkylthio, $C_{1-6}$alkyl, carboxy-$C_{1-6}$alkyl, ($C_{1-6}$alkoxy)carbonyl-$C_{1-6}$alkyl, amino-$C_{1-6}$-alkyl, mono($C_{1-6}$-alkyl) amino $C_{1-6}$-alkyl, di-$C_{1-6}$-alkyl, 2-oxo-pyrrolidin-1-yl-methyl, aryl, diarylmethylol, $C_{1-6}$-alkyl substituted by one or two aryl groups C -alkanoyl or arylcarbonyl; wherein aryl is phenyl or phenyl substituted by 1–3 substituents selected from the group consisting of halogen, $C_{1-6}$-alkyl, $C_{1-6}$-alkoxy and $CF_3$; and wherein $R^2$ and $R^3$ are independently $C_{1-4}$ alkyl; wherein when said saturated ring system is M, n is 1, p is 1 and $R^1$ is hydrogen or methyl, said five-membered moiety is not 3-ethylhydantoin, 1-acetylhydantoin, 3-methylhydantoin, 3-propargylhydantoin, 2,4-dithiohydantoin, 2-thiohydantoin, oxazolidine-2-thione, 3-ethyloxazolidine-2-one, 3-ethyl-4-thiohydantoin, 4-methylthiomidazoline-2-thione, 3-ethyl-2,4-dithiohydantoin, 4-ethylthio-3-imidazoline-2-thione, 1-ethyl-2-ethylthio-2-imidazoline-5-thione, 2-thio-4β-hydroxyethyliminohydantoin, 2-methyl-2-thiazoline, 2-methyl-2-imidazoline, 2-methyl-2-oxazoline-4-one.

2. The spiro-compound of claim 1, wherein the saturated ring system containing one nitrogen atom is selected from piperidine, 1-methylpiperidine, 1-proparglypiperdine, N-methylnortropane and quinuclidine.

3. The spiro-compound of claim 1 selected from the group consisting of 1-methylpiperidine-4-spiro-4'-(2',5'-bis (methylthio)-4'H-imidazole); 1-methylpiperidine4-spiro-4'-(2',5'-bis-(aminomethyl)-4'H-imidazole); 1-methylpiperidine-4-spiro-4'(5')-[2'-methyl-4'H(5'H)-imidazole-5'(4')-one]; 1-methylpiperidine-4-spiro-1'-(2'-methylthio-5'-methoxy-4'H-imidazole); 1-methylpiperidine-1-spiro-4'-(2'-methylthio-5'-amino-4'H-imidazole); and 1-methylpiperidine-4-spiro-4'-(2'methylthio-5'aminomethyl-4'H-imidazole).

4. The spiro-compound of claim 1 selected from the group consisting of 1-methylnortropane-4-spiro-5'hydantion; 1-methylnortropane-4-spiro-5'-(3'-methylhydantion); 1-methylnortropane-4-spiro-5'-(3'-ethyldantion); 1-methylpiperidine-4-spiro-5'-(oxazolidine-2'-thione); 1-methylpiperidine-4-spiro-4'-(3'-ethyl-oxazolidine-2'-one); 1-methylpiperidine-4-spiro-5'-(oxazolidine-2',4'-dione); 1-methylpiperidine-4-spiro-5'-(3'-ethyloxazolidine-2',4'-dione); 1-methylpiperidine-4-spiro-5'-(2'-methyl-1',4'-oxazolidine-3'-one); 1-methylpiperidine-4-spiro-5'-(2'-methyl-1',4'-thiazolidine-3'-one); 1-methylpiperidine-4-spiro-5'-(2',4'-dimethyl-1',4'-thiazolidine-3'-one); 1-methylpiperidine-4-spiro-5'-(2'-ethyl-1','-thiazolidine-3'-one); 1-methylpiperidine-4-spiro-5'-(2'-ethyl-4-methyl-1',4'-thiazolidine- 3'-one); piperidine-4-spiro-5'-(3'-methyl-1',4'-oxathiolane-2'-one); piperidine-4-spiro-5'-(2'-methyl-1', 4'-thiazolidine-3'-one); 1-methylpiperidine-4-spiro-5'-(2'-methyl-3'-oxo-1',4'-thiazolidine-1'-oxide); 1-methylpiperidine-4-spiro-5'-(3'-methyl-1', 4'-oxathiolane-2'-one); 1-methylpiperidine-4-spiro-2'-(5'-methyl-1', 3'-oxazolidine); 1-methylpiperidine-4-spiro-2'-(4'-ethyl-1', 3'-oxazolidine); 1-methylpiperidine-4-spiro-5'-(3'-ethyl-1', 4'-oxathiolane-2'-one); 1-methylpiperidine-4-spiro-5'-(2'-methyl-1'-4'-thiazolidine-3'-one); 1-methylpiperidine-4-spiro-5'-(2'-ethyl-1', 4'-thiazolidine-3'-one); 1-methylpiperidine-4-spiro-2'-(5'-methyl-1', 3'-dioxolane-4'-one); 1-methylpiperidine-4-spiro-5'-(2'-methyl-1',4'-thiazolidine-3'-thione); 2-N-methylspiro-(1,3-succinimide-4,3')-quinuclidine; and 2-N-ethylspiro-(1,3-succinimide-4, 3')-quinuclidine.

5. The spiro-compound of claim 1 selected from the group consisting of 1-methylpiperidine-4-spiro-5'-(3'-(4-pyrrolidino-2-butynyl)-hydantoin); 1-methylpiperidine-4-spiro-5'-(3'-t- butylhydantoin); 1-propargylpiperidine-4-spiro-5'-(3'-ethylhydantoin); 1-methylpiperidine-4-spiro-5'-(3'-(2-butynyl)hydantoin); piperidine-4 -spiro-5'-(3'-propargylhydantoin); and 2-methyl-1,4-thiazolidine-3-one-spiro[5,3']-quinuclidine.

6. The spiro-compound of claim 1 selected from the group consisting of 1 -methylpiperidine-4-spiro-5'-(2'-thione-3'-ethylhydantoin); 1-methylpiperidine-4-spiro-5'-(2'-thione-3'-t-butylhydantoin); 1-methylpiperidine-4-spiro-4'(5')-(2'-methylthio-2'-imidazoline-5'(4')-one); 1-methylpiperidine-4-spiro-4'-(1'-ethyl-2'-ethylthio-2'-imidazoline-5'-one); and 1-methylpiperidine-4-spiro-4'-(1'-ethyl-2'-imidazoline-5'-one).

7. The spiro-compound of claim 1 selected from the group consisting of enantiomerically pure R-1-methylpiperidine-4spiro-5'-(2'-methyl-1',4'-thiazolidine-3'-one); S-1-methylpiperidine-4-spiro-5'-(2'-methyl-1',4'-thiazolidine-3'-one); and R-1-methylpiperidine-4-spiro-5'-(2'-ethyl-1',4'-thiazolidine-3'-one); and S-1-methylpiperidinespiro-5'-(2'-ethyl-1',4'-thiazolidine-3'-one).

8. A pharmaceutical composition which comprises at least one spiro-compound of claim 1, or a pharmaceutically acceptable salt thereof, and a pharmaceutically acceptable diluent, carrier or adjuvant.

9. A method for treating diseases associated with cholinergic hypofunction selected from the group consisting of senile dementia of Alzheimer's type, Alzheimer's disease, Lewy Body Dementia, multiifract dementia (MID), stroke ischemia, MID combined with MID (stroke/ischemia/head injury), combined MID and Alzheimer's disease, human head injury, age-associated memory impairments, acute confusion disorders, hallucinatory-paranoid states, emotional and attention disorders, mania, tardive dyskinesia, mixed Alzheimer's and Parkinson's disease, aphasia, postencephalitic amnesic syndrome, alcohol withdrawal symptoms, Huntington's chorea, Pick's disease, Friedrick's ataxia, Gilles de la Tourette disease and Down's syndrome which comprises administering to the mammal in need of such treatment a compound of claim 1 in an amount effective to treat said diseases.

* * * * *

UNITED STATES PATENT AND TRADEMARK OFFICE
CERTIFICATE OF CORRECTION

PATENT NO. : 5,852,029
DATED : December 22, 1998
INVENTOR(S) : Abraham Fisher et al.

It is certified that error appears in the above-identified patent and that said Letters Patent is hereby corrected as shown below:

On the title page, Item "[63]" first line, before "Continuation-in-part of Serial No. 94,855" please insert the following:

-- Continuation of PCT/GB94/01543 filed July 15, 1994, which is a --.

Signed and Sealed this

First Day of June, 1999

Attest:

Attesting Officer

Q. TODD DICKINSON

Acting Commissioner of Patents and Trademarks